United States Patent [19]

Or et al.

[11] Patent Number: 5,561,228

[45] Date of Patent: Oct. 1, 1996

[54] MACROCYCLIC IMMUNOMODULATORS

[75] Inventors: Yat S. Or; Jay R. Luly; Megumi Kawai, all of Libertyville; Rolf Wagner, Gurnee; Paul E. Wiedeman, Libertyville, all of Ill.

[73] Assignee: Abbott Laboratories, Abbott Park, Ill.

[21] Appl. No.: 204,252

[22] PCT Filed: Sep. 8, 1992

[86] PCT No.: PCT/US92/07593

§ 371 Date: Mar. 7, 1994

§ 102(e) Date: Mar. 7, 1994

[87] PCT Pub. No.: WO93/04679

PCT Pub. Date: Mar. 18, 1993

Related U.S. Application Data

[63] Continuation-in-part of Ser. No. 755,208, Sep. 5, 1991, abandoned.

[51] Int. Cl.$^6$ .................. C07D 498/16; A61K 31/695
[52] U.S. Cl. .......................... 540/456; 540/455
[58] Field of Search .................. 540/455, 456; 514/183, 291, 411

[56] References Cited

U.S. PATENT DOCUMENTS

| | | | |
|---|---|---|---|
| 4,894,366 | 1/1990 | Okuhara et al. | 540/456 |
| 5,064,835 | 11/1991 | Bochis et al. | 540/456 |
| 5,143,918 | 9/1992 | Bochis et al. | 540/456 |

FOREIGN PATENT DOCUMENTS

| | | | |
|---|---|---|---|
| 428365A1 | 5/1951 | European Pat. Off. | 540/456 |
| 427680A1 | 5/1991 | European Pat. Off. | 540/456 |

*Primary Examiner*—Robert T. Bond
*Attorney, Agent, or Firm*—Andreas M. Danckers; Steven R. Crowley; Gregory W. Steele

[57] ABSTRACT

Immunomodulatory macrocyclic compounds having the formula

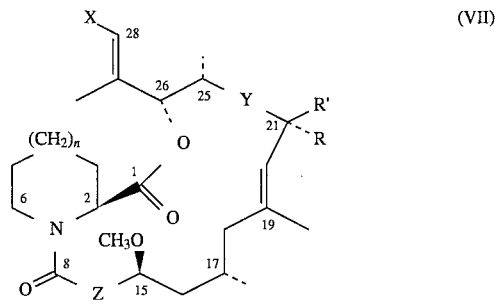

(VII)

and pharmaceutically acceptable salts, esters, amides and prodrugs thereof, wherein X is a group having the formula

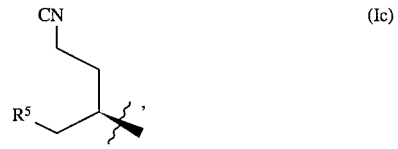

(Ic)

as well as pharmaceutical compositions containing the same.

6 Claims, No Drawings

MACROCYCLIC IMMUNOMODULATORS

This application is a continuation-in-part of U.S. patent application Ser. No. 07/755,208, filed Sep. 5, 1991, now abandoned.

FIELD OF THE INVENTION

The present invention relates to novel chemical compounds having immunomodulatory activity, and in particular to macrolide immunosuppressants. More particularly, the invention relates to semisynthetic analogs of ascomycin, means for their preparation, pharmaceutical compositions containing such compounds and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Unsatisfactory side-effects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et al., in European Patent Application No. 184162, published Jun. 11, 1986, disclose a number of macrocyclic compounds isolated from the genus Streptomyces. Immunosuppressant FK-506, isolated from a strain of S. tsukubaensis, is a 23-membered macrocyclic lactone represented by formula 1a, below. Other related natural products, such as FR-900520 (1b) and FR-900523 (1c), which differ from FK-506 in their alkyl substituent at C-21, have been isolated from S. hygroscopicus yakushimnaensis. Yet another analog, FR-900525, produced by S. tsukubaensis, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, describe the use of ascomycin as an immunosuppressant in European Patent Application No. 323865, published Jul. 12, 1989.

Although the immunosuppressive activity of FK-506 has been clinically confirmed, toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

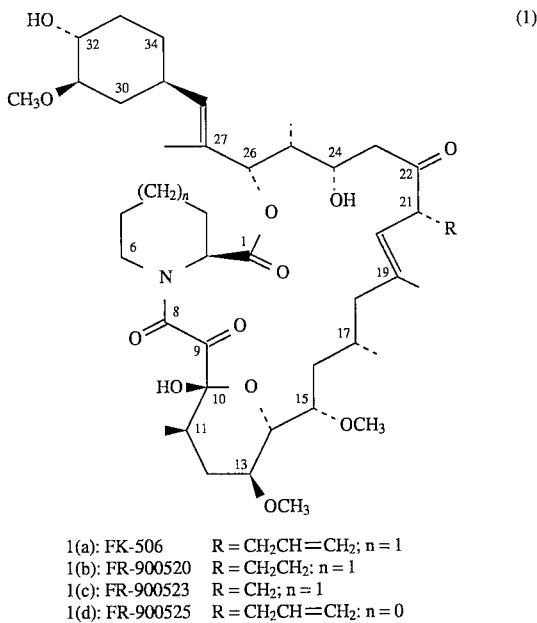

1(a): FK-506    $R = CH_2CH=CH_2$; $n = 1$
1(b): FR-900520  $R = CH_2CH_3$; $n = 1$
1(c): FR-900523  $R = CH_3$; $n = 1$
1(d): FR-900525  $R = CH_2CH=CH_2$; $n = 0$

Fermentation products of FK-type compounds include C-21-epi derivatives of FK-506; a 31-demethylated derivative of FK-506; 31-oxo-FK-506; and compounds derived from FK506, FR-900523, and FR-900525 which are characterized by the introduction of hydroxy-protecting groups, formation of a double bond by elimination of water between carbons 23 and 24, oxidation of the hydroxy group at carbon 24 to the ketone, and reduction of the allyl side-chain at carbon 21 via hydrogenation. Other published metabolites include those derived from FK-506 and FR-900520 where the lactone ring is contracted to give a macrocyclic ring containing two fewer carbons.

Several microbial transformations of FK-type compounds at carbon 13 have been published, such as the microbial demethylation of FR-900520 to form the bisdemethylated 13,31-dihydroxy ting-arranged derivative of FR-900520; the microbial monodemethylation of FK-506 and FR-900520, respectively; and the microbial demethylation of FR-900520 at C-31, as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether formation at C-32 and/or C-24, oxidation of C-32 alcohol to the ketone, and epoxide formation at C-9.

Although some of these modified compounds exhibit immunosuppressant activity, the need remains for macrocyclic compounds having immunosuppressive activity which do not have the serious side effects frequently associated with immunosuppressant therapy. Accordingly, one object of the invention is to provide novel semisynthetic macrolides which possess the desired immunomodulatory activity but which may be found to minimize untoward side effects.

Another object of the present invention is to provide synthetic processes for the preparation of such compounds from starting materials obtained by fermentation.

A further object of the invention is to provide pharmaceutical compositions containing, as an active ingredient, one of the above compounds. Yet another object of the invention is to provide a method of treating a variety of disease states, including post-transplant tissue rejection and autoimmune disfunction.

SUMMARY OF THE INVENTION

In one aspect of the present invention are disclosed compounds having the formula

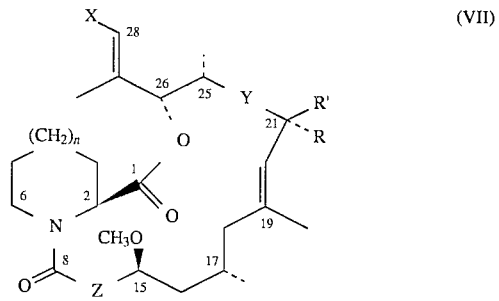

(VII)

and pharmaceutically acceptable salts, esters, amides and prodrugs thereof. In formula VII, n is zero or one, and R and R' are chosen such that one of R and R' is hydrogen and the other is selected from the group consisting of methyl, ethyl, 2-hydroxyethyl, propyl, cyclopropylmethyl, 2-oxopropyl, 2-ethanal, allyl, —$CH_2CH_2OC(O)R^{10}$ where $R^{10}$ is aryl, —$CH_2C(O)R^{12}$, —$CH_2C(O)N(R^{14'})(CH_2)_mCH(R^{16'})C(O)R^{12}$,
—$CH_2C(O)N(R^{14'})(CH_2)_mCH(R^{16'})C(O)N(R^{4''})(CH_2)_{m'}CH(R^{16''})C(O)R^{12}$, and
—$CH^2C(O)N(R^{14'})(CH_2)_mCH(R^{16'})C(O)N(R^{14''})(CH_2)_{m'}CH(R^{16''})C(O)N(R^{14'''})$—$(CH_2)_{m''}CH(R^{16'''})C(O)R^{12}$. In these formulae, m, m' and m'' are independently zero to six; $R^{16}$, $R^{16'}$ and $R^{16''}$ are independently selected from hydrogen, loweralkyl, hydroxyloweralkyl, carboxyalkyl, thioloweralkyl, thioalkoxyalkyl, guanidinoalkyl, aminoalkyl, arylalkyl and, if m, m' and m'' are other than zero, amino or amidoalkyl; and $R^{12}$ is selected from (i) hydroxy, (ii) —$OR^{13}$ where $R^{13}$ is loweralkyl, cycloalkyl, cycloalkylalkyl or arylalkyl, and (iii) —$NR^{14}R^{15}$ wherein $R^{14}$, $R^{14'}$, $R^{14''}$ and $R^{14'''}$ are independently selected from hydrogen, loweralkyl, arylalkyl, cycloalkyl and cycloalkylalkyl and $R^{15}$ is selected from hydrogen, loweralkyl, arylalkyl, cycloalkyl, cycloalkylalkyl, aminoalkyl, hydroxyalkyl, carboxyalkyl, and thioloweralkyl; or, taken together, $R^{14}$ and $R^{15}$ are —$(CH_2)_q$— where q is two to five; or, taken together with the nitrogen to which they are attached, $R^{14}$ and $R^{15}$ form a group selected from morpholino and piperidino; or, taken together, one or more of $R^{14'}$ and $R^{16}$, $R^{14''}$ and $R^{16'}$, and $R^{14'''}$ and $R^{16''}$ are —$(CH_2)_p$— where p is two to five. Alternatively, one of R and R', taken together with one of $R^{35}$ and $R^{36}$ (described below), forms a C-21/C-22 bond and the other of R and R', taken together with the other of $R^{35}$ and $R^{36}$, is a heterocycle-forming group having a formula selected from —$N(R^{63})CH=CH$— and —$OC(R^{64})=CH$— where the heteroatom in each instance is connected to C-22, $R^{63}$ is selected from hydrogen, loweralkyl, arylalkyl and aryl, and $R^{64}$ is hydrogen or loweralkyl.

Among the preferred compounds of the present invention are those in which n is one, R' is hydrogen, and R is chosen from among methyl, ethyl, propyl and allyl.

X in formula VII is a group having the subformula

(Ic)

wherein $R^5$ is selected from the group consisting of hydrogen, methyl, formyl, amino, aminomethyl, —$CH=CH_2$, —$CH_2OH$, —$CHR^6R^7$, —$C(O)NHR^{63}$, —$C(O)N(CH_3)R^{63}$, —$CH_2NHC(O)R^{63}$, —$CH_2N(CH_3)C(O)R^{63}$, —$CH_2OR^{201}$, —$CH=NOH$, —$CH=NNR^{201}R^{202}$, —$CH=NNHC(NH)NH_2$, —$CH=NOR^{201}$, —$CH=NOCH_2C(O)OH$, —$C(O)OR^{203}$, —$C(O)NR^{203}R^{204}$, —$CH_2F$, —$CH_2Cl$, —$CH_2Br$, —$CH_2N_3$, —$CH=CR^{205}R^{206}$, —$CH_2SR^{201}$, —$CH_2OR^{208}$, —$CH_2OCH_2CHCH_2$, —$CH_2OCH_2CH(OH)CH_2OH$, —$CH_2OC(O)R^{201}$, —$CH_2OC(O)NHR^{201}$, —$CH_2O$-(tert-butyldimethylsilyl), —$CH_2OCH_2OR^{201}$, —$CH(R^{204})OH$, —$CH(R^{204})OR^{201}$, —$NHR^{201}$, —$NR^{201}R^{205}$, —$NH-C(O)R^{203}$, —$N(CH_3)C(O)R^{203}$, and a radical selected from the group consisting of

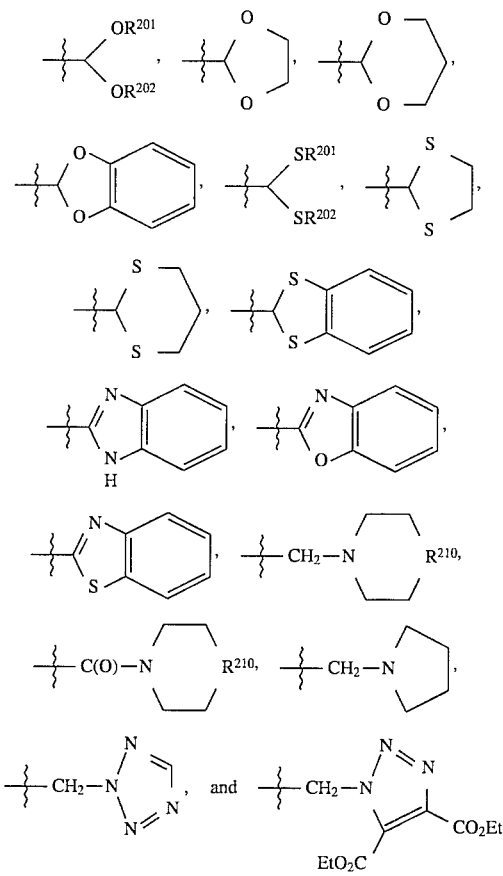

In the above, $R^6$ and $R^7$ are (a) independently selected from the group consisting of thioloweralkoxy, thioarylalkoxy, loweralkoxy and arylalkoxy, or (b) taken together, $R^6$ and $R^7$ form an acetal-forming moiety having the formula —S—$(CH_2)_g$—S—, —O—$(CH_2)_g$—O—, —O—(1,2-phenyl)—O— or —S—(1,2-phenyl)—S—, where g is two, three or four; $R^{63}$ is selected from the group consisting of hydrogen, loweralkyl, arylalkyl and aryl; $R^{201}$ and $R^{202}$ are independently selected from the group consisting of hydrogen, C 1-to-C6 loweralkyl and phenyl-substituted $C_1$-to-$C_6$ loweralkyl; $R^{203}$ is selected from the group consisting of hydrogen, $C_1$-to-$C_6$ loweralkyl, phenyl-substituted $C_1$-to-$C_6$ loweralkyl, hydroxy-substituted $C_2$-to-$C_6$ loweralkyl, piperid-1-yl-substituted $C_2$-to-$C_6$ loweralkyl and morphol-4-yl-substituted $C_2$-to-$C_6$ loweralkyl; $R^{204}$ is selected from the group consisting of hydrogen and $C_1$-to-$C_6$ loweralkyl; $R^{205}$ and $R^{206}$ are independently selected from the group consisting of hydrogen, loweralkyl and —C(O)O$R^{207}$ where $R^{207}$ is $C_1$-to-$C_6$ loweralkyl; $R^{208}$ is selected from the group consisting of phenyl and phenyl substituted with a radical selected from halogen, hydroxy, amino, nitro and $R^{203}$; and $R^{210}$ is selected from the group consisting of —CH$_2$—, —O— and —N($R^{203}$)—.

Among the preferred compounds of the present invention are those in which $R^5$ is selected from the group consisting of hydrogen, —CH=CH$_2$, —CH$_2$OH and —CH$_2$O$R^{201}$.

Y in formula VII is a group selected from the subformulae

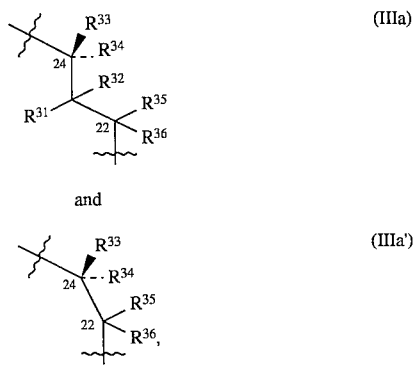

in which $R^{31}$ and $R^{32}$ are chosen such that one of $R^{31}$ and $R^{32}$ is hydrogen and the other is independently selected from the group consisting of (i) hydrogen, (ii) hydroxy, (iii) —$R^{17}$, (iv) —C(O)$R^{11}$ and (v) —CH($R^{11}$)NH$R^{17}$. Alternatively $R^{31}$ and $R^{32}$, taken together, form a diazo group; or, taken together with one of $R^{33}$ and $R^{34}$, one of $R^{31}$ and $R^{32}$ forms a C-23/C-24 bond and the other is selected from hydrogen, alkyl, —C(O)NH$R^{61}$, —S(O)$_2$ $R^{61}$ and —C(O)O$R^{61}$, where $R^{61}$ is hydrogen, aryl or loweralkyl; or, taken together with one of $R^{33}$ and $R^{34}$, one of $R^{31}$ and $R^{32}$ forms a group having the formula (in C-23 to C-24 orientation) —CH($R^{11}$)NHCH(C(O)$R^{11}$)— ; or, taken together with one of $R^{35}$ and $R^{36}$, one of $R^{31}$ and $R^{32}$ forms a C-22/C-23 bond and the other is selected from hydrogen, alkyl, —C(O)NH$R^{61}$, —S(O)$_2$$R^{61}$ and —C(O)O$R^{61}$; or $R^{31}$ and $R^{32}$, together with carbon atom C-23 to which they are attached, may be absent and replaced by a C-22/C-24 bond, as shown in subformula IIIa', above.

One or both of $R^{31}$ and $R^{32}$ may also, when taken together with one or both of $R^{33}$ and $R^{34}$ and the carbon atoms to which they are attached, form (i) a fused indole group wherein the nitrogen atom is adjacent to C-24, (ii) a fused, optionally unsaturated, 5-membered heterocyclic group wherein one of the two ring members adjacent to C-23 and C-24 is oxygen, the other adjacent ring member is —CH$R^{17}$— or =C$R^{17}$—, and the remaining ring member is =N— or —N$R^{11}$—; or (iii) a fused pyrrole. Furthermore, taken together with $R^{35}$ and $R^{36}$ and the carbon atoms to which they are attached, $R^{31}$ and $R^{32}$ may form (i) a fused indole group wherein the nitrogen atom is adjacent to C-22 or (ii) a fused furan ring wherein the oxygen atom is adjacent to C-22.

$R^{35}$ and $R^{36}$ in subformulae IIIa and IIIa' are chosen such that both are loweralkoxy; or that one of $R^{35}$ and $R^{36}$ is hydrogen and the other is selected from hydroxy, amino, —NH$R^{17}$, —OC(O)$R^{11}$, —OC(O)O-(benzyl) and —NHNH-(tosyl); or (in subformula IIIa), taken together with one of $R^{31}$ and $R^{32}$, one of $R^{35}$ and $R^{36}$ forms a C-22/C-23 bond and the other is hydrogen or hydroxy; or (in subformula IIIa'), taken together with one of $R^{33}$ and $R^{34}$ when C-23 is absent, one of $R^{35}$ and $R^{36}$ forms a C-22/C-24 bond and the other is hydrogen or hydroxy; or, taken together with one of $R^{33}$ and $R^{34}$, one of $R^{35}$ and $R^{36}$ forms a group having the formula —OC(CH$_3$)$_{20}$—; or, taken together, $R^{35}$ and $R^{36}$ form an oxo group or =N$R^{38}$ where $R^{38}$ is selected from (i) arylalkoxy, (ii) hydroxy, (iii) —OCH$_2$COOH, (iv) —OCH$_2$CHCH$_2$, (v) —NHC(O)O$R^{39}$ and (vi) —NHS(O)$_2$$R^{40}$. Alternatively, taken together with R and R', $R^{35}$ and $R^{36}$ may form a C-21/C-22 bond and a heterocycle-forming group as described above or, taken together with $R^{31}$ and $R^{32}$, $R^{35}$ and $R^{36}$ may form an indole or furan group as described above. As a further alternative, when taken together with either or both of $R^{33}$ and $R^{34}$ and intervening carbon atoms C-22, C-23 and C-24, $R^{35}$ and $R^{36}$ may form a fused, heterocyclic group selected from either (i) a five- or six-membered, unsaturated group which comprises a heteroatom selected from N, O and S, optionally comprises a heteroatom selected from N, O and S with the proviso that when two heteroatoms are present, at least one is N, and is optionally substituted with loweralkyl, aryl, arylalkyl, amido, formyl, —C(O)O$R^{11}$ or —C(O)$R^{41}$ where $R^{41}$ is loweralkyl, or (ii) a seven-membered, optionally unsaturated group having fused thereto a phenyl group optionally substituted with loweralkyl, alkoxy or halogen, wherein the ring member adjacent to C-22 is =N— and the ring member adjacent to C-24 is O or S.

$R^{33}$ and $R^M$ in subformulae IIIa and IIIa' are chosen such that (i) one of $R^{33}$ and $R^{34}$ is hydrogen and the other is selected from hydrogen, hydroxy, amino, —O$R^{11}$, —ONO$_2$, —OC(O)NH$R^{17}$, —C(O)$R^{11}$, —C($R^{11}$)NH$R^{17}$ and —O—$R^{212}$ where $R^{212}$ is a hydroxy-protecting group; (ii) one of $R^{33}$ and $R^{34}$ is hydrogen and the other forms, with one of $R^{31}$ or $R^{32}$, a group having the formula —CH($R^{11}$)NHCH(C(O)O$R^{11}$)— or, with one of $R^{35}$ and $R^{36}$, a group having the formula —OC(CH$_3$)$_2$O—; or (iii) one of $R^{33}$ and $R^{34}$ forms a C-23/C-24 bond (or, when C-23 is absent, a C-22/C-24 bond) and the other is selected from hydrogen, hydroxy and loweralkoxy. Alternatively, when taken together, $R^{33}$ and $R^{34}$ may form an oxo group or, taken together with one or more of $R^{31}$, $R^{32}$, $R^{35}$ and $R^{36}$ and the intervening carbon atoms, one or both of $R^{33}$ and $R^{34}$ form a group selected from (i) indole, where the nitrogen atom is adjacent to C-24, (ii) furan, with the oxygen atom attached to C-24, or (iii) a heterocyclic group, as described above.

Representative of Y in the compounds of the invention are the following groups:

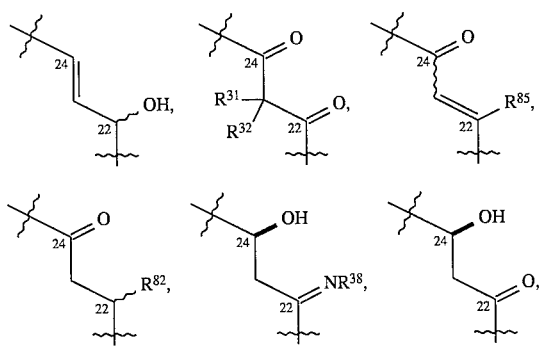

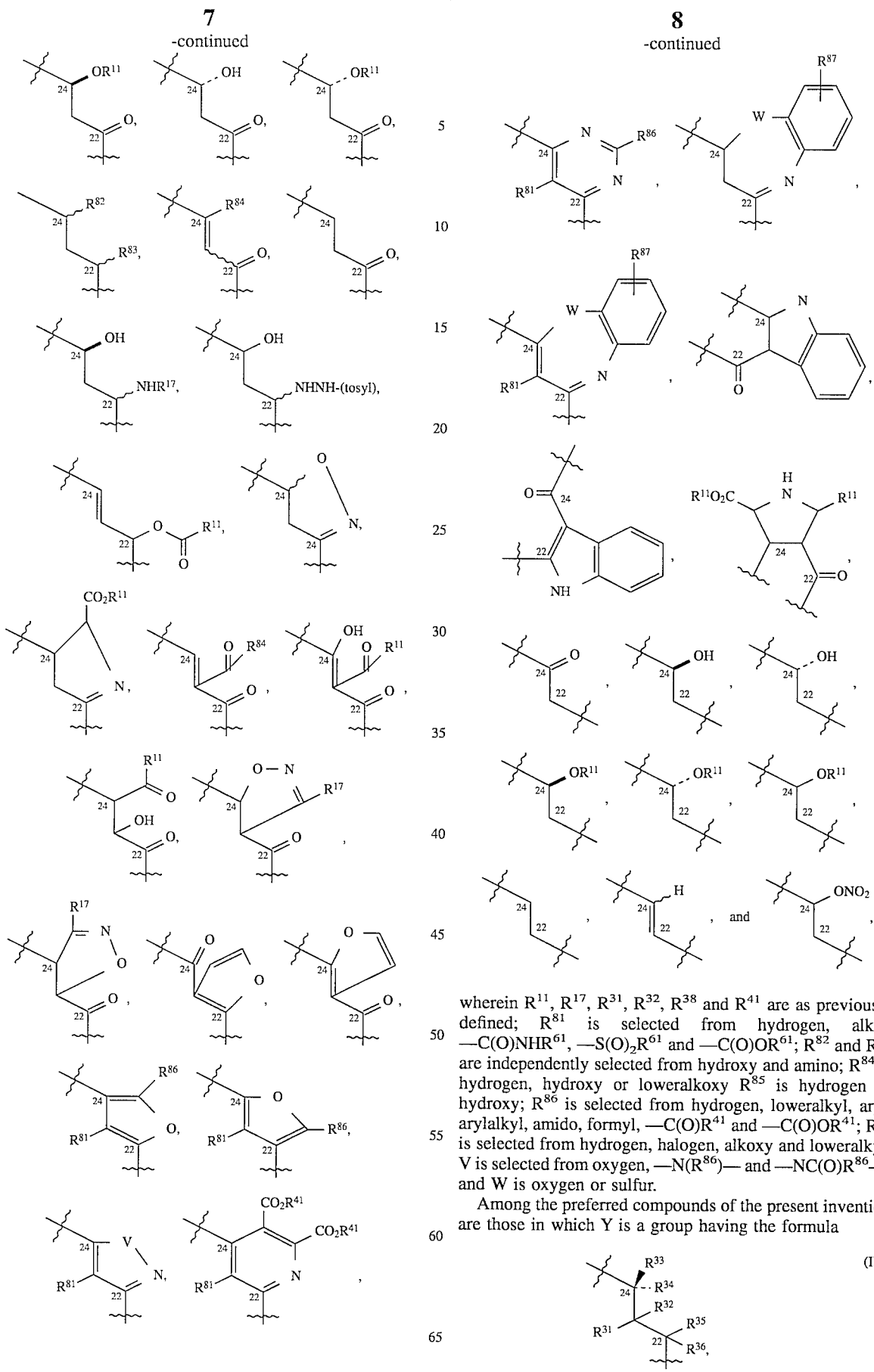

wherein $R^{11}$, $R^{17}$, $R^{31}$, $R^{32}$, $R^{38}$ and $R^{41}$ are as previously defined; $R^{81}$ is selected from hydrogen, alkyl, —C(O)NHR$^{61}$, —S(O)$_2$R$^{61}$ and —C(O)OR$^{61}$; $R^{82}$ and $R^{83}$ are independently selected from hydroxy and amino; $R^{84}$ is hydrogen, hydroxy or loweralkoxy $R^{85}$ is hydrogen or hydroxy; $R^{86}$ is selected from hydrogen, loweralkyl, aryl, arylalkyl, amido, formyl, —C(O)R$^{41}$ and —C(O)OR$^{41}$; $R^{87}$ is selected from hydrogen, halogen, alkoxy and loweralkyl; V is selected from oxygen, —N(R$^{86}$)— and —NC(O)R$^{86}$—; and W is oxygen or sulfur.

Among the preferred compounds of the present invention are those in which Y is a group having the formula (IIIa)

where (a) one of $R^{31}$ and $R^{32}$ is hydrogen and the other is hydrogen or, taken together with one of $R^{33}$ and $R^{34}$, forms a C-23/C-24 bond;

(b) one of $R^{33}$ and $R^{34}$ is hydrogen and the other is selected from the group consisting of hydrogen, hydroxy and —$OR^{212}$ or, taken together with one of $R^{31}$ and $R^{32}$, forms a C-23/C-24 bond, or, taken together, $R^{33}$ and $R^{34}$ form an oxo group; and (c) one of $R^{35}$ and $R^{36}$ is hydrogen and the other is hydroxy or, taken together, $R^{35}$ and $R^{36}$ form an oxo group.

Representative of Y in these preferred compounds are the following groups:

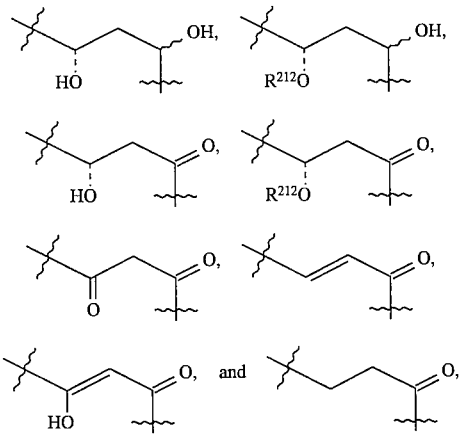

where $R^{212}$ is as previously defined.

Z in formula VII is selected from groups having the subformulae

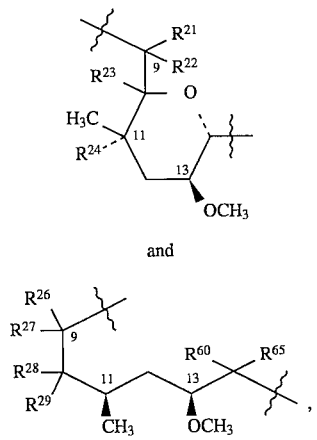

wherein
$R^{21}$ and $R^{22}$ are chosen such that (i) one of $R^{21}$ and $R^{22}$ is hydrogen and the other is selected from hydrogen, loweralkyl, arylalkyl, aryl, halogen, triflate, mesylate, tosylate, benzenesulfonate, azide, amine, acetate, —$NR^{17}R^{18}$, —$OC(O)R^{19}$, —$NR^{17}S(O)_2R^{18}$, —$NR^{17}C(O)R^{18}$, and groups having the formulae

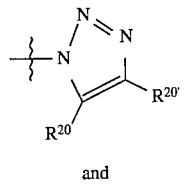

and

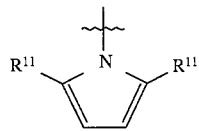

or, taken together with $R^{23}$, forms a C-9/C-10 bond. Alternatively, one of $R^{21}$ and $R^{22}$ may be hydroxy and the other selected from hydrogen, loweralkyl, arylalkyl and aryl; or one of $R^{21}$ and $R^{22}$ may be selected from hydrogen, loweralkyl and arylalkyl and the other, taken together with $R^{23}$ and the carbon atoms to which they are attached, may form a fused, five-membered heterocyclic group wherein the two ring members adjacent to C-9 and C-10 are oxygen and the remaining ring member is selected from —C(O)— and —C(S)—; or one of $R^{21}$ and $R^{22}$ may be selected from hydrogen, loweralkyl and arylalkyl and the other, taken together with $R^{23}$ and the carbon atoms to which they are attached, may form a fused, five-membered heterocyclic group wherein the two ring members adjacent C-9 and C-10 are oxygen and the remaining ring member is —$P(O)(R^{25})$— where $R^{25}$ is loweralkyl, arylalkyl, loweralkoxy, amino or loweralkylamino.

As a further alternative, $R^{21}$ and $R^{22}$, when taken together, may form an oxo group; or $R^{21}$ and $R^{22}$, taken together with the carbon to which they are attached, may be absent and C-8 attached directly to C-10.

$R^{23}$ in subformula IIa is selected from the group consisting of hydroxy, amino, loweralkylamino, arylalkylamino, loweralkoxy and arylalkoxy or, taken together with $R^{24}$, forms a C-10/C-11 bond.

$R^{24}$ in subformula IIa is hydrogen or, taken together with $R^{23}$, forms a C-10/C-11 bond.

$R^{26}$, $R^{27}$, $R^{28}$ and $R^{29}$ in subformula IIb are chosen such that (i) one of $R^{28}$ and $R^{29}$ is hydroxy and the other is —COOH or —C(O)O-loweralkyl, and (ii) $R^{26}$ and $R^{27}$ and the carbon to which they are attached are absent and C-8 is directly attached to C-10; or, taken together, $R^{26}$ and $R^{27}$ are oxo while one of $R^{28}$ and $R^{29}$ is hydroxy and the other forms a C-2/C-10 bond; or, taken together, $R^{26}$ and $R^{28}$ form a bond and $R^{27}$ and $R^{29}$ form a group having the formula —U—$C(R^{11})$=N— in which U is adjacent to C-9 and is selected from —O—, —S— and —NH—; or $R^{26}$ and $R^{28}$ are each hydroxy and $R^{27}$ and $R^{29}$, taken together, form a group having the formula —$CH_2$—$C(CH_2)$—$CH_2$—.

Alternatively, $R^{26}$, $R^{27}$, $R^{28}$ and $R^{29}$, when taken together with the carbon atoms to which they are attached, may form either (i) a fused naphthalene group wherein the atoms adjacent to C-9 and C-10 are substituted by cyano groups, or (ii) a fused, mono-, bi- or tricyclic heterocyclic aromatic group comprising fused, six-membered rings, which has between one and three nitrogen heteroatoms and is optionally substituted with up to six groups selected from amino, halogen, loweralkyl and loweralkoxy.

$R^{60}$ and $R^{65}$ in subformula IIb are chosen such that $R^{65}$ is hydrogen and $R^{60}$ is selected from the group consisting of (i) hydrogen, (ii) hydroxy and (iii) —$OC(O)R^{19}$ or, taken together, $R^{60}$ and $R^{65}$ may form an oxo group.

Representative of Z in the compounds of the present invention are the groups:

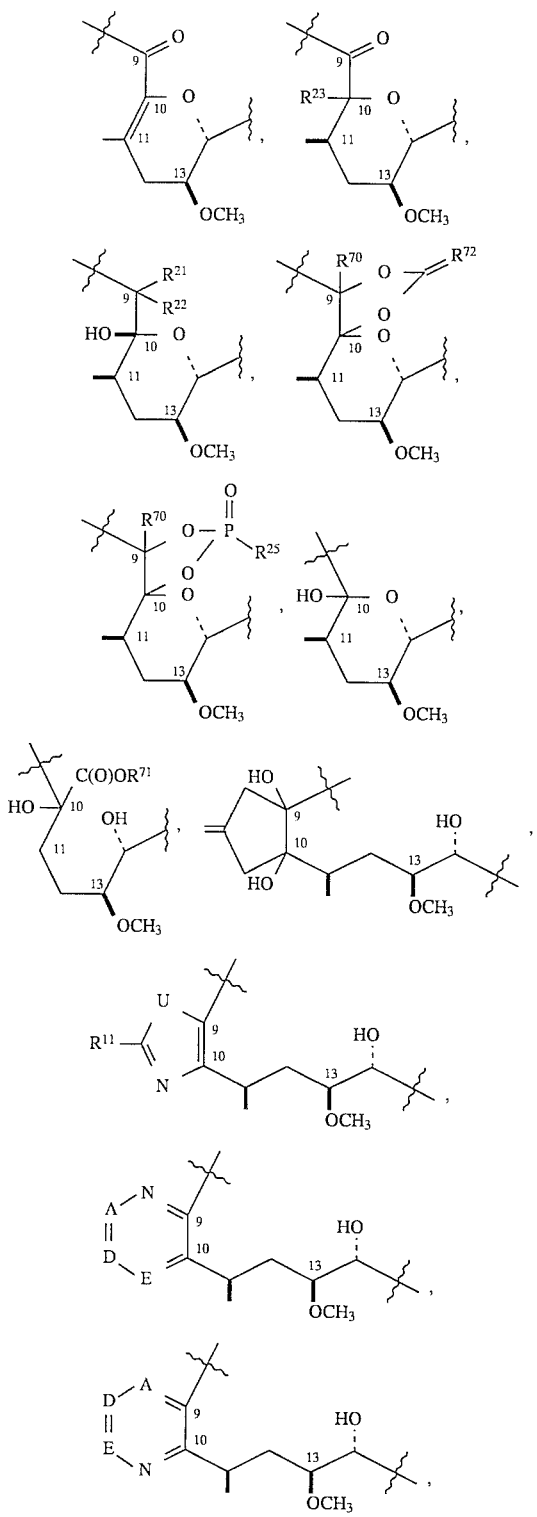

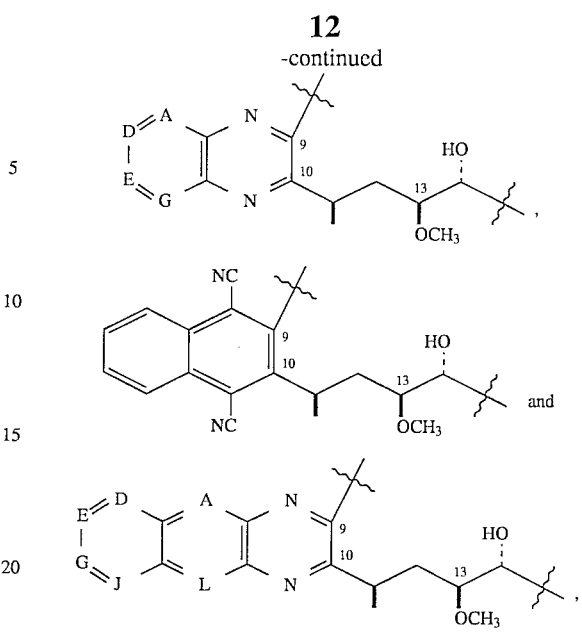

wherein $R^{11}$, $R^{21}$, $R^{22}$, $R^{23}$ and U are as previously defined; $R^{70}$ is hydrogen, loweralkyl or arylalkyl; $R^{71}$ is hydrogen or loweralkyl; $R^{72}$ is oxygen or sulfur; and A, D, E, G, J and L are selected from nitrogen, carbon and —$C(R^{73})$— where $R^{73}$ is amino, halogen, loweralkyl or loweralkoxy.

Among the preferred compounds of the present invention are those in which Z is a group having the formula

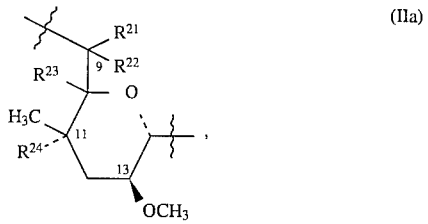

(IIa)

where
one of $R^{21}$ and $R^{22}$ is hydrogen and the other is selected from the group consisting of hydrogen and hydroxy or, taken together, $R^{21}$ and $R^{22}$ form an oxo group; $R^{23}$ is hydroxy; and $R^{24}$ is hydrogen.

The above compounds are found to possess considerable activity as immunomodulators when tested in vitro. It is noted that the most highly preferred example of the compounds of the present invention is the compound prepared in Example 425, below.

In another aspect of the present invention are disclosed pharmaceutical compositions comprising a therapeutically effective amount of a compound of the invention in combination with a pharmaceutically acceptable carrier. Suitable careers and methods of formulation are also disclosed. It is expected that the compounds and compositions of the present invention may be found to have immunosuppressive, antimicrobial, antifungal, antiviral, antiinflammatory or antiproliferative activity, and may possess the ability to reverse chemotherapeutic drug resistance.

DETAILED DESCRIPTION OF THE INVENTION

The compounds of the present invention are formed by modification of FR-900520 (ascomycin) or one of its congeners (such as FK-506, etc.) in one or more of three general regions. Accordingly, representative compounds of the invention may be categorized as belonging to one of several classes, depending on the number of modifications present. Singly-modified compounds, i.e., those in which two of the three general regions remain unchanged over the parent molecule, are those having the formula

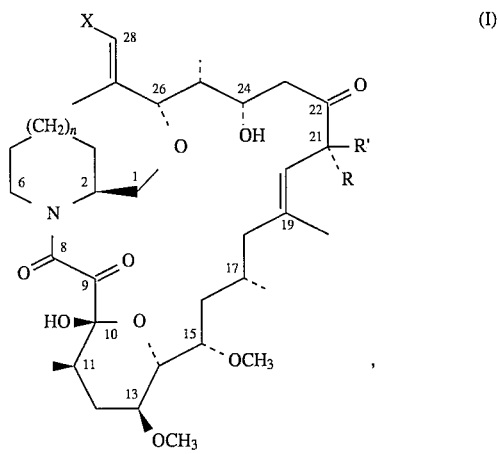

(I)

and the pharmaceutically acceptable salts, esters, amides and prodrugs thereof, wherein each of the substituents is as previously defined. On the other hand, compounds of the invention which are doubly-substituted analogs of ascomycin are those having the formulae

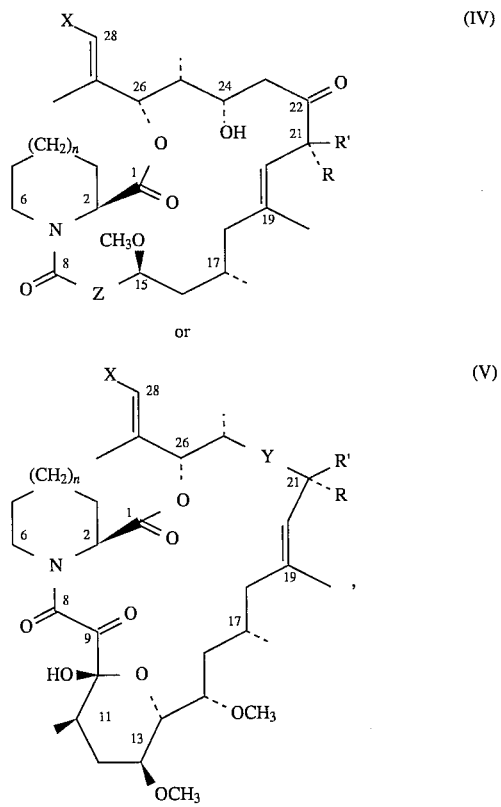

(IV)

or (V)

and the pharmaceutically acceptable salts, esters, amides and prodrugs thereof, wherein each of the substituents again are as previously defined. Multiple modifications are also possible by the careful selection of syntheses from those disclosed herein as well as by the use of other synthetic methods known to those skilled in the art, and result in the compounds encompassed by formula VII, above.

As used throughout this specification and in the appended claims, the following terms have the meanings specified:

The terms "alkoxy" and "loweralkoxy" as used herein refer to a loweralkyl group, as defined below, attached to the remainder of the molecule through an oxygen atom. Alkoxy and loweralkoxy groups include, for example, methoxy, ethoxy, isopropoxy, n-butoxy, secbutoxy, isobutoxy, tert-butoxy and the like.

The term "alkyl" as used herein refers to a monovalent straight chain or branched chain group of 1 to 12 carbon atoms including, but not limited to, methyl, ethyl, n-propyl, isopropyl, n-butyl, sec-butyl, isobutyl, tert-butyl and the like.

The terms "alkylamino" and "loweralkylamino" as used herein refers to a group having the structure —NH-(loweralkyl), where the loweralkyl portion is as defined below. Alkylamino and loweralkylamino groups include, for example, methylamino, ethylamino, isopropylamino and the like.

The term "amidoalkyl" as used herein refers to a group having the structure —NR$^{101}$C(O)R$^{102}$ appended to a loweralkyl group, as previously defined. The groups R$^{101}$ and R$^{102}$ are independently selected from hydrogen, lower alkyl, aryl, arylalkyl, and halosubstituted alkyl. Additionally, R$^{101}$ and R$^{102}$, taken together, may optionally be —(CH$_2$)$_{aa}$— where aa is an integer of from 2 to 6.

The term "aminoalkyl" as used herein refers to a group having the structure —NR$^{103}$R$^{104}$ appended to a loweralkyl group, as previously defined. The groups R$^{103}$ and R$^{104}$ are independently selected from hydrogen, lower alkyl, aryl and arylalkyl. Additionally, R$^{103}$ and R$^{104}$, taken together, may optionally be —(CH$_2$)$_{bb}$— where bb is an integer of from 2 to 6.

The term "aryl" as used herein refers to substituted and unsubstituted carbocyclic aromatic groups including, but not limited to, phenyl, 1- or 2-naphthyl, fluorenyl, (1,2)-dihydronaphthyl, (1,2,3,4)-tetrahydronaphthyl, indenyl, indanyl and the like, optionally substituted with 1, 2 or 3 substituents independently selected from halo, nitro, cyano, C$_1$ to C$_{12}$ alkyl, alkoxy and halosubstituted alkyl.

The term "arylalkoxy" as used herein refers to an arylalkyl group, as previously defined, attached to the parent molecular moiety through an oxygen atom. Arylalkoxy includes, but is not limited to, benzyloxy, 2-phenethyloxy, 1-naphthylmethyloxy and the like.

The term "arylalkyl" as used herein refers to an aryl group, as previously defined, appended to an alkyl group including, but not limited to, benzyl, 1- and 2-naphthylmethyl, halobenzyl, alkoxybenzyl, hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The term "arylalkylamino" as used herein refers to a group having the structure —NH-(arylalkyl), where the arylalkyl portion is as previously defined. Examples of arylalkylamino groups include benzylamino, 1-phenylethylamino and the like.

The term "aryloxy" as used herein refers to an aryl group, as previously defined, attached to the parent molecular moiety through an oxygen atom. Aryloxy includes, but is not limited to, phenoxy, 1-naphthoxy, 2-naphthoxy and the like.

The term "carboxyalkyl" as used herein refers to a carboxyl group, —CO$_2$H, appended to a loweralkyl group, as previously defined.

The term "cycloalkyl" as used herein refers to cyclic groups of 3 to 8 carbons including, but not limited to, cyclopropyl, cyclobutyl, cyclopentyl, cyclohexyl and the like.

The term "cycloalkylalkyl" as used herein refers to a cycloalkyl group appended to a lower alkyl group including, but not limited to, cyclohexylmethyl and cyclohexylethyl.

The term "guanidinoalkyl" as used herein refers to a group of the structure —NR$^{105}$C(=NR$^{106}$)NHR$^{107}$ appended to a loweralkyl group, as previously defined. R$^{105}$, R$^{106}$, and R$^{107}$ are independently selected from hydrogen, lower alkyl, heterocyclic, aminoalkyl and aryl. Alternatively, R$^{106}$ and R$^{107}$, taken together, may optionally be —(CH$_2$)$_{cc}$— wherein cc is an integer of from 2 to 6.

The terms "halo" and "halogen" as used herein refer to an atom selected from fluorine, chlorine, bromine and iodine.

The term "heterocyclic" as used herein, except where otherwise specified, refers to any aromatic or non-aromatic 5-, 6- or 7-membered ring or a hi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 3 double bonds, (ii) the nitrogen and sulfur heteroatoms may optionally be oxidized, (iii) the nitrogen heteroatom may optionally be quaternized, and (iv) any of the above heterocyclic tings may be fused to a benzene ring. Representative heterocycles include, but are not limited to, pyrrolyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazoyl, oxazolidinyl, isoxazolyl, isoxazolidinyl, morpholinyl, indolyl, quinolinyl, thiazolyl, thiazolidinyl, isothiazolyl, isothiazolidinyl, isoquinolinyl, benzimidazolyl, benzothiazolyl, benzoxazolyl, furyl, thienyl and benzothienyl.

The terms "hydroxyalkyl" and "hydroxyloweralkyl" as used herein refer to —OH appended to a loweralkyl group, as defined below.

The term "hydroxy-protecting group" as used herein refers to those groups which are known in the an to protect a hydroxyl group against undesirable reaction during synthetic procedures and to be selectively removable including, but not limited to, methylthiomethyl, tert-dimethylsilyl, tert-butyldiphenylsilyl, acyl substituted with an aromatic group and the like.

The term "loweralkyl" as used herein refers to an alkyl group, as defined above, of 1 to 8 carbon atoms.

The terms "naturally occuring amino acid" and "standard amino acid" refer to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

The term "N-terminal protecting group" as used herein refers to those groups known in the an to protect the N-terminus against undesirable reactions during synthetic procedures or to prevent the attack of exopeptidases on the final compounds or to increase the solubility of the final compounds and includes, but is not limited to acyl, acetyl, pivaloyl, tert-butylacetyl, tert-butyloxycarbonyl (Boc), carbobenzyloxycarbonyl (Cbz), and benzoyl groups. Other such groups are described by Gross, E. and Meienhofer, J. in "The Peptides", Volume 3; Academic Press, 1981.

The terms "thioalkoxy" and "thioloweralkoxy" as used herein refer to a loweralkyl group, as previously defined, attached to the remainder of the molecule through a sulfur atom. Examples of thioalkoxy and thioloweralkoxy groups include, but are not limited to, thiomethoxy, thioethoxy, thioisopropoxy, n-thiobutoxy, sec-thiobutoxy, isothiobutoxy, tert-thiobutoxy and the like.

The term "thioalkoxyalkyl" as used herein refers to a thioalkoxy group, as defined above, appended to a loweralkyl group.

The term "thioarylalkoxy" as used herein refers to an arylalkyl group, as previously defined, attached to the remainder of the molecule through a sulfur atom.

The term "thioaryloxy" as used herein refers to an aryl group, as defined above, attached to the remainder of the molecule through a sulfur atom.

The term "thioloweralkyl" as used herein refers to a loweralkyl group, as defined above, attached to the remainder of the molecule through a sulfur atom.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with with the tissues of humans and lower animals with undue toxicity, imitation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et al., "Pharmaceutical Salts," *J. Pharm. Sci.*, 66: 1–19 (1977) which is incorporated herein by reference.)

Examples of pharmaceutically acceptable, non-toxic esters of the compounds of this invention include $C_1$ to $C_6$ alkyl esters wherein the alkyl group is a straight or branched chain. Acceptable esters also include $C_5$ to $C_7$ cycloalkyl esters as well as arylalkyl esters such as, but not limited to benzyl. $C_1$ to $C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$ to $C_6$ alkyl amines and secondary $C_1$ to $C_6$ dialkyl amines wherein the alkyl groups are straight or branched chain. In the case of secondary amines the amine may also be in the form of a 5 or 6 membered heterocycle containing one nitrogen atom. Amides derived from ammonia, $C_1$ to $C_3$ alkyl primary amides and $C_1$ to $C_2$ dialkyl secondary amides are preferred. Amides of the compounds of the invention may be prepared according to conventional methods.

The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimede) method, the active ester method (p-nitrophenyl ester method, N-hydroxysuccinic acid imide ester method, cyanomethyl ester method and the like), the Woodward reagent K method, the DCC-HOBT (1-hydroxy-benzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Z), o-chlorobenzyloxycarbonyl ((2-Cl)Z)), p-nitrobenzyloxycarbonyl (Z(NO$_2$)), p-methoxybenzyloxycarbonyl (Z(OMe)), t-amyloxycarbonyl (Aoc), isobomealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt) and dimethylphosphino-thioyl (Mpt).

The examples for protecting groups or carboxyl groups involve, for example, benzyl ester (OBzl), cyclohexyl ester, 4-nitrobenzyl ester (OBzlNO$_2$), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mts) and the like; the thiol group in cysteine may be protected with benzyl, p-methoxybenzyl, triphenylmethyl, acetomidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP) and the like.

Numerous asymmetric centers may exist in the compounds of the present invention. Except where otherwise noted, the present invention contemplates the various stereoisomers and mixtures thereof. Accordingly, whenever a bond is represented by a wavy line, it is intended that both steric orientations are intended.

The compounds of the invention, including but not limited to those specified in the examples, possess immunomodulatory activity in animals. As immunosuppressants, the compounds are expected to be useful in the treatment and/or prevention of rejection of transplanted organs or tissues, such as kidney, heart, lung, bone meow, skin or cornea transplants, and also in the treatment or prevention of autoimmune, inflammatory, proliferative, and hyperproliferative diseases, such as rheumatoid arthritis, lupus erythematosus, sytemic lupus erythematosus, multiple sclerosis, myasthenia gravis, type I diabetes, uveitis, Hashimoto's thyroiditis, nephrotic syndrome, psoriasis, atopical dermatitis, contact dermatitis, seborrheic dermatitis, graft-versus-host diseases by medulla ossium transplantation, vernal keratocojunctivitis, eczematous dermatises, lichen planu, pemphigus, bullous pemphigoid, epidermolysis bullosa, urticaria, angioedemas, vasculitides, erythemas, cutaneous eosinophilias, alopecia arcata and the like.

The compounds of this invention are also expected to find use in the treatment of reversible obstructive airways disease. Further, the compounds of this invention may be indicated in the treatment of diseases caused by intestinal inflammations and allergies, such as Coeliac disease, gastroenteritis, mastocytosis, Crohn's disease, ulcerative colitis, and the like; and food-related allergic diseases which have symptoms remote from the gastrointestinal tract, as for example migraine, rhinitis, and eczema.

Additionally, some compounds appear to possess FK-506 antagonistic properties. The compounds of the present invention may thus be used in the treatment of immunodepression or a disorder involving immunodepression. Examples of disorders involving immunodepression include AIDS, cancer, senile dementia, trauma (including wound healing, surgery and shock) chronic bacterial infection, and certain central nervous system disorders. The immunodepression to be treated may be caused by an overdose of an immunosuppressive macrocyclic compound, for example derivatives of 12-(2-cyclohexyl-1-methylvinyl)-13, 19,21, 27-tetramethyl- 11,28-dioxa-4-azatricyclo[22.3.1.0$^{4,9}$]octacos-18-ene such as FR- 900506, or rapamycin. Overdosing of such medicants by patients is quite common upon their realizing that they have forgotten to take their medication at the prescribed time and can lead to serious side effects.

A further situation in which the compounds of the present invention may be used to treat immunosuppression is in vaccination. It is sometimes found that the antigen introduced into the body for the acquisition of immunity from disease acts as an immunosuppressive agent, and so antibodies are not produced by the body and immunity is not acquired. By introducing a compound of the invention into the body (as in a vaccine), the undesired immunosuppression may be overcome and immunity acquired.

Aqueous liquid compositions of the present invention may be particularly useful for the treatment and prevention of various diseases of the eye such as autoimmune diseases (including, for example, conical cornea, keratitis, dysophia epithelialis corncue, leukoma, Mooren's ulcer, sclevitis and Graves' ophthalmopathy) and rejection of corneal transplantation.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective mount" of the compound of the invention is meant a sufficient amount of the compound to treat gastrointestinal disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.001 to about 3 mg/kg/day. For purposes of oral administration, more preferable doses may be in the range of from about 0.005 to about 1.5 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, or drops), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carders, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlombutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drag from subcutaneous or intramuscular injection. This may be accomplished by the use of a liquid suspension of crystalline or amorphous material with poor water solubility. The rate of absorption of the drag then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carder such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the an such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carder comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immune-mediated conditions of the eye such as autoimmune diseases, allergic or inflammatory conditions, and corneal transplants. The compound of the invention is delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of this invention with suitable non-irritating excipients or careers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The compounds of the invention may be prepared using one or more of the processes which follow. The starting materials for use in these processes are preferably one of the macrolides isolated from culture media obtained in accordance with known methods by fermentation of microorganisms of the genus Streptomyces, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, U.S.A. under the provisions of the Budapest Treaty, under deposit No. NRRL 18488. The macrolide FR-900520 (European Patent Application 0184162), also known as ascomycin, may be prepared in accordance to the published methods of (i) H. Hatanaka, M. Iwami, T. Kino, T. Goto and M. Okuhara, FR-900520 and FR-900523, *Novel immunosuppressants isolated from A streptomyces. I. Taxonomy of the producing strain. J. Antiblot.*, 1988. XLI(11), 1586–1591; (ii) H. Hatanaka, T. Kino, S. Miyata, N. Inamura, A. Kuroda, T. Goto, H. Tanaka and M. Okuhara, FR-900520 and FR-900523, *Novel immunosuppressants isolated from A streptomyces. II. Fermentation, isolation and physico-chemical and biological characteristics. J. Antibiot.*, 1988. XLI(11), 1592–1601; (iii) T. Arai, Y. Koyama, T. Suenaga and H. Honda, *Ascomycin, An Antifungal Antibiotic. J. Antibiot.*, 1962. 15(231–2); and (iv) T. Arai in U.S. Pat. No. 3,244,592. One or more of the processes discussed below may be then employed to produce the desired compound of the invention.

Such processes comprises:

(a) producing a compound of formulae I–VIII, which contains a CH—OR group, by selective activation of a selected CH—OH group in a corresponding compound wherein —OR is a leaving group which is easily displaced by nucleophilic attack.

(b) producing a compound of formulae I–VIII, which contains a CH—$N_3$ group, by selective displacement of an —OR group in a corresponding compound.

(c) producing a compound of formulae I–VIII, which contains a CH—$NH_2$ group, by selective reduction of a CH—$N_3$ group in a corresponding compound.

(d) producing a compound of formulae I–VIII, which contains a CH—NHCOR group, by selective acylation of a CH—$NH_2$ group in a corresponding compound wherein R is selected from hydrogen, aryl, arylalkyl, alkyl, heterocyclic, heterocyclic alkyl, cycloalkyl, and cycloalkylalkyl.

(e) producing a compound of formulae I–VIII, which contains a CH—$NR_1R_2$ group, by selective alkylation of a CH—$NH_2$ group in a corresponding compound wherein $R_1$ and $R_2$ are independently selected from hydrogen, aryl, arylalkyl, alkyl, heterocyclic, heterocyclic alkyl, cycloalkyl, and cycloalkylalkyl.

(f) producing a compound of formulae I–VIII, which contains a CH–NHC(=X)NH—R group, by selective urea or thiourea formation from a CH—$NH_2$ group in a corresponding compound wherein R is selected from hydrogen, aryl, arylalkyl, alkyl, heterocyclic, heterocyclic alkyl, cycloalkyl, and cycloalkylalkyl, and X is oxygen or sulfur.

(g) producing a compound of formulae I–VIII, which contains a CH—NH—$SO_2$R group. by selective sulfonylation of a CH—$NH_2$ group in a corresponding compound wherein R is selected from aryl, arylalkyl, alkyl, cycloalkyl, cycloalkylalkyl, heterocyclic alkyl and heterocyclic.

(h) producing a compound of formulae I–VIII, which contains a CH—NH—C(=O)OR group, by selective carbamate formation from a selected CH—NH$_2$ group in a corresponding compound wherein R is selected from aryl, cycloalkyl, cycloalkyl alkyl, alkyl, heterocyclic alkyl, heterocyclic and arylalkyl.

(i) producing a compound of formulae I–VIII, which contains a CH—NH—C(=NH)NH$_2$ group, by selective guanidinium formation from a CH—NH$_2$ group in a corresponding compound.

(j) producing a compound of formulae I–VIII, which contains a CH—NH—SR group, by selective sulfenylation of a CH—NH$_2$ group in a corresponding compound wherein R is selected from aryl, arylalkyl, alkyl, cycloalkyl, cycloalkylalkyl, heterocyclic alkyl and heterocyclic.

(k) producing a compound of formulae I–VIII, which contains a CH—X group, by selective halogenation of a CH—OH group in a corresponding compound wherein X is selected from chlorine, bromine, fluorine and iodine.

(l) producing a compound of formulae I–VIII, which contains a CH—P(O)(OR)$_2$ group, by selective phosphonic acid ester formation of a CH—X group in a corresponding compound wherein R is selected from alkyl, arylalkyl, and aryl.

(m) producing a compound of formulae I–VIII, which contains a CH—O—P(O)(OR)$_2$ group, by selective phosphorylation of a CH—OH group in a corresponding compound wherein R is selected from alkyl, arylalkyl, and aryl.

(n) producing a compound of formulae I–VIII, which contains a CH—S—R group, by selective thioether formation from a CH—OH group in a corresponding compound wherein R is selected from cycloalkyl, cycloalkyl alkyl, heterocyclic, heterocylic alkyl, alkyl, arylalkyl, and aryl.

(o) producing a compound of formulae I–VIII, which contains a CH—O—C(=S)—OR group, by selective aryl- or alkyloxythiocarbonylation of a CH—OH group in a corresponding compound wherein R is selected from cycloalkyl, cycloalkyl alkyl, heterocyclic, heterocylic alkyl, alkyl, arylalkyl, and aryl.

(p) producing a compound of formulae I–VIII, which contains one or more CH—O—R groups, by selective ether formation of one or more CH—OH groups in a corresponding compound wherein R is selected from cycloalkyl, cycloalkyl alkyl, heterocyclic, heterocylic alkyl, alkyl, arylalkyl, aryl, lower alkoxycarbonylalkyl, arylalkoxycarbonylalkyl, and arylalkylcarbonylalkyl.

(q) producing a compound of formulae I–VIII, which contains a CH-(substituted)phthalimide group, by selective cyclic imide formation using a CH—NH$_2$ group in a corresponding compound.

(r) producing a compound of formulae I–VIII, which contains a CH—NH—P(=Y)R$_2$ group, by selective phosphinamide formation from a CH—NH$_2$ group in a corresponding compound wherein R is phenyl, or substituted phenyl and Y is oxygen or sulfur.

(s) producing a compound of formulae I–VIII, which contains CH—N—P(=Y)(OR)$_2$ group, by selective phosphoramide formation from a CH—NH$_2$ group in a corresponding compound wherein R is phenyl, arylalkyl, or substituted phenyl and Y is oxygen or sulfur.

(t) producing a compound of formulae I–VIII, which contains a CH$_2$ group, by selective deoxygenation of a CH—O—C(=S)—OR group in a corresponding compound.

(u) producing a compound of formulae I–VIII, which contains a C(OH)=CH—C(=O) or a C(=O)—CH$_2$—C(=O) group, by selective oxidation of a CH(OH)—CH$_2$—C(=O) group in a corresponding compound.

(v) producing a compound of formulae I–VIII, which contains a C(=O)—CR$_1$R$^2$—C(=O) group, by selective alkylation of a C(OH)=CH—C(=O) or a C(=O)—CH$_2$—C(=O) group in a corresponding compound wherein R$_1$— and R$^2$ are independently selected from hydrogen, aryl, cycloalkyl, cycloalkyl alkyl, alkyl, heterocyclic alkyl, heterocyclic and arylalkyl, but both cannot be hydrogen.

(w) producing a compound of formulae I–VIII, which contains a C(=O)—CR$_1$R$_2$—C(=O) group, by selective halogenation of a C(OH)=CH—C(=O) or a C(=O)—CH$_2$—C(=O) group in a corresponding compound wherein R$^1$ and R$^2$ are independently selected from fluorine, chlorine, bromine and iodine.

(x) producing a compound of formulae I–VIII, which contains a C(=O)—CH(OH)—C(=O) group, by selective oxidation of a C(OH)=CH—C(=O) or a C(=O)—CH$_2$—C(=O) group in a corresponding compound.

(z) producing a compound of formulae I–VIII, which contains a C(=O)—C(N$_2$)—C(=O) group, by selective diazotization of a C(OH)=CH—C(=O) or a C(=O)—CH$_2$—C(=O) group in a corresponding compound.

(aa) producing a compound of formulae I–VIII, which contains a C(=CH—R)—CH$_2$C—(=O) group, by selective olefination of a C(OH)=CH—C(=O) or a C(=O)—CH$_2$—C(=O) group in a corresponding compound wherein R is selected from lower alkyl and arylalkyl.

(bb) producing a compound of formulae I–VIII, which contains a C(OCOR)=CH—C(=O) group, by selective O-acylation of a C(OH)=CH—C(=O) or a C(=O)—CH$_2$—C(=O) group in a corresponding compound wherein R is selected from aryl, cycloalkyl, cycloalkyl alkyl, alkyl, heterocyclic alkyl, heterocyclic and arylalkyl.

(cc) producing a compound of formulae I–VIII, which contains a C(NH—R)=CH—C(=O) group, by selective amination of a C(OH)=CH—C(=O) or a C(=O)—CH$_2$—C(=O) group in a corresponding compound wherein R is selected from alkylamine, arylalkylamine, arylamine and amino acid derivatives.

(dd) producing a compound of formulae I–VIII, which contains C(O)—C(=CH—R)—C(=O) group, by selective alkylidene formation of a C(OH)—CH—C(=O) or a C(=O)—CH$_2$—C(=O) group in a corresponding compound wherein R is selected from hydrogen, aryl, cycloalkyl, cycloalkyl alkyl, alkyl, heterocyclic alkyl, heterocyclic and arylalkyl.

(ee) producing a compound of formulae I–VIII, which contains a carbon-carbon double bond, by elimination of HL from a corresponding compound, where L is a leaving group.

(ff) producing a compound of formulae I–VIII, which contains a quinoxaline, benzoquinoxaline, pyrazino[2,3-d]pyridazine, pyrido[3,4-b]pyrazine, or a pteridine by condensation of a 1,2-dicarbonyl or masked 1,2-dicarbonyl groups of a corresponding compound with an appropriate aromatic diamine.

(gg) producing a compound of formulae I–VIII, which contains one or more hydroxyl groups, by selective reduction of one or more C=O groups of a corresponding compound.

(hh) producing a compound of formulae I–VIII, which contains one dihydrobenzo[1,5]thiazepine, by reaction of an alpha,beta-unsaturated ketone of a corresponding compound with an appropriate 2-aminothiophenol.

(ii) producing a compound of formulae I–VIII, which contains one or more carbonyl groups, by selective oxidation of one or more hydroxyl groups of a corresponding compound.

(jj) producing a compound of formulae I–VIII, by selective reaction of one of the carbonyl groups of a corresponding compound and dithiols.

(kk) producing a compound of formulae I–VIII, which contains an oxime or a nitrone group, by selective reaction of one of the carbonyl groups of a corresponding compound with hydroxylamine or O-alkylated hydroxylamines, or with an N-alkylhydroxylamine, respectively.

(ll) producing a compound of formulae I–VIII, which contains a pyrazole system, by condensation of a 1,3-dicarbonyl group of a corresponding compound and appropriate hydrazines.

(mm) producing a compound of formulae I–VIII, which contains a substituted pyrimidine system, by condensation of the 1,3-dicarbonyl group of a corresponding compound with appropriate amidines, guanidines, isoureas, ureas and thioureas.

(nn) producing a compound of formulae I–VIII, which contains a furan system, by reaction of the 1,3-dicarbonyl group of a corresponding compound with appropriate diazoacetic esters or diazomethyl ketones.

(oo) producing a compound of formulae I–VIII, which contains an isoxazole system, by condensation of the 1,3-dicarbonyl group of a corresponding compound with hydroxyl amine.

(pp) producing a compound of formulae I–VIII, which contains a pyridine system, by condensation of the 1,3-dicarbonyl group of a corresponding compound with appropriate malonic acid derivatives or cyanoacetic acid derivatives.

(qq) producing a compound of formulae I–VIII, which contains a benzo[1,5]thiazepine, benzo[1,5]oxazepine or benzo[1,5]diazepine system, by condensation of the 1,3-dicarbonyl group of a corresponding compound with appropriate 2-aminothiophenols, 2-aminophenols, and 1,2-aromatic diamines.

(rr) producing a compound of formulae I–VIII, which contains a keto-substituted furan system, by reaction of the 1,3-dicarbonyl group of a corresponding compound with appropriate aldehydes, and enol ethers.

(ss) producing a compound of formulae I–VIII, which contains a substituted phenyl group, by C-arylation of a 1,3-dicarbonyl group of a corresponding compound with appropriate 1-halo-2-nitro-aromatics.

(uu) producing a compounds of formulae I–VIII, which contains a 2-isoxazoline, by nitrile oxide 1,3-dipolar cycloaddition to an enone.

(zz) producing a compound of formulae I–VIII, which contain either a beta-hydroxy ketone or an alpha,beta-enone, by reductive hydrolysis of a corresponding 2-isoxazoline and subsequent separation of the two compounds.

(eee) producing a compound of formulae I–VIII, which contains a hydrazone, by selective hydrazone formation with a corresponding ketone.

(fff) producing a compound of formulae I–VIII, which contains either an alpha-hydroxy, beta-keto acid or ester, by selective nucleophilic addition and subsequent benzilic acid type rearrangement of a corresponding compound containing a tricarbonyl moiety.

(ggg) producing a compound of formulae I–VIII, which contains a 1,2-dicarbonyl system, by selective oxidative cleavage of a benzilic acid rearrangement product which has been derived from a corresponding compound.

(hhh) producing a compound of formulae I–VIII, which contains an allylic alcohol, by selective reduction of a corresponding enone.

(iii) producing a compound of formulae I–VIII, which contains an epoxide, by selective addition of the carbene arising from diazomethane across an activated carbonyl.

(jjj) producing a compound of formulae I–VIII, which contains a carboxylic acid, by selective ester cleavage in a corresponding compound.

(kkk) producing a compound of formulae I–VIII, which contains a substituted or unsubstituted carboxamide, by selective condensation of the corresponding amine with a corresponding carboxylic acid.

(lll) producing a compound of formulae I–VIII, which contains a 24R-hydroxyl substituent, by selective inversion of the naturally occurring 24S configuration.

(mmm) producing a compound of formulae I–VIII, which contains an alkyloxycarbonyl hydrazone, by selective condensation of an alkyl carbazate with a corresponding compound of formulae I–VIII, having a ketone.

(nnn) producing a compound of formulae I–VIII, which contains a C-33-alkylcarbonyl or polyhaloalkylcarbonyl substituent, by selective C-acylation of 32-oxo-ascomycin or a related analog.

(ooo) producing a compound of formulae I–VIII, which contains a 33-diazo moiety, by selective diazotization of a derivative of 32-oxo-ascomycin or a related analog.

(ppp) producing a compound of formulae I–VIII, which contains one thiazole, by condensation of an alpha substituted carbonyl or an alpha substituted masked carbonyl group of a corresponding compound with an appropriate thioamide, thiourea or with dithiocarbamic acid derivatives, where the alpha substituent L is a leaving group.

(qqq) producing a compound of formulae I–VIII, which contains one imidazole, by condensation of an alpha substituted carbonyl or an alpha substituted masked carbonyl group of a corresponding compound with an appropriate amidine, isourea or guanidine, where the substituent L is a leaving group.

(rrr) producing a compound of formulae I–VIII, which contains one oxazole, by condensation of an alpha substituted carbonyl or an alpha substituted masked carbonyl group of a corresponding compound with an appropriate amide, where the substituent L is a leaving group.

(sss) producing a compound of formulae I–VIII, which contains a tertiary alcohol, by selective addition of a Grignard reagent or an organometallic reagent to a carbonyl moiety of a corresponding compound.

(ttt) producing a compound of formulae I–VIII, which contains one pyrrole, by cyclization of an appropriate gamma-amino alpha hydroxy carbonyl or a masked gamma-amino alpha hydroxy carbonyl of a corresponding compound prepared by process (sss).

(uuu) producing a compound of formulae I–VIII, which contains one pyrazine, by condensation of a 1,2-dicarbonyl or masked 1,2-dicarbonyl group of a corresponding compound with an appropriate 1,2-diamine in the presence of an oxidizing agent.

(vvv) producing a compound of formulae I–VIII, which contains one pyridine, by condensation of a 1,5-dicarbonyl group prepared by process (sss) of a corresponding compound with ammonia.

(www) producing a compound of formulae I–VIII, which contains one pyridazine, by condensation of a 1,4-dicarbonyl group prepared by process (sss) of a corresponding compound with hydrazine.

(xxx) producing a compound of formulae I–VIII, which contains a 1,2-thiocarbonate, by reacting a 1,2-diol of a corresponding compound with thiocarbonyldiimidazole or an appropriately activated thiocarbonate.

(yyy) producing a compound of formulae I–VIII, which contains a 1,2-carbonate, by reacting a 1,2-diol of a corresponding compound with carbonyldiimidazole, triphosgene, phosgene or an appropriately activated carbonate.

(zzz) producing a compound of formulae I–VIII, which contains a 1,2-phosphonate group, by reacting a 1,2-diol of a corresponding compound with an appropriate alkoxyphosphonyl dichloride.

(aaaa) producing a compound of formulae I–VIII, which contains an olefin, by reduction of a 1,2-thiocarbonate prepared by process (xxx) of a corresponding compound.

(bbbb) producing a compound of formulae I–VIII, which contains a $CH_2$ group, by selective reduction of a 1,2-dicarbonyl or masked 1,2-dicarbonyl group of a corresponding compound.

(cccc) producing a compound of formulae I–VIII, which contains an indole group, by selective reduction and condensation of a 2-(o-nitrophenyl)-1,3-diketone [prepared by process (ss)] of a corresponding compound.

(dddd) producing a compound of formulae I–VIII, which contains a substituted triazole group, by cycloaddition of a CH—$N_3$ group in a corresponding compound with appropriate acetylene analogues.

(eeee) producing a compound of formulae I–VIII, which contains a substituted pyrrole group, by reaction of a CH—$NH_2$ group in a corresponding compound with appropriate dicarbonyl compounds.

(ffff) producing a compound of formulae I–VIII, which contains one ethanalyl group, first by selective oxidation of the double bond of an allyl group to a vicinal diol, followed by oxidative cleavage of the diol in a corresponding compound, (gggg) producing a compound of formulae I–VIII, which contains one carboxymethyl group, by selective oxidation of an ethanalyl group in a corresponding compound, (hhhh) producing a compound of formulae I–VIII, which contains one alkyl carboxymethyl group, by esterification of a carboxymethyl group in a corresponding compound, (iiii) producing a compound of formulae I–VIII, which contains one cyclopropylmethyl group, by selective cyclopropanation of the double bond of an allyl group in a corresponding compound, (jjjj) producing a compound of formulae I–VIII, which contains one pyrrole, by reaction of a 1,4-dicarbonyl group with amines in a corresponding compound, (kkkk) producing a compound of formulae I–VIII, which contains one furan, by cyclization of a 1,4-dicarbonyl group in a corresponding compound, (llll) producing a compound of formulae I–VIII, which contains one methyl ketone, by selective oxidation of the double bond of an allyl group in a corresponding compound, (mmmm) producing a compound of formulae I–VIII, which contains a cyano group by Beckmann fragmentation of an oxime derivative of an alpha-methoxy cyclohexanone in a corresponding compound, (nnnn) producing a compound of formulae I–VIII, which contains a hydrazide, by reduction of the corresponding hydrazone, (oooo) producing a compound of formulae I–VIII, which contains an mine, by reduction of the corresponding oxime, (pppp) producing a compound of formulae I–VIII, which contains an alpha,beta-saturated ketone, by reduction of the corresponding alpha, beta-unsaturated enone, (qqqq) producing a compound of formulae I–VIII, which contains an isoxazoline, by treatment of a beta-hydroxy oxime with a dehydrating reagent, (rrrr) producing a compound of formulae I–VIII, which contains an beta-hydroxy carbonyl, by treatment of a carbonyl with a base in the presence of another carbonyl moiety, (ssss) producing a compound of formulae I–VIII, which contains a cyclic imine, by treatment of an enone system with a glycine imine in the presence of base resulting in first Michael addition at the beta-carbon and subsequent imine formation upon aqueous workup, (tttt) producing a compound of formulae I–VIII, which contains a substituted pyrrole, by treatment of an enone with a glycine imine in the presence of an appropriate catalyst to induce a 1,3-dipolar cycloaddition, (uuuu) producing a compound of formula I–VIII, which contains a beta-keto carboxylic acid, ester or amide, by decomposition with light or heat of an alpha diazoketone and (vvvv) producing a compound of formulae I–VIII which contains a ketone, a product of decarboxylation of a beta-keto carboxylic acid, by heating.

In process (a), suitable reagents for activation of an alcohol include acetic anhydride, trifluoromethanesulfonic anhydride (triflic anhydride), methanesulfonyl chloride (mesyl chloride), p-toluenesulfonyl chloride (tosyl chloride), trifluoroacetic anhydride, trifluoroacetyl chloride, methoxysulfonyl fluoride (magic methyl), o-nitrobenzenesulfonyl chloride, 1-methyl- 2-fluoropyridinium salt and the like.

The activation may be carried out in a solvent which does not adversely affect the reaction (e.g., diethylether, dichloromethane, tetrahydrofuran, chloroform or N,N-dimethylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, lutidine, picoline, 4-N,N-dimethylaminopyridine, etc.), quinoline, and the like, preferably in the presence of organic bases such as triethylamine or pyridine.

The activation may also be carried out using a starting material having an opposite configuration at a carbon center. In this situation, the following two additional steps are required to yield a starting material having an epimeric hydroxyl moiety, i.e. (1) the alcohol is oxidized to its corresponding ketone, (2) the obtained ketone is reduced under selective conditions. Both chiral centers having either [R]- or [S]-configuration can be obtained selectively and separately.

In process (b), suitable azide reagents include well-established alkali metal azides such as sodium or lithium azides ($NaN_3$ or $LiN_3$) in the presence or absence of crown ethers, more reactive tetraalkylammonium azides (Danishefski, S. J.; DeNinno, M. P.; Chen, S. H. *J. Am. Chem. Soc.* 1988, 110, 3929), a copper-assisted azide reaction (Yamamoto, Y.; Asao, N. *J. Org. Chem.* 1990, 55, 5303) and a hydrogen azide-mine system (Salto, S.; Yokoyama, H.; Ishikawa, T.; Niwa, N.; Moriwake, T. *Tetrahedron Lett.* 1991, 32,663; Saito, S.; Takahashi, N.; Ishikawa, T.; Moriwake, T. *Tetrahedron Lett.* 1991, 32,667). The azide displacement reaction may be carried out in a solvent which does not adversely affect the reaction (e.g. chloroform, dichloromethane, tetrahydrofuran, pyridine, dimethylsulfoxide, N,N-dimethylformamide, hexamethylphosphoramide, etc. or a mixture thereof). The reaction may be conducted above, at, or below ambient temperature.

In process (c), the reduction may be carried out catalytically using hydrogen. Suitable catalysts include, but are not limited to platinum catalysts (e.g. platinum oxide, platinum black), palladium catalysts (e.g. palladium oxide, palladium on charcoal, palladium black, palladium hydroxide on charcoal, palladium on calcium carbonate poisoned with lead, palladium on barium carbonate with quinoline), nickel catalysts (e.g. nickel oxide, Raney nickel), rhodium catalysts (e.g. rhodium on alumina). Reduction may also be carried out using metal reducing reagents (see Review; Scriven, E. F. V.; Turnbull, K. Chem Rev. 1988, 88, 321; Patai, S., Ed., "*The Chemistry of the Azido Group*," Interscience Publishers, New York, 1971; Scriven, E. F. V., Ed., "*Azides and Nitrenes Reactivity and Utility*," Academic Press, Inc., New York, 1984) such as sodium borohydride under phase-transfer conditions, borohydride supported on an ion exchange resin, lithium aluminum hydride and the like, furthermore, 1,3-propanedithiol-triethylamine method (Bayley, H.; Staudring, D. N.; Knowles, J. R. *Tetrahedron Left.* 1978, 3633), triphenylphosphine (Vaultier, M.; Knouzi, N.; Carrie, R. *Tetrahedron Lett.* 1983, 24, 763), and sodium tellurium hydride (Suzuki, H.; Takaoka, K. Chem Lett. 1984, 1733).

The reduction may be carried out in a solvent which does not adversely affect the reaction (e.g., alcohols, water, acetone, dichloromethane, tetrahydrofuran, pyridine or N,N-dimethylformamide or a mixture thereof). The reaction may be conducted above, at, or below ambient temperature.

In process (d), suitable N-acylations may be carded out using the methods of symmetric carboxylic acid anhydrides, carboxylic acid halides, mixed carbonic-carboxylic anhydrides, active esters (p-nitrophenylester, trichlorophenyl ester, pentafluorophenyl ester, N-hydroxysuccinimide, cyanoethyl and the like), and carboxylic acid with suitable condensing reagents such as DCC (N,N-dicyclohexylcarbodiimide and its related condensing agents), DCC-HOBt (N,N-dicyclohexylcarbodiimide-1-hydroxybenzotriazole), Woodward reagent K method, N,N-carbonyldiimidazole and phosphonium containing reagents (e.g. benzotriazolyloxytris[dimethylaminolphosphonium hexafluorophosphate, N,N-bis[2-oxo-3 -ox-azolidinyl]phosphorodiamidic chloride, diethylphosphorobromidate, diphenylphosphoryl azide, bromo tris[dimethylamino]phosphonium hexafluorophosphate, and the like). Suitable reagents for amide formation include, but are not limited to formyl derivatives, acetyl halides (chloroacetyl, trichloroacetyl, o-nitrophenylacetyl, o-nitrophenoxyacetyl, acetoacetyl, [N'-dithiobenzyloxycarbonylamino]acetyl and the like), and substituted propionyl derivatives (3-phenylpropionyl, isobutyryl, picolinoyl, and the like). Other groups may be found in volume 3 of *The Peptides* Gross, E. and Meinhofer, J. Academic Press, 1981 and *Protective Groups in Organic Synthesis* Greene, T. W. John Wiley & Sons, New York, Chapter 7, 1981. Typically used coupling conditions are described by Gross, E.; Meinhofer, J. "*The Peptides*" vol. 3, Academic Press, 1981. The N-acylation may be carried out in a solvent which does not adversely affect the reaction (e.g. acetone, dichloromethane, chloroform, tetrahydrofuran, N,N-dimethylformamide, dimethylsulfoxide, diethylether, and the like, or a mixture thereof). The reaction may be conducted above, at, or below ambient temperature.

In process (e), N-alkylations may be carried out using aldehydes or ketones-followed by reduction of the initially formed iminium ion {The following reagents can be used for the reduction; sodium cyanoborohydride-boron trifluoride or the reducing reagents cited in process (c)}, corresponding halides in the presence of bases listed in process (a), or lithium dialkyl cuprate (King, F. E.; King, T. J.; Muir. I. H. M. *J. Chem. Soc.* 1946, 5; Yamamoto, H.; Maruoka, K. *J. Org. Chem.* 1980, 45, 2739). Suitable reagents for N-alkylation include, but are not limited to benzyl halide, 3,4-dimethoxybenzyl halide, nitrobenzyl halide, di(p-methoxyphenyl)methyl halide, triphenylmethyl halide, and the like. Other groups may be found in volume 3 of *The Peptides,* Gross, E. and Meinhofer, J. Academic Press, 1981 and *Protective Groups in Organic Synthesis,* Greene, T. W. John Wiley & Sons, New York, Chapter 7, 1981. The N-alkylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (f), urea formation may be carried out from the following reactions; reaction with silicon tetraisocyanate or silicon tetraisothiocyanate (Neville, R. G.; McGee, J. J. *Can. J. Chem.* 1963, 41, 2123), reaction with N,N-carbonyldiimidazole or N,N-thiocarbonyldiimidazole, followed by N-substituted primary or secondary amines or ammonia (Staab, H. A.; Wendel, K. *Org. Synth.* 1968, 48, 44), and reaction with phosgene or thiophosgene in the presence of ten-amine, followed by N-substituted primary or secondary amines or ammonia. The ureido formation may be earned out in a solvent which does not adversely affect the reaction (e.g. acetone, toluene, dichloromethane, tetrahydrofuran, pyridine, N,N-dimethylformamide, etc. or a mixture thereof). The reaction may be conducted above, at, or below ambient temperature.

In process (g), N-sulfonylation may be carried out using substituted sulfonylhalides in the presence of suitable tert-amines such as trialkylamine, pyridine, and the like (Remers, W. A.; Roth, R. H.; Gibs, G. J.; Weiss, M. J. *J. Org. Chem.* 1971, 36, 1232). Suitable reagents include, but are not limited to benzenesulfonyl halide, p-methyoxybenzenesulfonyl halide, 2,4,6-trimethylbenzenesulfonyl halide, toluenesulfonyl halide, benzylsulfonyl halide, p-methoxybenzylsulfonyl halide, trifluoromethylsulfonyl halide, phenacylsulfonyl halide, and the like. Some other representative groups may be found in volume 3 of *The Peptides,* Gross, E. and Meinhofer, J. Academic Press, 1981 and *Protective Groups in Organic Synthesis*, Greene, T. W. John Wiley & Sons, New. York. Chapter 7, 1981. The N-aryl- or alkylsulfonylation may be earned out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (h), N-carbamate formations may be carried out using common protecting groups for amino group such as, but not limited to methylcarbamates (cyclopropylmethyl, 9-fluorenylmethyl, and the like), substituted ethylcarbamates (2,2,2-trichloroethyl, 2-phosphonoethyl, 2-methylthioethyl, and the like), substituted propyl and isopropylcarbamates (1,1-dimethylpropynyl, 1-methyl- 1-(4-biphenylyl)ethyl, tert-butyl, phenyl, p-nitrobenzyl, 8-quinolyl, N-hydroxypiperidinyl, benzyl, di_methoxybenzyl, 9-anthrylmethyl, 1-adamantyl, cyclohexyl, tert-amyl, cinnamoyl, isobutyl, N'-p-phenylaminothiocarbonyl, N'-piperidinylcarbonyl, diphenylmethyl, and the like). Preparations of N-carbamates and other groups may be found in volume 3 of *The Peptides,* Gross, E. and Meinhofer, J. Academic Press, 1981 and *Protective Groups in Organic Synthesis,* Greene, T. W. John Wiley & Sons, New York, Chapter 7, 1981. The N-carbamate formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (i), N-guanidium formation may be carried out using several common reagents such as 1-guanyl-3,5-dimethylpyrazole (Salvadori, S.; Sarto, G. P.; Tomatis, R. *Eur. J. Med. Chem. Chim. Ther.* 1983, 18, 489), O-methylisourea (Van Nispen, J. W.; Tesser, G. I.; Nivard, R. J. F. *Int. J. Peptide Protein Res.* 1977, 9, 193), and thiourea sulfonylate (Maryanoff, C. A.; Stanzione, R. C.; Hampin, J. N.; Mills, J. E. *J. Org. Chem.* 1986, 51, 1882). The N-guanidinium formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (j), N-sulfenamides may be prepared from an amine and a sulfenyl halide (Davis, F. A.; Nadir, U. K. *Org. Prep. Proc. Int.* 1979, 11, 33; Kobayashi, T.; Iino, K.; Hiraoka, T. *J. Am. Chem. Soc.* 1977, 99, 5505; Zervas, L.; Borovas, D.; Gazis, E. *J. Am. Chem. Soc.* 1963, 85, 3660). Suitable reagents include, but are not limited to benzenesulfenyl halide, o-nitrobenzenesulfenyl halide, 2,4-dinitrosulfenyl halide, pentachlorobenzenesulfenyl halide, 2-nitro-4-methoxybenzenesulfenyl halide, triphenylmethylsulfenyl halide, and the like. Other groups may be found in volume 3 of *The Peptides,* Gross, E. and Meinhofer, J. Academic Press, 1981 and *Protective Groups in Organic Synthesis,* Greene, T. W. John Wiley & Sons, New York, Chapter 7, 1981. The N-sulfenylation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (k), suitable halogenation reagents include, but are not limited to triphenylphosphine with halogens (Verheyden, J. P. H.; Moffatt, J. G. *J. Am. Chem. Soc.* 1964, 86, 2093; Bergman, R. G. ibid., 1969, 91, 7405; Hrubiec, R. T.; Smith, M. B. *J. Org. Chem.,* 1983, 48, 3667), triphenylphosphine with cyanogen halides (Homer, L.; Oediger, H.; Hoffmann, H. Annalen Chem. 1959, 626, 26), triphenylphosphine with carbon tetrahalides (Hooz, J.; Gilani, S. S. H. *Can. J. Chem.* 1968, 46, 86; *Chem. Commun.* 1968, 1350), triphenylphosphine with NBS (N-bromosuccinimide)(Schweizer, E. E.; Creasy, W. S.; Light, K. K.; Shaffer, E. T. *J. Org. Chem.* 1969, 34, 212), and triphenylphosphine with hexachloroacetone (Magid, R. M.; Stanley-Fruchey, O.; Johnson, W. L. *Tetrahedron Lett.* 1977, 2999; Magnid, R. M.; Stanley-Fruchey, O.; Johnson, W. L.; Allen, T. G. *J. Org. Chem.* 1979, 44, 359). The halogenation may also be accomplished by other reagents such as mono- or tri-alkylsilyl halides with or without sodium halides (Olah, G. A.; Husain, A.; Singh, B. P.; Mehrota, A. K. *J. Org. Chem.* 1983, 48, 3667; Balme, G.; Fournet, G.; Gore, J. *Tetrahedron Lett.* 1986, 27, 1907), polymer bound trimethylsilyl derivatives (Cainelli, G.; Contento, M.; Manescalchi, F.; Plessi, L.; Panunzio, M. *Synthesis* 1983, 306; Imamoto, T.; Matsumoto, T.; Kusumoto, T.; Yokoyama, M. *Synthesis* 1983, 460), N,N-dichlorophosphoramidic dichloride (*Chem. Lett.* 1978, 923), phosphorus trihalide-zinc halide (Anderson, Jr. A. G.; Owen, N. E. T.; Freenor, F. J.; Erickson, D. *Synthesis* 1976, 398), diethylaminosulfur trifluoride (Middleton, W. J. *J. Org. Chem.* 1975, 40, 574), triphenoxyphosphonium alkyl halide (Rydon, H. N. *Org. Synth.* 1971, 51, 44; Verheyden, J. P. H.; Moffatt, J. G. *J. Org. Chem.* 1972, 37, 2289), and the like.

The halogenation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (l), phosphonic acid ester formation may be carried out using Michaelis-Arbuzov reactions (Bhattacharya, A. K.; Thyagarajan, G. *Chem. Rev.* 1981, 81, 415; Bauer, G.; Haegele, G. Angew. Chem. *Int. Ed. Engl.* 1977, 16, 477).

The phosphonic acid ester formation may be carried out in a solvent which does not adversely affect the reaction (e.g., acetone, dichloromethane, tetrahydrofuran, pyridine or N,N-dimethylformamide or a mixture thereof). The reaction may be conducted above, at, or below ambient temperature.

In process (m), phosphorylation may be carried out using, but is not limited to the 2-halo-2-oxo-1,3,2-dioxaphospholane-triethylamine reaction (Chandrakumar, N. S.; Hajdu, J. *J. Org. Chem.* 1983, 48, 1197). The phosphorylation may be carried out in a solvent which does not adversely affect the reaction (e.g., benzene, toluene, acetone, dichloromethane, tetrahydrofuran or N,N-dimethylformamide or a mixture thereof). Further, the reaction is preferably conducted in the presence of organic or inorganic bases, as described in process (a), preferably in the presence of organic bases such as triethylamine, pyridine etc. The reaction may be conducted above, at, or below ambient temperature, more preferably from 0° to 50° C.

In process (n), thioether formation may be carried out using, but is not limited to aryl- or akylmercaptan in the presence of suitable tert-amines such as trialkylamine, pyridine, and the like. The reaction may also be carried out by a metal-catalyzed thioether formation (Guindon, Y; Frenette, R; Fortin, R.; Rokach, J. *J. Org. Chem.* 1983, 48, 1357), alkali metal salts of aryl- or alkylmercaptans with a compound of formulae I-VIII which contains CH—OR group (OR is the leaving group). The alkali metal may be selected from sodium, potassium, lithium, and cesium. The thioether formation may be carried out in a solvent which does not adversely affect the reaction (e.g. acetone, dichloromethane, tetrahydrofuran, pyridine. N,N-dimethylformamide, etc. or a mixture thereof). The reaction may be conducted above, at, or below ambient temperature.

In process (o), aryl- or alkyloxythiocarbonylation may be carried out using aryl- or alkyloxythiocarbonylchloride or corresponding halides in the presence of suitable tert-amines such as trialkylamine, pyridine, and the like. The aryl- or alkylthiocarbonylation may be carried out in a solvent which does not adversely affect the reaction (e.g. acetone, dichloromethane, tetrahydrofuran, pyridine, N,N-dimethylformamide etc. or a mixture thereof). The reaction may be conducted above, at, or below ambient temperature.

In process (p), ether formation may be carried out using, but is not limited to aryl-, arylalkyl-, or alkylhalides in the presence of KY-zeolite (Onaka, M.; Kawai, M.; Izumi, Y. *Chem. Lett.* 1983, 1101), polymeric materials (Kimura, Y.; Kirszensztejn, P.; Regen, S. L. *J. Org. Chem.* 1983, 48, 385), nickel-catalysis (Camps, F.; Coil, J.; Moreto, J. M. *Synthesis* 1982, 186; Yamashita. *Synthesis* 1977, 803), arylalkyl-O-p-toluenesulfonate (Dewick, P. M. *Synth. Commun.* 1981, 11, 853), potassium or sodium alkoxides (Bates, R. B.; Janda, K. D. *J. Org. Chem.* 1982, 47, 4374), pyridine or other bases (*Chem. Lett.* 1978, 57), tetraalkylammonium halide (Miller, J. M.; So, K. H.; Clark, J. H. *Can. J. Chem.* 1979, 1887), mercury perchlorate (McKillop, A.; Ford, M. E. *Tetrahedron* 1974, 30, 2467), or a phase transfer catalyst (McKillop, A.; Fiaud, J. -C.; Hug, R. P. *Tetrahedon* 1974, 30, 1379). The ether formation may also be carried out with dialkyl- or diarylphosphoric acid in the presence of p-toluenesulfonic acid (Kashman, Y. *J. Org. Chem.* 1972, 37, 912), or with diazo compounds with tin(II) chloride (Christensen, L. F.; Broom, A.D. *J. Org. Chem.* 1972, 37, 3398). The ether formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

More specifically, O-alkylation may be carried out using bromoacetic acid derivatives, iodoacetic acid derivatives, a trifluoromethanesulfonyloxy acetic acid derivatives and the like in the presence of an appropriate base such as methylamine. The reaction is performed in an inert solvent such as N,N-dimethylformamide or dichloromethane preferably between −50° C. and 80° C. Alternatively, alkylation can be earned out using alkyl diazoacetates in the presence of a metal catalyst, for example Rh(OAc)$_2$ in an inert solvent such as dichioromethane preferably between −20° C. and 80° C.

In process (q), N-cyclic imide formations may be carried out using phthalic anhydride (Sasaki, T.; Minamoto, K.; Itoh, H. *J. Org. Chem.* 1978, 43, 2320), o-methoxycarbonylbenzoyl chloride with trialkylamine (Hoogwater, D. A.; Reinhoudt, D. N.; Lie, T. S.; Gunneweg, J. J.; Beyerman, H. C. *Recl. Trav. Chim. Pays-Bas.* 1973, 92, 819), or N-ethoxycarbonylphthalimide (Nefkens, G. H. L.; Tesser, G. I.; Nivard, R. J. F. *Recl. Trav. Chim. Pays-Bas.* 1960, 79, 688). Other groups and reagents may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-cyclic imide formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (r), N-phosphinamide formation may be carried out using, but is not limited to phosphinyl chloride with N-methylmorpholine (Kenner, G. W.; Moore, G. A.; Ramage, R. *Tetrahedron Lett.* 1976, 3623). Suitable reagents include, but are not limited to diphenylphosphinyl chloride, dimethyl- or diphenylthiophosphinyl chloride, dibenzyl- or diphenylphosphinyl chloride. Other groups and conditions may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-phosphinamide formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (s), N-phosphoramide formation may be carried out using, but is not limited to diphenylphosphoryl chloride with a tert-amine-base (Adams, E.; Davis, N. C.; Smith, E. L. *J. Biol Chem.* 1952, 199, 845), and triethylbenzylammonium chloride (Zwierzak, A. *Synthesis* 1975, 507; Zwierzak, A.; Piotrowicz, J. B. *Angew. Chem. Int. Ed. Engl.* 1977, 16, 107). Suitable reagents include, but are not limited to diphenylphosphoryl chloride, dimethyl- or diphenylthiophosphoryl chloride, dibenzyl- or diphenylphosphoryl chloride. Other groups and conditions may be found in volume 3 of *The Peptides*, Gross, E. and Meinhofer, J. Academic Press, 1981 and *Protective Groups in Organic Synthesis*, Greene, T. W. John Wiley & Sons, New York, Chapter 7, 1981. The N-phosphinamide formation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (t), deoxygenation may be carried out using, but is not limited to phenoxythiocarbonyl derivative with tributyltin hydride and 2,2-azobis-2-methylpropionitrile (AIBN) (Robins, M. J.; Wilson, J. S.; Hansske. F. J. Am. Chem. Soc. 1983, 105, 4059; Barton, D. H. R.; McCombie, S. W. *J. Chem. Soc., Perkin Trans.* 1 1975, 1574), or a phenyldithiocarbonyl derivative with tributyltin hydride and AIBN (Hayashi, T.; Iwaoka, T.; Takeda, N.; Ohki, E. *Chem. Pharm. Bull.* 1978, 26, 1786). The deoxygenation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (u), suitable oxidizing reagents include activated dialkyl sulfoxides (e.g. dimethylsulfoxide, methylethylsulfoxide) (Mancuso, A. J.; Swern, D. *Synthesis* 1981, 165), organo chromates [e.g. pyridinium chlorochromate (Corey, E. J.; Suggs, J. W. *Tetrahedron Lett.* 1975, 2647; Corey, E. J.; Boger, D. L. *Tetrahedron Lett.* 1978, 2461), pyridinium dichromate (Corey, E. J.; Schmidt, G. *Tetrahedron Lett.* 1979, 5, 399), Collins reagent (Collins, J. C.; Hess, W. W.; Frank, F. J. *Tetrahedron Lett.* 1968, 3363)], tetrapropylammonium perruthenate (Griffith, W. P.; Ley, S. V.; Whitcombe, G. P.; White, A. D. *Chem. Commun.* 1987, 1625; Griffith, W. P. *Aldrichimica Acta.* 1990, 23, 13), and the like. The oxidation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (v), suitable alkylating reagents include, but are not limited to aldehydes and ketones in the presence of reducing agents (Hrubowchak, D. M.; Smith, F. X. *Tetrahedron Lett.* 1983, 24, 4951), alkyl-, aryl, or arylalkyl halides (Shono, T.; Kashimura, S.; Sawamura, M.; Soejima, T. *J. Org. Chem.* 1988, 53, 907). In the case that the reaction is conducted in the presence of an organic or inorganic bases such as an alkaline earth metal (e.g. calcium, balium, magnesium, thallium etc.), an alkali metal hydride (e.g. sodium hydride, lithium hydride, etc.), an alkali metal hydroxide (e.g. sodium hydroxide, potassium hydroxide, etc.), an alkali metal carbonate (e.g. sodium carbonate, potassium carbonate, etc.), an alkali metal hydrogen carbonate (e.g. sodium hydrogen carbonate, potassium hydrogen carbonate, etc.), an alkali metal alkoxide (e.g. sodium methoxide, sodium ethoxide, thallium ethoxide, potassium tert-butoxide, etc.), an alkali metal alkanoic acid (e.g. sodium acetate, etc.), a trialkylamine (e.g. triethylamine, trimethylamine, etc.), or a pyridine compound (e.g. pyridine, lutidine, picoline, 4-N,N-dimethylaminopyridine, etc.), quinoline, and the like. The alkylation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (w), suitable halogenation reagents include, but are not limited to halogens treated by irradiation (sun lamp)

for several hours (Heffner, R.; Safaryn, J. E.; Joullie, M. M.; *Tetrahedron Lett.* 1987, 28, 6539) or oxalyl chloride (Evans, D. A.; Dow, R. L.; Shih, T. L.; Takecs, J. M.; Zahler, R. *J. Am. Chem. Soc.* 1990, 112, 5290). The halogenation may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (x), suitable oxidation reagents include, but are not limited to oxodiperoxymolybdenum(pyridine)-1,3-dimethyl-3,4,5,6-tetrahydro-2(1H)-pyrimidinone (Anderson, J. C.; Smith, S.C. SYNLETT 1990, 2, 107) and oxodiperoxymolybdenum(pyridine)-hexamethylphosphoramide (Vedejs, E. *J. Am. Chem. Soc.* 1974, 96, 5944; Vedejs, E.; Engler, D. A.; Telschow, J. E. *J. Org. Chem.* 1978, 43, 188). The oxidation may be carded out in a solvent which does not adversely affect the reaction (e.g. acetone, dichloromethane, tetrahydrofuran, pyridine, N,N-dimethylformamide, etc., or a mixture thereof). The reaction may be conducted above, at, or below ambient temperature.

In process (z), a compound of formulae I–VIII may be treated with a diazotization reagent. Suitable diazotization reagents include, but are not limited to azidotris(diethylamino)phosphonium bromide (McGuiness, M.; Shechter, H. *Tetrahedron Lett.* 1990, 31, 4987), p-carboxybenzenesulfonyl azide (Hendrickson, R. G.; Wolf, W. A. *J. Org. Chem.* 1968, 33, 3610; Williams, M. A.; Miller, M. *J. Tetrahedron Lett.* 1990, 31, 1807), polymer bound p-toluenesulfonyl azide (Roush, W. R.; Feitler, D.; Rebek, J. *Tetrahedron Lett.* 1974, 1391), p-toluenesulfonyl azide (Regitz, M. Angew. Chem. 1967, 79, 786), 2 -azo-3-ethylbenzthiazolium tetrafluoroborate (Balli, H.; Kersting, F. *Justus Liebigs Ann. Chem.*, 1961 647, 1. Balli, H.; Low, R. Tetrahedron Lett. 1966, 5821), N,N-dimethylazidochloromethyleniminium chloride (Kokel, B.; Viehe, H. G. *Angew. Chem. Int. Ed. Engl.* 1980, 19, 716; Kokel, B.; Boussouira, N. *J. Heterocyclic Chem.* 1987, 24, 1493), and mesyl azide (Danheiser, R. L.; Miller, R. F.; Brisbois, R. G.; Park, S. Z. *J. Org. Chem.* 1990, 55, 1959). The diazotization may be carried out in a solvent which does not adversely affect the reaction (e.g. acetone, dichloromethane, tetrahydrofuran, pyridine, N,N-dimethylformamide, etc. or a mixture thereof). The reaction may be conducted above, at, or below ambient temperature.

In process (aa), suitable olefination reagents include, but are not limited to Wittig reagents (Maecker, M., Org. React. 1965, 14, 270; Johnson, A. W., "*Ylid Chemistry*," Academic Press, New York, 1966) and $CH_2I_2$—Zn—$TiCl_4$ [or $Ti(NEt_2)_4$] reagent (Hibino, J.; Okazoe, T.; Takai, K.; Nozaki, H. *Tetrahedron Lett.* 1985, 26, 5579; Okazoe, T.; Hibino, J.; Takai, K.; Nozaki, H. ibid. 1985, 26, 5581). The carbonyl olefination may be carded out in a solvent which does not adversely affect the reaction (e.g. acetone, dichloromethane, tetrahydrofuran, pyridine, N,N-dimethylformamide, etc., or a mixture thereof). The reaction may be conducted at room temperature.

In process (bb), suitable O-acylation reagents include, but are not limited to alkyl, aryl, or arylalkyl acyl halides (Lakhvich. F. A.; Khlebnicova, T. S.; Akhrem, A. A. *Synthesis* 1985, 8, 784). The O-acylation may be carried out in a solvent which does not adversely affect the reaction (e.g. acetone, dichloromethane, tetrahydrofuran, pyridine, N,N-dimethylformamide etc., or a mixture thereof). The reaction may be conducted above, at, or below ambient temperature.

In process (cc), suitable amination reagents include, but are not limited to amino acid derivatives and lower alkyl, aryl, or arylalkyl amines (Winkler, J. D.; Hershberger, P. M.; Springer, J. P. *Tetrahedron Lett.* 1986, 27, 5177). The reaction may be carried out in refluxing in benzene, toluene or a solvent which does not adversely affect the reaction (e.g. tetrahydrofuran, pyridine, N,N-dimethylformamide, etc., or a mixture thereof). The reaction may be conducted at room temperature.

In process (rid), the alkylidene formation may be carried out using, but is not limited to aldehydes and ketones with active methylene compounds. (Schonberg, A.; Singer, E. *Chem. Ber.* 1970, 103,387 1; Chatterjee, S. *J. Chem. Soc.* B, 1969, 725). The alkylidene formation may be carried out in a solvent which does not adversely affect the reaction (eg. acetone, dichloromethane, tetrahydrofuran, pyridine, N,N-dimethylformamide, etc., or a mixture thereof). The reaction may be conducted under cooling to heating.

In process (ee), L may be hydroxy, or a good leaving group (halogen, tosylate, mesylate or triflate, for example). When a precursor compound contains a C(OH)—$CH_2$—C=O group, the elimination of $H_2O$ may be carried out in a solvent which is inert under the reaction conditions (e.g. toluene) with a trace of acid (e.g. toluene sulfonic acid), at a temperature selected from 50° to 100° C. When the precursor compound contains a good leaving group, the elimination may be carried out in the presence of a base (e.g. triethyl amine or potassium carbonate), at a temperature selected from 0° to 100° C.

In process (ff), suitable aliamines include phenylene diamine and substituted 1,2-phenyl diamines, 2,3-diaminopyridine, 3,4-diaminopyridine, 4,5-diaminopyridazine, 4,5-diaminopyrimidine and their acid salts, preferably in the presence of tertiary amines (e.g. N-methylmorpholine). Suitable solvents include methanol, ethanol, propanol, acetonitrile, 2-butanone and N,N-dimethylformamide, and a reaction temperature selected from 50° to 100° C.

In process (gg), suitable reagents include sodium borohydride, zinc in acetic acid, sodium triacetoxyborohydride in acetic acid, lithium trialkoxyaluminum hydride in tetrahydrofuran, potassium or lithium tri-sec-butylborohydride in tetrahydrofuran, and borane/t-butylamine complex in a solvent such as methanol or ethanol. The reduction may be conducted at −70° C. to room temperature.

In process (hh), suitable 2-aminothiophenols include substituted 1,2-aminothiophenols, preferably in the presence of tertiary amine (e.g. N-methylmorpholine). Suitable solvents include methanol, ethanol and n-propanol; and the reaction may be conducted at a temperature selected from 50° to 100° C.

In process (ii), the reagent to be used in this reaction may include di(lower)alkyl sulfoxide (e.g. dimethyl sulfoxide, ethyl methyl sulfoxide, propyl methyl sulfoxide, isobutyl methyl sulfoxide, butyl methyl sulfoxide, isobutyl methyl sulfoxide, hexyl methyl sulfoxide, etc). This reaction is usually conducted in the presence of oxalyl chloride, acid chlorides, lower alkanoic anhydride such as acetic anhydride in a conventional solvent that does not adversely influence the reaction such as dichloromethane, acetone, ethyl acetate, tetrahydrofuran, pyridine, N,N-dimethylformamide, etc., followed by the addition of a tertiary amine (e.g. triethyl amine). The reaction may be conducted at −70° C. to room temperature.

In process (jj), the dithiols are lower alkyl dithiols (e.g. ethanedithiol, propanedithiol or butanedithiol) and 1,2-aryl dithiols (e.g. 1,2-benzenedithiol) in the presence of a Lewis acid (e.g. boron trifluoride etherate or lanthanum trichloride) in a conventional solvent that does not adversely influence the reaction such as dichloromethane, tetrahydrofuran or ether. The reaction may be conducted at −70° C. and room temperature.

In process (kk), suitable oxygen-substituted amines include hydroxyl amine, O-alkylhydroxyl amines, and O-arylalkyl hydroxyl amines, for example O-benzyl hydroxyl amine. Suitable solvents include those that do not adversely affect the reaction, for example ethanol or methanol. The reaction is preferably carried out with one equivalent of hydroxyl amine, and at a temperature of 25° to 100° C., more preferably at the reflux temperature of the solvent.

In process (ll), suitable hydrazines include alkylhydrazines (e.g. butylhydrazine), arylhydrazines (e.g. phenylhydrazine), acylhydrazines (e.g. acetylhydrazine), semicarbazides (e.g. t-butyloxycarbonyl hydrazine) and sulfonyl hydrazines (e.g. tosyl hydrazine) in a conventional solvent that does not adversely affect the reaction such as tetrahydrofuran, methanol or ethanol. The reaction may be conducted at 20° to 100° C.

In process (mm), 2-substitutions on the pyrimidine may be hydrogen, alkyl, aryl, hydroxyl, alkoxy, thiol, amino, alkylamino, arylamino, acylamino, carbamylamino, and sulphonylamino groups. The appropriate pyrimidine containing compounds may be prepared according to the methods described in *"The Chemistry of Heterocyclic Compounds, Vol. 16, supplement II*, Chapter II, pp 21–60", D. J. Brown, John Wiley & Sons, 1985.

In process (nn), the furan containing compounds may be prepared according to the method described by Paulissen, R., et. al. in *Tetrahedron Lett.* 1974, 607.

In process (oo), one equivalent of hydroxyl amine hydrochloride and tertiary amine (e.g. N-methylmorpholine) in a conventional solvent that does not adversely affect the reaction such as tetrahydrofuran, methanol, ethanol or isopropanol is used to prepare the compound. The reaction is conducted at 20° to 100° C.

In process (pp), the pyridine containing compounds may be prepared-according to the literature: Osman, A. N.; Ismail, M. M.; Barakat, M. A. *Rev. Roum. Chim.* 1986, 31, 615–624; Ried W.; Meyer, A., *Ber. Deutsch. Chem. Ges.* 1957, 90, 2841; Troschutz, R.; Troschultz, J.; Sollhuberkretzer, M. *Arch Pharm.* 1985, 318, 777–781.

In process (qq), a substituted 2-aminothiophenol, a 2-aminophenol or an aromatic 1,2-diamine is used in a conventional solvent that does not adversely affect the reaction such as tetrahydrofuran, ethanol, isopropanol, acetonitrile or N,N-dimethylformamide. The reaction may be conducted at 20° to 100° C.

In process (rr), the keto-substituted furan containing compound may be prepared according to the literature: Williams, P. H. et al, *J. Am. Chem. Soc.* 1960, 82, 4883; E. J. Corey et al., *Chem. Lett.* 1987, 223.

In process (ss), suitable 1-halo-2-nitroaromatics may be substituted 1-fluoro-2-nitrobenzene, o-fluoro-nitropyridines, or o-bromo-nitro-naphthalene, etc. The arylation may be carried out in a solvent which does not adversely affect the reaction (e.g. tetrahydrofuran, N,N-dimethylformamide, dimethoxyethane, diglyme, etc.).

The base used to generate the anion may be isopropyl magnesium chloride, lithium diisopropyl amine or sodium hydride. The reaction may be conducted at a temperature selected from −70° C. to 100° C.

In process (uu), a nitrile oxide may be formed either by oxidation of an aldoxime or dehydration of a nitro compound as described in the following references or literature cited therein: (1) Torssell, K. G. B. "Nitrile Oxides, Nitrones and Nitronates in Organic Synthesis"; VCH Publishers: New York, 1988, p 64; (2) Kim, J. N.; Ryu, E. K. *Synthetic Communications* 1990, 20, 1373; (3) Chow, Y. L.; Shy, Y. Y.; Bakker, B. H.; Pillay, K. S. *Heterocycles* 1989, 29, 2245.

The nitrile oxide is placed in the presence of an alpha,beta-unsaturated enone in an inert solvent to yield an 2-isoxazolines. Any isomers may subsequently be chomatographically separated.

In process (zz), an isoxazoline may be transformed to the corresponding beta-hydroxy ketone using but is not limited to molybenum hexacarbonyl in wet acetonitrile according to: Baraldi, P. G.; Barco, A.; Benetti, S.; Manfredini, S.; Simoni, D. *Synthesis* 1987, 276. Alternatively, $Ti^{3+}$ may be employed to attain N—O bond cleavage: Das, N. B.; Torssell, K. B. G. *Tetrahedron* 1983, 39, 2227. Additionally, Raney-nickel may also selectively cleave the N—O bond without reducing the imino functionality as described in the following reference and literature cited therein: Torssell, K. G. B. "Nitrile Oxides, Nitrones and Nitronates in Organic Synthesis"; VCH Publishers: New York, 1988, p 16 and 290. During the course of this transformation, a significant amount of dehydration occurs to produce alpha-beta unsaturated enones which may be separated from the beta-hydroxy ketones.

In process (eee), an aryl- or alkylsulfonyl hydrazone may be formed by treatment of a ketone with an aryl- or alkylsulfonyl hydrazide in the presence of an acid catalyst in a solvent suitable for the reaction such as methanol or ethanol at temperatures ranging from ambient to the reflux temperature of the solvent.

In process (fff), a benzilic acid rearrangement to yield an alpha-hydroxy acid may be initiated in a tricarbonyl system by treatment with a slight excess of a hydroxylic base in THF-water initially between 0° C. and room temperature. The temperature may be permitted to rise to room temperature during the course of the reaction. Other nucleophiles such as methanol are also for this type of transformation at temperatures from ambient to the reflux temperature.

In process (ggg), an alpha-hydroxy acid may be oxidatively cleaved by treatment with lead tetraacetate in an inert solvent (e.g. benzene) to form a ketone.

In process (hhh), an allylic alcohol may be produced by selective reduction of an alpha-beta unsaturated enone. This is accomplished with but not limited to sodium borohydride in the presence of cerium(III) chloride heptahydrate in a suitable solvent such as methanol at or near 0° C.

In process (iii), an epoxide may be produced on the central carbonyl of a tricarbonyl moiety by but not limited to excess diazomethane as described in: Fisher, M. J.; Chow, K.; Villalobos, A.; Danishefsky, S. J. *J. Org. Chem.* 1991, 56, 2900–2907.

In process (jjj), liberation of the ester to the acid may be achieved by the cleavage of a suitably substituted ester function. Such a functional group may be benzyl, 2,2,2-trichloroethyl, 9-fluorenylmethyl and the like. These are cleaved by methods well known to those skilled in the art.

In process (kkk), condensation of an amine with the acid may be performed using the mixed or symmetrical anhydride of said acid, or an ester of the acid, preferably activated, such as the ester derived from hydroxybenzotriazole, or the corresponding acylcyanide, acylimidazole, or acylazide of the aforementioned acid.

In process (lll), selective protection of the 32-hydroxyl moiety may be achieved using one of a variety of trialkylsilyl groups. This then leaves exposed a lone secondary alcohol on C-24 for selective inversion, which may be accomplished by activation of the 24-hydroxy as a mesylate, tosylate, etc., followed by inversion with a suitable nucleophile such as water, benzoic acid, formic acid, etc. On the other hand inversion of the unactivated 24-hydroxy group may be achieved using well described Mitsunobu conditions. Liberation of the silyl ether and inverted C-24 acylated hydroxy (if carboxylic acids are used as the nucleophile) is accomplished using methods well known to those skilled in the art. Alternatively, inversion may be accomplished without protection of the 32-hydroxyl group if ascomycin, FK506, or similar compounds are treated with diethylaminosulfur trifluoride (DAST) in an inert solvent such as methylene chloride.

In process (mmm), condensation of an alkyloxy or substituted alklyoxy carbonyl hydrazine with ascomycin, FK506, similar compounds, or a suitable derivative thereof wherein the C-22 is available as a reactive center, including but not limited to a carbonyl, is performed in an inert solvent such as methanol, ethanol, 2-propanol, etc., in the presence of a catalyst which may be an acid such as formic acid, p-toluenesulfonic acid, or camphorsulfonic acid.

In process (nnn), acylation at C-33 of 32-oxo-ascomycin or a suitable derivative thereof can be achieved, but is not limited to the process outlined in Danheiser, R. L.; Miller, R. F.; Brisbois, R. G.; Park, S. Z. *J. Org. Chem.* 1990, 55, 1959–1964.

In process (ooo), diazotization at C-33 of 32-oxo-ascomycin or a suitable derivative thereof can be achieved, but is not limited to the process outlined in Danheiser, R. L.; Miller, R. F.; Brisbois, R. G.; Park, S. Z. *J. Org. Chem.* 1990, 55, 1959–1964.

In process (ppp), L may be a hydroxyl group, or a good leaving group (halogen, tosylate, nitrobenzenesulfonate, mesylate or rotate, for example).

The condensation may be carried out in a solvent which does not adversely affect the reaction (e.g. isopropanol, acetonitrile, dioxane, N,N-dimethylformamide, tetrahydrofuran, etc.). The reaction may be carried out in the presence of base (e.g. methylamine, 4-methylmorpholine or magnesium carbonate, etc.), at a temperature selected from 0° to 100° C. The appropriate thiazole containing compound may be prepared according to *Hantzsch's synthesis* described by: Katritzky, A. R.; Rees, C. W. "Comprehensive Heterocyclic Chemistry"; Pergamon Press: Oxford, 1984, Vol. 6, Part 4B, p.294–299.

In process (qqq), L may be a hydroxyl group, or a good leaving group (halogen, tosylate, nitrobenzenesulfonate, mesylate or triflate, for example).

The condensation may be carried out in a solvent which does not adversely affect the reaction (e.g. isopropanol, t-butanol, acetonitrile, dioxane, N,N-dimethylformamide, tetrahydrofuran, etc.). The reaction may be earned out in the presence of base (e.g. triethylamine, 4-methylmorpholine, potassium carbonate or magnesium carbonate, etc.), at a temperature selected from 0° to 100° C.

Suitable amidines include formamidine, alkylamidines, alkylamidines and alkylisoureas. Suitable guanidines include N-arylguanidines, N-acylated guanidines and N-sulfonylated guanidines.

In process (rrr), L may be a hydroxyl group, or a good leaving group (halogen, tosylate, nitrobenzenesulfonate, mesylate or triflate, for example).

The condensation may be carried out in a solvent which does not adversely affect the reaction (e.g. isopropanol, t-butanol, acetonitrile, dioxane, N,N-dimethylformamide, tetrahydrofuran, etc.). The reaction may be carried out in the presence of a base (e.g., triethylamine, 4-methylmorpholine, potassium carbonate or magnesium carbonate), at a temperature selected from 0° to 100° C.

The amides are primary amides such as formamide, alkylacylamides and arylacylamides.

In process (sss), the organometallic reagent may be a Grignard reagent an alkyllithium, or an alkyllithium reagents.

The selective addition may be carried out m a solvent which does not adversely affect the reaction (e.g., hexanes, ether, tetrahydrofuran, dimethoxyethane or 2-methoxyethyl ether). The reaction may be carried out in the presence of cerium (fir) at a temperature selected from –100° C. to 0° C.

In process (m), the gamma amino alpha hydroxy carbonyl or a masked gamma amino alpha hydroxy carbonyl of a corresponding compound prepared by process (sss) may have substitutions (e.g. alkyl, aryl groups, etc.) at the alpha and/or beta positions. Furthermore, the amino group may have N-alkyl or aryl substitutions.

The condensation may be carried out in a solvent which does not adversely affect the reaction (e.g. isopropanol, t-butanol, acetonitrile, dioxane, N,N-dimethylformamide, tetrahydrofuran, etc.). The reaction may be carried out in the presence of a base (e.g. triethylamine, 4-methylmorpholine, potassium carbonate or magnesium carbonate, etc.), at a temperature selected from 0° to 100° C.

In process (uuu), the reaction is generally carried out in two steps: first the condensation of an alpha diketone or a masked alpha diketone with an 1,2-diaminoalkane gives a dihydropyrazine. Once the dihydropyrazine has been prepared, it may be oxidized by air in the presence of Pd/C, PtO$_2$ or other catalysts. Metal oxides (e.g. MnO$_2$ or CuO) may also be used for the aromatization.

The condensation and oxidation may be earned out in a solvent which does not adversely affect the reactions (e.g. isopropanol, acetonitrile, dioxane, benzene, toluene, etc.). The reaction may be carried out in the presence of drying agent such as magnesium sulfate or molecular sieves at a temperature selected from 0° C. to 100° C.

In process (vvv), a 1,5-dicarbonyl group or a masked 1,5-dicarbonyl group prepared by process (sss) may have substitutions (e.g. alkyl, aryl groups etc.) at the alpha and/or beta positions. The condensation may be carried out with anhydrous ammonia in a solvent which does not adversely affect the reactions (e.g. liquid ammonia, isopropanol, acetonitrile, dioxane, benzene, toluene, etc.). The reaction may be carried out at a temperature selected from –40° C. to 100° C.

In process (www), a 1,4-dicarbonyl group or a masked 1,4-dicarbonyl group prepared by process (sss) may have substitutions (e.g. alkyl, aryl groups, etc.) at the alpha position.

The condensation and oxidation may be carried out with anhydrous hydrazine in a solvent which does not adversely affect the reactions (e.g. isopropanol, acetonitrile, dioxane. benzene, toluene, etc.). The reaction may be carried out in the presence of a drying agent such as magnesium sulfate or molecular sieves at a temperature selected from 0° C. to 100° C.

In process (xxx), the thiocarbonate formation may be carried out in a solvent which does not adversely affect the reactions (e.g. toluene, acetone, methylene chloride, tetrahydrofuran or pyridine, etc.). The reaction may be carried out in the presence of a base such as triethylamine, pyridine, dimethylaminopyridine and sodium carbonate at a temperature selected from 0° C. to 100° C. The thiocarbonylating reagent may be 1,1'-thiocarbonyldiimidazole, 1,1'-thiocarbonylbis(2-pyridone), thiophosgene, or O-phenylthiochloroformate.

In process (yyy), the carbonate formation may be carried out in a solvent which does not adversely affect the reactions (e.g. toluene, acetone, butanone, methylene chloride, tetrahydrofuran or pyridine etc.). The reaction may be carried out in the presence of a base such as triethylamine, pyridine, dimethylaminopyridine and sodium carbonate at a temperature selected from 0° C. to 100° C.

The carbonylating reagent may be 1,1'-carbonyldimidazole, 1,1'-carbonylbis(2-pyridone), phosgene, triphosgene, ethyl chloroformate, ethyl trichloroacetate, or o-phenylchloroformate.

In process (zzz), the cyclic phosphonate formation may be carried out by fast reacting a diol from a selected compound with phosphorous trichloride followed by the addition of an appropriate alcohol and amine. The alcohol used may be an alkyl alcohol, or an aryl alcohol. The amine used may be primary or secondary. Alternatively, the cyclic phosphonate formation maybe carried out by directly reacting the diol from a corresponding compound with an appropriate alkoxyphophoryl dichloride.

The phosphonate formation may be carried out in a solvent which does not adversely affect the reactions (e.g. carbon tetrachloride, chloroform, methylene chloride, toluene, tetrahydrofuran, etc.). The reaction may be carried out in the presence of a base such as triethylamine, pyridine, dimethylaminopyridine, and sodium carbonate at a temperature selected from 0° C. to 100° C.

In process (aaaa), the reduction of thiocarbonate may be carried out in a solvent which does not adversely affect the reactions (e.g., toluene or tetrahydrofuran) at a temperature selected from 0° C. to 100° C.

The reducing agent used may be trimethylphosphite, triethylphosphite, trialkylphosphite or tri-n-butyltin hydride.

In process (bbbb), the reduction of a 1,2-dicarbonyl group of a corresponding compound may be carried out in a solvent which does not adversely affect the reactions (e.g., methanol, ethanol, ethanol, pyridine or N,N-dimethylformamide).

The reducing agents used may be tin amalgam, aluminum amalgam with hydrogen chloride in ethanol, or may be hydrogen sulfide in pyridine or N,N-dimethylformamide.

In process (cccc), the reduction and condensation of a 2-(o-nitrophenyl)-1,3-diketone of a corresponding compound may be carried in a solvent which does not adversely affect the reactions (e.g. ethanol, tetrahydrofuran, ethyl acetate or benzene, etc.).

The reducing agents used may be hydrogen gas over Pet/C, or Pt/C, zinc dust with ammonium chloride, zinc dust with hydrochloric acid at a temperature selected from 0° C. to 100° C.

In process (dddd), triazole formation may be carried out using, but is not limited to an azide derivative with suitable acetylene analogues include diethylacetylene dicarboxylate, dimethylacetylene dicarboxylate, methyl cyanoacetylenecarboxylate, and the likes. The reaction may be conducted above, or below ambient temperature, more preferably from 0° to 50° C.

In process (eeee), pyrrole formation may be carried out using, but is not limited to amine compounds with 1,4-dicarbonyl analogues, such as acetonylacetone, and the likes. Suitable solvents include methanol, ethanol, n-propanol, isopropanol, acetonitrile and N,N-dimethylformamide. The reaction may be conducted above, or below ambient temperature, more preferably from 50° to 100° C.

In process (ffff), suitable reagents for vicinal hydroxylation include osmium tetroxide, potassium permanganate, and iodine in conjunction with silver acetate. Osmium tetroxide is preferably used with a regenerating agent such as hydrogen peroxide, alkaline t-butyl hydroperoxide or N-methylmorpholine-N-oxide, and a solvent that does not adversely affect the reaction, for example diethyl ether or tetrahydrofuran. Potassium permanganate is preferably used in mild conditions, for example alkaline aqueous solution or suspensions. Co-solvents such as t-butanol or acetic acid may also be used. Iodine-silver acetate under 'wet' conditions yields ci-diols. Preferably, iodine is used in aqueous acetic acid in the presence of silver acetate. Iodine-silver acetate under 'dry' conditions yields trans-diols. Here, the initial reaction is carried out in the absence of water, and final hydrolysis yields the diol. In each case, the oxidation is preferably carried out at a temperature of 0° to 100° C.

Suitable reagents for the oxidative cleavage of the vicinal diol include lead tetraacetate, phenyliodoso acetate, periodic acid or sodium metaperiodate. Suitable solvents for the first two reagents include benzene and glacial acetic acid. The second two reagents are preferably used in aqueous solution. The reaction is preferably carried out at a temperature of 0° to 100° C.

In process (gggg), suitable reagents for the oxidation of an aldehyde of the corresponding compound may include silver oxide, chromic acid and potassium permanganate. In the presence of a variety of catalysts, oxygen may also be used in converting an aldehyde to a carboxylic acid of a corresponding compound. The catalysts may be palladium or platinum oxide. The air oxidation may be carried out in a solvent which does not adversely affect the reaction (e.g., ethanol, water, acetonitrile, aqueous acetone or pyridine) at a temperature of 0° to 100° C.

In process (hhhh), esters of a corresponding carboxylic acid may be prepared under neutral conditions at room temperature by the reaction of the carboxylic acid with alcohols in the presence of molar mounts of activating reagents such as triphenyl phosphine and diethyl azodicarboxylate, carbodiimides, N,N'-carbonyldiimidazole and 1-methyl-2-halopyridinium iodide. Esters may also be formed by reacting the corresponding carboxylic acid with diazoalkanes in a solvent which does not adversely affect the reaction (e.g., ether, tetrahydrofuran or methylene chloride) at a temperature of from 0° to 100° C.

In process (iiii), the cyclopropanation of the allyl group of a corresponding compound may be carried out with diazoalkanes in a solvent which does not adversely affect the reaction (e.g., ether, methylene chloride or tetrahydrofuran) in the presence of a catalyst such as palladium (ID acetate. The temperature of the reaction is of −15° to 5° C.

In process (jjjj), a pyrrole ring may be produced by reacting a 1,4-dicarbonyl group of a corresponding compound with ammonia, or a substituted amine such as benzylamine or 2-aminoethanol. Suitable solvents include those which do not adversely affect the reaction (e.g., methylene chloride, tetrahydrofuran or dioxane). The reaction is preferably carried out at a temperature of 0° to 100° C.

In process (kkkk), the cyclization of a 1,4-dicarbonyl group of a corresponding compound may be carded out in the presence of a catalytic amount of acid (e.g., acetic acid or arylsulfonic acid). The reaction may be carried out in a solvent which does not adversely affect the reaction (e.g., methylene chloride, ether, benzene or toluene). The reaction is preferably carried out at a temperature of 0° to 60° C.

In process (llll), suitable reagents include air, a palladium (II) halide (e.g. palladium (II) chloride), in conjunction with a cuprous halide (e.g. cupper (I) chloride). Suitable solvents include those that do not adversely affect the reaction (e.g. DMF and water). The reaction is preferably carried out at a temperature of 0° to 100° C.

In process (mmmm), the ketone of the alpha-methoxy cyclohexanone in a corresponding compound may be first converted to its oxime derivative with hydroxylamine. The derivatization is preferably carried out in a solvent which does not adversely affect the reaction (e.g., ethanol, isopropanol or tetrahydrofuran) at a temperature of 0° to 100° C.

The hydroxyl group of the oxime (=N—OH) may then be converted to a good leaving group (=N—OL) by reacting with an alkylsulfonyl chloride (e.g., methanesulfonyl chloride or trifluoromethanesulfonyl chloride), an arylsulfonyl chloride (e.g., benzenesulfonyl chloride or toluenesulfonyl chloride), a carboxylic acid anhydride (e.g., trifluoroacetic anhydride). phosphorous pentachloride, thionyl chloride or N-methyl 2-fluoropyridinium iodide. The activation of oxime is preferably carried out in a solvent that does not adversely affect the reaction (e.g., tetrahydrofuran or methylene chloride) at a temperature of –20° to 50° C.

The activated oxime of a corresponding compound may then be fragmented in a protic solvent such as ethanol or lower alkyl alcohol at a temperature of 0° to 100° C.

Alternatively, in process (mmmm), the Beckmann fragmentation may be carried out by reacting the alpha-methoxycyclohexanone directly with an o-alkylsulfonyl hydroxylamine or an o-arylsulfonyl hydroxylamine. The reaction may be carded out in a protic solvent (e.g., ethanol, propanol or benzyl alcohol) at a temperature of 0° to 100° C.

In process (nnnn), suitable reducing agents include but are not limited to sodium cyanoborohydride, lithium aluminum hydride, borane-pyridine, or hydrogen in the presence of such catalysts as Raney nickel, platinum, platinum oxide, or palladium. An acidic environment may promote the reduction in some cases, and acids such as hydrochloric acid or p-toluenesulfonic acid may be added for this purpose. The reduction may be carned out in a solvent which does not adversely affect the reaction (e.g. ethanol, ethyl acetate).

In process (oooo), reduction of an oxime to the corresponding amine may be accomplished with but not limited to hydrogenation with a suitable catalyst such as palladium on carbon in a solvent inert to the reaction conditions (e.g. ethanol) at temperatures ranging from 0° to 100° C.

In process (pppp), reduction of an enone to the corresponding saturated ketone may be accomplished with but not limited to hydrogenation with a suitable catalyst such as either palladium on carbon or rhodium on alumina in a solvent inert to the reaction conditions (e.g. methanol, ethanol, isopropanol, ethyl acetate) in a temperature range from –78° to 100° C.

In process (qqqq), isoxazoline formation is accomplished by but not limited to the following sets of reaction conditions involving a beta-hydroxy oxime. One possible method is to treat the beta-hydroxy oxime with Martin's sulfurane dehydrating reagent at or near room temperature in a solvent inert to the reaction conditions such as methylene chloride. Alternatively, the beta-hydroxy oxime may be treated with p-toluenesulfonyl chloride in a solvent such as pyridine at temperatures ranging from 0° to 100° C.

In process (rrrr), an intramolecular aldol reaction is may be accomplished by but is not limited to treatment of a carbonyl with a base such as potassium or sodium hydride in a solvent which is inert to the reaction conditions (e.g. tetrahydrofuran or N,N-dimethylformamide) at a temperature range from –78° to 150° C.

In process (ssss), a cyclic imine may be formed by but is not limited to treatment of an alpha,beta-unsaturated enone with the sodium enolate of a glycine ester imine in an inert solvent such as tetrahydrofuran in a temperature range from –78° to 100° C. Upon aqueous workup, the imine hydrolyzes and spontaneously cyclizes to form the cyclic imine.

In process (tilt), a substituted pyrrole may be formed by but is not limited to a 1,3-dipolar cycloaddition between an alpha,beta-unsaturated enone with a glycine ester imine in the presence of a suitable catalyst such as lithium bromide and triethylamine in a solvent inert to the reaction conditions (e.g. tetrahydrofuran) at or near room temperature.

In process (uuuu), alpha diazoketones can be decomposed by exposure to UV light or by heating. Wolff rearrangements often ensue yielding beta-keto carboxylic acids when run in a solvent mixture containing water, beta-keto esters when run in a solvent containing an alcohol, or beta-keto amides when run in a solvent containing ammonia, a primary or a secondary amine. Moreover, if a beta-keto carboxylic acid is formed, decarboxylation can occur spontaneously or by heating.

The compounds and processes of the present invention will be better understood in connection with the following examples, which are intended as an illustration of and not a limitation upon the scope of the invention. Both below and throughout the specification, it is intended that any cited literature source is expressly incorporated by reference. Also, in certain examples, reference is made to compounds of formulae I–VII in which X is a group having the formula

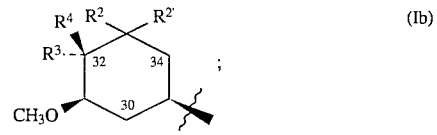

these are synthetic intermediates useful in the preparation of the compounds of the invention. In such intermediates, $R^2$ and $R^{2'}$ are each hydrogen, and $R^3$ and $R^4$ are as specified.

Example 7: Formula III: R=ethyl: R'=H: n=1; $R^{31}$=H: $R^{32}$=H: $R^{33}$=OH: $R^{34}$=H: $R^{35}$ and $R^{36}$ taken together form an oxime.=$NR^{38}$where $R^{38}$=hydroxyl.

Ascomycin (1.187 g, 1.5 mmol) was dissolved in 30 mL of ethanol. After pyridine (1.215 mL, 15 mmol) and hydroxylamine hydrochloride (1.043 g, 15 mmol) were added to the reaction mixture, it was gently refluxed for 4 hours. Ethanol was removed by evaporation, and 50 mL of chloroform was added to the residue. The chloroform layer was washed with water, 10%-$KHSO_4$, water and dried over anhydrous magnesium sulfate. Evaporation to dryness yielded 1.175 g of the tide compound. This was recrystallized from ethyl acetate (8 mL)-hexane (25 mL) to obtain 889 mg. MS (FAB) m/z: M+K=845, M+H=807; IR(KBr) 3440, 2950, 2920, 2870, 2820, 1740, 1705, 1645, 1450, 1375, 1350, 1330, 1280, 1260, 1230, 1195, 1170, 1160, 1100, 1090, 1045, 1035, 1010 $cm^{-1}$.

Examples 8a and 8b: Formula I: R=ethyl: R'=H: n=1; $R^1$=tert-butyldimethylsilyloxy (R Configuration) and Formula V: R=ethyl: R'=H: n=1; $R^1$=tert-butyldimethylsilyloxy: $R^{31}$=H; $R^{32}$=H: $R^{33}$ and $R^{34}$ taken together form an oxo group: $R^{35}$and $R^{36}$ taken together form an oxo group.

Example 8a: Ascomycin (1.582 g, 2 mmol) was dissolved in 30 mL of methylene chloride, and tert-butyldimethylsilyl chloride (362 mg, 2.4 mmol) and imidazole (272 mg, 4 mmol) were added. It was then stirred at room temperature for 4 days. Saturated aqueous ammonium chloride solution (20 mL) was added, and the product was extracted with ethyl acetate (25 mL×3). The ethyl acetate layers were combined, washed with brine, dried over anhydrous magnesium sulfate, faltered and evaporated to dryness to yield 2.11 g of title compound.

Example 8b: To a −78° C. solution of oxalyl chloride (96 mL, 1.1 mmol) in 5 mL of methylene chloride was added a solution of dimethylsulfoxide (156 mL, 2.2 mmol) in 4 mL of methylene chloride and the mixture was stirred at −78° C. After 30 min a solution of example 8a (453 mg, 0.5 mmol) in 5 mL of methylene chloride was added. The reaction was carried out at −78° C. for 1.5 hours with stirring and then triethylamine (696.9 mL, 5 mmol) was added. After stirring at −78° C. for 5 min, the mixture was then allowed to stand at room temperature for 30 min. The reaction mixture was partitioned between 40 mL of ethylacetate and 10 mL of 10%-KHSO$_4$ solution. The separated organic layer was washed with 10%-KHSO4 (3×), brine, and dried over anhydrous magnesium sulfate. Evaporation of the solvent gave 438 mg of the crude title compound. This was purified by silica gel column chromatography, eluting with 2.5% ethyl acetate in chloroform. Yield: 225.8 mg. MS (FAB) m/z: M+K=942; IR(KBr) 3500, 3440, 2950, 2935, 2880, 2860, 2820, 1740, 1720, 1650, 1630, 1580, 1460, 1445, 1380, 1360, 1325, 1280, 1250, 1220, 1195, 1170, 1135, 1105, 1090, 1040, 1030, 1005 cm$^{-1}$.

Example 12: Formula III: R=ethyl: R'=H: n=1; $R^{31}$=H: $R^{32}$=H: $R^{33}$ and $R^{34}$ taken together form an oxo group: $R^{35}$ and $R^{36}$ taken together form an oxo group To a solution of acetonitrile (5 mL) and 48% hydrofluoric acid (100 uL) was added Example 8b (530 mg, 0.586 mmol) in acetonitrile (7 mL) dropwise, and the mixture was stirred at room temperature for 35 min. Ethyl acetate (60 mL) was added to the reaction mixture, and the organic layer was washed with brine, 10%-NaHCO$_3$, brine, and dried over anhydrous magnesium sulfate. Evaporation of the solvent gave 515 mg of crude title compound which was purified by silica gel column chromatography, eluting with 1%-methanol in chloroform. 304.8 mg of pure compound was obtained. MS (FAB) m/z.: M+K=828; IR(KBr) 3420, 2960, 2930, 2870, 2820, 1740, 1720, 1645, 1620, 1580, 1450, 1380, 1345, 1325, 1280, 1260, 1245, 1220, 1195, 1170, 1140, 1115. 1100, 1090, 1050, 1035, 1010 cm$^{-1}$.

Examples 14a, and 14b: Formula V: R=ethyl: R'=H: n=1; $R^2$=H; $R^{2'}$=H: $R^3$ and $R^4$ taken together form an oxo group: $R^{31}$=H; $R^{32}$=H: $R^{33}$ and $R^{34}$ taken together form an oxo group; $R^{35}$ and $R^{36}$ taken together form an oxo group Example 14a: To a solution of oxalyl chloride (240 uL, 2.75 mmol), in methylene chloride (7 mL) was added dimethylsulfoxide (390 uL, 5.5 mmol) over 5 min at −78° C. The reaction mixture was aged for 30 min at −78° C. Ascomycin (988.8 mg, 1.25 mmol) in methylene chloride (8 mL) was added dropwise and stirred at −78° C. for 1.5 hours. Triethylamine (1.74 mL, 12.5 mmol) was carefully added and the mixture was stirred at −78° C. for an additional 5 min. It was then allowed to warm to room temperature for 30 min. Ethyl acetate (80 mL) was added to the reaction mixture, and the organic layer was washed with brine, 10%-KHSO$_4$, brine, 10%-NaHCO$_3$, brine and dried over anhydrous magnesium sulfate. Evaporation of the solvent yielded 920 mg of crude product. This was purified by silica gel column chromatography, eluting with 7%-ethyl acetate in chloroform. 648 mg of pure title compound was obtained. MS (FAB) m/z: M+K=826, M+H=788, M+H−H$_2$O=770; IR(KBr) 3420, 2960, 2930, 2870, 2820, 1725, 1645, 1625, 1450, 1380, 1340, 1325, 1280, 1260, 1245, 1220, 1195, 1170, 1130, 1115, 1100, 1090, 1040 cm$^{-1}$.

Example 14b: Formula I: R=ethyl; R'=H; n=1; $R^2$=H; $R^{2'}$=H; $R^3$ and $R^4$ taken together form an oxo group. (146 mg) was also isolated as a minor product from the above reaction. MS (FAB) m/z: M+K=828, IR(KBr) 3420, 2960, 2930, 2880, 2820, 1725, 1710, 1645, 1450, 1375, 1340, 1325, 1280, 1260, 1245, 1225, 1195, 1170, 1130, 1100, 1090, 1035. This compound was also produced by the procedure described in Example 48.

Example 15: Formula VI: R=ethyl: R'=H: n=1; $R^{21}$ and $R^{22}$ taken together form an oxime, =NR$^{38}$ where $R^{38}$=hydroxyl; $R^{23}$=OH: $R^{24}$=H: $R^{31}$=H: $R^{32}$=H: $R^{33}$=OH: $R^{34}$=H: $R^{35}$ and $R^{36}$ taken together form an oxime, =NR$^{38}$ where $R^{38}$=hydroxyl To a solution of ascomycin (4.748 g, 6 mmol) in ethanol (70 mL) were added hydroxylamine hydrochloride (4.172 g, 60 mmol) and pyridine (4.86 mL, 60 mmol). The mixture was then gently refluxed for 4 hours and kept at room temperature overnight with stirring. After treating the mixture as described in Example 7, the crude material (4.85 g) obtained was purified by silica gel column chromatography, eluting with 1.5% to 4%-methanol in chloroform. 184 mg of pure title compound was isolated. MS (FAB) m/z: M+K= 860, M+H=822; IR(KBr) 3420, 2960, 2930, 2870, 2820, 1745, 1640, 1450, 1390, 1375, 1350, 1325, 1280, 1265, 1220, 1195, 1170, 1160, 1140, 1100, 1090. 1050, 1040, 1015 cm$^{-1}$.

Example 20: Formula V: R=ethyl: R'=H: n=1; $R^3$ and $R^4$ taken together form an oxo group: $R^2$=H, $R^{2'}$=H: $R^{31}$ and $R^{32}$ taken together form a diazo group: $R^{33}$ and $R^{34}$ taken together form an oxo group; $R^{35}$ and $R^{36}$ taken together form an oxo group The title compound was prepared by the method described in R. L. Danheiser, R. F. Miller, R. G. Brisbois, S. Z. Park J. Org. Chem. 1990, 55, 1959–1964. Accordingly Example 14a (1.0 mmol) in acetonitrile (20 mL) containing water (18 uL), triethylamine (0.21 mL, 1.5 mmol), and methanesulfonyl azide (0.28 mL, 3.0 mmol) was stirred at ambient temperature for 6 hours, whereupon the volatiles were removed in vacuo. The residue was purified by chromatography on silica gel eluting with a mixture of hexanes and acetone (4:1) which provided the desired product (610 mg) in 75% yield. MS (FAB) m/z: M+K−N$_2$=824. IR (CDCl$_3$) 2115 cm$^{-1}$.

Example 23: Formula V: R=ethyl: R'=H: n=1; $R^1$=tert-butyldimethylsilyloxy; taken together with one of $R^{31}$ and $R^{32}$, one of $R^{33}$ and $R^{34}$ form a bond; one of $R^{31}$ and $R^{32}$ is H; one of $R^{33}$ and $R^{34}$ is C$_6$H$_5$CH$_2$ NH; $R^{35}$ and $R^{36}$ taken together form an oxo group The title compound is prepared by applying a general method described in the literature (Winkler, J. D.; Hershberger, P. M.; Springer, J. P. Tetrahedron Lett. 1986, 27, 5177). The product of Example 8b and a slight excess of benzylamine are dissolved in benzene and gently refluxed for 3–5 hours. The solvent is removed, and the residue obtained is purified by silica gel column chromatography to yield pure title compound.

Example 36: Formula III: R=ethyl: R'=H: n=1; $R^{31}$ and $R^{33}$ taken together form a bond; $R^{32}=R^{34}=H$: $R^{35}$ and $R^{36}$ taken together form an oxo group The title compound was prepared according to the methods described in the published European Patent Application No. 89192668 of Fisons, P.26, Example 11: mp 124°–125° C., MS (FAB) m/z: M+NH$_4$=791.

Example 37: Formula III: R=ethyl: R'=H: n=1; $R^{31}$=H; $R^{32}$=H; $R^{33}$=OH; $R^{34}$=H; $R^{35}$ and $R^{36}$ taken together form =N—OCH$_2$C$_6$H$_5$ A solution of ascomycin (0.791 g), O-benzylhydroxylamine hydrogen chloride (0.320 g) and dimethylaminopyridine (0.26 g) in absolute ethanol (10 mL) was refluxed under nitrogen overnight. After removal of solvent, the solid residue was purified by silica gel chromatography with ether elution. Yield: 0.6 g: 92°–98° C.; MS (FAB) m/z: M+H=897, M+NH$_4$=914.

Example 38: Formula VI: R=ethyl: R'=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{31}$ and $R^{33}$ taken together form a bond; $R^{32}$=H; $R^{34}$=H; $R^{35}$ and $R^{36}$ taken together form an oxo group; $R^{60}$=OH (R configuration): $R^{65}$=H A solution of the product of Example 36 (0.338 g), o-phenylenediamine (0.05 g) and N-methylmorpholine (0.04 g) in absolute ethanol was refluxed under nitrogen overnight. Solvent was removed in vacuo and the product purified by silica gel chromatography (10 g) with methylene chloride/acetonitrile (5:2, v/v) elution, followed by ether. Yield: 0.3 g; MS (FAB) m/z: M+H=846, M+NH$_4$=863.

Example 39: Formula II: R=ethyl: R'=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system: $R^{60}$=OH (R configuration); $R^{65}$=H A solution of ascomycin (0.41 g), o-phenylenediamine (0.108 g) and N-methylmorpholine (0.072 g) in absolute ethanol (3 mL) was refluxed under nitrogen overnight. Solvent was removed in vacuo and the product purified on silica gel (10 g) with methylene chloride/acetonitrile (5:2, v/v) elution, followed by 40% acetone in hexanes. Yield: 0.396 g; mp 110°–120° C.; MS (FAB) m/z: M+NH$_4$=881.

Example 40: Formula II: R=ethyl: R'=H; n=1; taken together with the carbon atoms to which they are attached, $R^{26}$, $R^{27}$, $R^{28}$ and $R^{29}$ form a 6',7'-dichlorquinoxaline with C-9 and C-10 becoming positions 2' and 3' of the heterocyclic system: $R^{60}$=OH (R configuration); $R^{65}$=H The title compound was prepared and purified by the procedure as described in Example 39 substituting 4,5-dichlorophenyl-1,2-diamine for o-phenylenediamine. mp: 107°–110° C.; MS (FAB) m/z: M+H=932, M+NH$_4$=949.

Example 41: Formula II: R=ethyl: R'=H; n=1; taken together with the carbon atoms to which they are attached. $R^{26}$, $R^{27}$, $R^{28}$ and $R^{29}$ form a 6',7'-dimethylquinoxaline with C-9 and C-10 becoming positions 2' and 3' of the heterocyclic system; $R^{60}$=OH (R configuration); $R^{66}$=H The title compound was prepared and purified by the procedure as described in Example 39 substituting 4,5-dimethylphenyl-1,2-diamine for o-phenylenediamine. mp: 112°–115° C.; MS (FAB) m/z: M+H=892, M+NH$_4$=909.

Examples 42a and 42b: Formula II: R=ethyl; R'=H; n=1; taken together with the carbon atoms to which they are attached, $R^{26}$, $R^{27}$, $R^{28}$ and $R^{29}$ form a 6'-methoxyquinoxaline with C-9 and C-10 becoming positions 2' and 3' of the heterocyclic system: $R^{60}$=OH (R configuration); $R^{65}$=H and Formula II: R=ethyl: R'=H: n=1; taken together with the carbon atom to which they are attached, $R^{26}$, $R^{27}$, $R^{28}$ and $R^{29}$ form a 7'-methoxyquinoxaline with C-9 and C-10 becoming positions 2' and 3' of the heterocyclic system; $R^{60}$=OH (R configuration); $R^{65}$=H The title compounds were prepared and purified by the procedure described in Example 39 substituting 4-methoxyphenyl-1,2-diamine for o-phenylenediamine. mp: 117°–126° C.; MS (FAB) m/z: M+H=894, M+NH$_4$=932.

Example 43: Formula II: R=ethyl: R'=H; n=1; taken together with the carbon atoms to which they are attached, $R^{26}$, $R^{27}$, $R^{28}$ and $R^{29}$ form a benzo[g]quinoxaline with C-9 and C-10 becoming positions 2' and 3' of the heterocyclic system: $R^{60}$=OH (R configuration); $R^{65}$=H The title compound was prepared and purified by the procedure as described in Example 39 substituting 2,3-naphthalenediamine for o-phenylenediamine. mp: 115°–120° C.; MS (FAB) m/z: M+H=914, M+NH$_4$=931.

Example 44: Formula II: R=ethyl: R'=H: n=1; taken together with the carbon atoms to which they are attached, $R^{26}$, $R^{27}$, $R^{28}$ and $R^{29}$ form a 6',7'-methylene-dioxy-quinoxaline with C-9 and C-10 becoming positions 2' and 3' of the heterocyclic system: $R^{60}$=OH (R configuration); $R^{65}$=H The title compound was prepared and purified by the procedure as described in Example 39 substituting 4,5-methylenedioxy-phenyl-1,2-diamine for o-phenylenediamine. mp: 190°–193° C.; MS (FAB) m/z: M+H=908, M+NH$_4$=946.

Example 45: Formula II: R=ethyl: R'=H: n=1; taken together with the carbon atoms to which they are attached, $R^{26}$, $R^{27}$, $R^{28}$ and $R^{29}$ form a 6',7'-difluoroquinoxaline with C-9 and C-10 becoming positions 2' and 3' of the heterocyclic system; $R^{60}$=OH (R configuration); $R^{65}$=H The title compound was prepared and purified by the procedure as described in Example 39 substituting 4,5-difluorophenyl-1,2-diamine for o-phenylenediamine. mp: 112°–116° C.; MS (FAB) m/z: M+K=938.

Example 46: Formula II: R=ethyl: R'=H: n=1; one of $R^{21}$ and $R^{22}$ is H and the other is OH; $R^{23}$=OH: $R^{24}$=H Zinc dust (5.4 g) was added portionwise into a stirred solution of ascomycin (5.4 g) in glacial acetic acid (50 mL) under nitrogen at room temperature. The reaction mixture was stirred vigorously at room temperature for 5 hours until TEC analysis (40% acetone in hexanes) showed the total disappearance of ascomycin. The solid was then filtered off and triturated with methylene chloride. The solvent was removed in vacuo and residue solid was redissolved in methylene chloride, filtered through silica gel eluting with 50% acetone in hexanes, and concentrated in vacuo. The solid was recrystallized from ether-hexanes. Yield: 4.9 g; mp 138°–140° C.; MS (FAB) m/z: M+$NH_4$=811.

Example 47: Formula III: R=ethyl; R'=H; n=1; $R^{31}$=H: $R^{32}$=H; $R^{33}$=H; $R^{34}$=S; $R^{35}$ and $R^{36}$ taken together is N, the S and N is bridged by a phenyl ring to form a benzothiazepine A solution of the product of Example 36 (0.26 g) and 2-aminothiophenol (0.05 g) and N-methylmorpholine (0.07 g) in absolute ethanol (3 mL) was refluxed under nitrogen overnight. Solvent was removed in vacuo, and the product was purified on silica gel with ether elution. Yield: 0.23 g; mp: 133°–138° C.; MS (FAB) m/z: M+H=881.

Example 48: Formula I: R=ethyl: R'=H: n=1; $R^2$=$R^{2'}$=H: $R^3$ and $R^4$ taken together form an oxo group Methylsulfide-chlorine complex was prepared by adding oxalyl chloride (0.32 g) into a stirred solution of dimethylsulfoxide (0.44 g) in methylene chloride (4 mL) and stirring at –70° C. for 0.5 hours. The solution of the complex was added in slow dropwise fashion into a stirring solution of ascomycin (1.6 g) in methylene chloride (5 mL) at –70° C. After stirring for 0.25 hours, triethylamine (1.4 g) was added at –70° C. Stirring was continued at –70° C. for 0.5 hours and then at room temperature for 1 hour. The reaction mixture was then diluted with ether (100 mL), washed with 1N HCl (aq) (2×30 mL), salted brine (30 mL), dried over magnesium sulfate and solvent removed. The product was purified on silica gel (70 g) with ether elution. Yield: 0.95 g; MS (FAB) m/z: M+H=790.

Example 50: Formula I: R=ethyl: R'=H: n=1; $R^2$=$R^{2'}$=H: $R^3$ and $R^4$ taken together form =N—OH A solution of the product of Example 48 (0.25 g), hydroxylamine hydrochloride (0.03 g) and N-methylmorpholine (0.035 g) in absolute ethanol was refluxed under nitrogen for 1.5 hours. Solvent was removed in vacuo and the product was purified on silica gel with ether elution. Yield: 0.2 g; MS (FAB) m/z: M+H=805.

Example 52: Formula III: R=ethyl; R'=H: n=1; $R^{31}$=H; taken together with the carbon atoms to which they are attached, $R^{33}$, $R^{34}$, $R^{35}$ and $R^{36}$ form a pyrrazole Hydrazine (0.014 g, in 2 mL of dry THF) was added into a stirred solution of the product of Example 12 (0.24 g) in dry THF (10 mL) at room temperature. After stirring at room temperature for 0.5 hours, the reaction mixture was refluxed for 2 hours. After removal of the solvent, the product was purified by silica gel chromatography (silica gel, 50 g) eluting with 50% acetone in hexanes. The solid was further purified by prep TLC (5% methanol in methylene chloride). Yield: 0.13 g; MS (FAB) m/z: M+H=786.

Example 53: Formula II: R=ethyl: R'=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system, two of the quinoxalines form a carbon-carbon bond between either the 6' or 7' on each heterocyclic system: $R^{60}$=OH (R configuration); $R^{65}$=H A solution of ascomycin (0.6 g), N-methylmorpholine (0.153 g) and 3,3'-diaminobenzidine tetrahydrochloride (0.1 g) in absolute ethanol was refluxed overnight The product was purified as described in Example 39. Yield: 0.31 g; mp: 128°–132° C.; MS (FAB) m/z: M+H=1725.

Example 54: Formula V: R=ethyl: R'=H: n=1; $R^1$=t-butyldimethylsilyloxy (R configuration); $R^{31}$=H; $R^{32}$=H; $R^{33}$=t-butyldimethylsilyloxy; $R^{34}$=H; $R^{35}$ and $R^{36}$ taken together form an oxo group Ascomycin (15 g) was dissolved in a solution of imidazole (3.75 g) in dry N,N-dimethylformamide (200 mL) and tert-butyldimethylchlorosilane (18.3 g) was added in portions and stirred at room temperature for 90 hours. N,N-dimethylformamide and excess tert-butyldimethylchlorosilane were removed by distillation (bath 30° C. at 0.8 torr). The solid residue was extracted with anhydrous ether (4×50 mL). Ether was removed in vacuo and the solid residue was purified by silica gel chromatography eluting with 5% acetone in hexanes providing the title compound (17 g). MS (FAB) m/z: M+H=1022.

Example 55: Formula VII: R=ethyl: R'=H: n=1; $R^1$=t-butyldimethylsilyloxy (R configuration); one of $R^{21}$ and $R^{22}$ is H and the other is OH; $R^{23}$=OH; $R^{24}$=H; $R^{31}$=$R^{32}$=H; $R^{33}$t-butyldimethylsilyloxy: $R^{34}$=H; $R^{35}$ and $R^{36}$ taken together form an oxo group Zinc dust (5 g) was added into a stirred solution of the product of Example 54 (5 g) in glacial acetic acid (25 mL) and stirred at room temperature for 5 hours. The reaction mixture was diluted with methylene chloride (150 mL) and the solid was filtered off and extracted with additional methylene chloride (3×50 mL). Solvent was removed in vacuo, and the solid residue filtered through silica gel (20 g) and eluted with ether. Yield: 5 g; MS (FAB) m/z: M+H=1024.

Example 56: Formula VII: R=ethyl: R'=H; n=1: $R^1$=t-butyldimethylsilyloxy (R configuration); one of $R^{21}$ and $R^{22}$ is H and the other is OAc; $R^{23}$=OH; $R^{24}$=H; $R^{31}$=$R^{32}$=H; $R^{33}$=t-butyldimethylsilyloxy; $R^{34}$=H; $R^{35}$ and $R^{36}$ taken together form an oxo group Acetic anhydride (1 mL) is added into a stirred solution of the product of Example 55 (1 g) and 4-dimethylaminopyridine (0.1 g) in dry pyridine (5 mL ). The reaction mixture is stirred at room temperature for 1 hour. Solvent and excess acetic anhydride is removed in vacuo (0.1 torr) and the solid residue is purified by silica gel chromatography eluting with 2% ethanol in methylene chloride.

Example 57: Formula V: R=ethyl: R'=H; n=1;
R$^1$=tri-isopropylsilyloxy (R configuration);
R$^{31}$=R$^{32}$=H; R$^{33}$=tri-isopropylsilyloxy; R$^{34}$=H; R$^{35}$
and R$^{36}$ taken together form an oxo group Triisopropylsilyl trifluoromethanesulfonate (10 g) in dry methylene chloride (25 mL) was added dropwise into a stirred solution of ascomycin (7.8 g) and N-methylmorpholine (4 g) in dry methylene chloride (100 mL) at 0° C. and stirred at 0° C. for 3 hours. Methanol (3 mL) was added and stirring was continued for an additional hour. Solvent was removed in vacuo and the residue worked up with ether and 1N hydrochloric acid. The organic phase was dried over magnesium sulfate and solvent removed in vacuo. Purification by silica gel chromatography eluting with 10% ether in hexanes provided the title compound (9 g). MS (FAB) m/z: M+Na=1128.

Example 58: Formula VII: R=ethyl; R'=H; n=1;
R$^1$=tri-isopropylsilyloxy (R configuration); one of R$^{21}$ and R$^{22}$ is H and the other is OH; R$^{23}$=OH;
R$^{24}$=H; R$^{31}$=R$^{32}$=H; R$^{33}$=tri-isopropylsilyloxy;
R$^{34}$=H; R$^{35}$ and R$^{36}$ taken together form an oxo group Zinc dust (5 g) was added into a stirred solution of the product of Example 57 (5 g) in glacial acetic acid (25 mL) and stirred at room temperature for 5 hours. The reaction mixture was diluted with methylene chloride (150 mL) and the solid was filtered off and extracted with methylene chloride (3×50 mL). The resulting solution was filtered through silica gel (20 g) and eluted with ether. Yield: 5 g; MS (FAB) m/z: M+Na=1130.

Example 59: Formula VII: R=ethyl; R'=H; n=1;
R$^1$=tri-isopropylsilyloxy (R configuration): one of R$^{21}$ and R$^{22}$ is H and the other is OAc; R$^{23}$=OH;
R$^{24}$=H; R$^{31}$=R$^{32}$=H; R$^{33}$=tri-isopropylsilyloxy;
R$^{34}$=H; R$^{35}$ and R$^{36}$ taken together form an oxo group Acetic anhydride (1 mL) was added into a stirred solution of the product of Example 58 (1 g) and 4-dimethylaminopyridine (0.1 g) in dry pyridine (5 mL). The reaction mixture was stirred at room temperature for 1 hour. Solvent and excess acetic anhydride was removed in vacuo (0.1 torr) and the solid residue was purified by silica gel chromatography eluting with 2% ethanol in methylene chloride. Yield: 1 g: MS (FAB) M+Na=1172.

Example 60: Formula II: R=ethyl; R'=H; n=1; one of R$^{21}$ and R$^{22}$ is H and the other is OAc;
R$^{23}$=OH; R$^{24}$=H 40% Aqueous hydrofluoric acid (0.5 mL, in 5 mL of acetonitrile) is added dropwise into a solution of the product of Example 59 (1.1 g) in acetonitrile (10 mL) at 0° C. The reaction mixture is stirred at room temperature for 2 hours. The reaction mixture is diluted with water (50 mL) and extracted with ethyl acetate (3×50 mL), dried over magnesium sulfate and the solvent removed in vacuo. The crude is purified by silica gel chromatography using 5% methanol in methylene chloride as eluent.

Example 61: Formula II: R=ethyl; R'=H: n=1;
taken together with the carbon atoms to which they are attached, R$^{26}$, R$^{27}$, R$^{28}$ and R$^{29}$ form a 2'-methyl-thiazole with C-9 and C-10 becoming positions 5' and 4' of the heterocyclic system:
R$^{60}$=OH (R configuration); R$^{65}$=H A solution of the product of Example 60 (0.83 g), thioacetamide (0.15 g) and triethylamine (0.2 g) in isopropanol (5 mL) is refluxed under nitrogen for 16 hours. Solvent is removed in vacuo and the solid residue is purified by silica gel chromatography eluting first with 20% acetonitrile in methylene chloride followed by 7% methanol in methylene chloride.

Example 62: Formula II: R=ethyl; R'=H: n=1;
taken together with the carbon atoms to which they are attached, R$^{26}$, R$^{27}$, R$^{28}$ and R$^{29}$ form a 2'-amino-thiazole with C-9 and C-10 becoming positions 5' and 4' of the heterocyclic system:
R$^{60}$OH (R configuration): R$^{65}$=H A solution of the product of Example 60 (0.1 g), thiourea (0.015 g) and methylmine (0.2 g) in acetonitrile (1 mL) is refluxed under nitrogen for 16 hours. Solvent is removed in vacuo and the solid residue is purified by silica gel chromatography eluting first with 20% acetonitrile in methylene chloride followed by 7% methanol in methylene chloride.

Example 63: Formula II: R=ethyl; R'=H: n=1;
taken together with the carbon atoms to which they are attached, R$^{26}$, R$^{27}$, R$^{28}$ and R$^{29}$ form a 2'-phenyl-imidazole with C-9 and C-10 becoming positions 5' and 4' of the heterocyclic system: R$^{60}$=OH (R configuration): R$^{65}$H A solution of the product of Example 60 (0.83 g). benzamidine hydrochloride hydrate (0.3 g) and triethylamine (0.2 g) in isopropyl alcohol (5 mL) is refluxed under nitrogen for 24 hours. Solvent is removed in vacuo, and the solid residue is purified by silica gel chromatography eluting with 10% methanol in methylene chloride.

Example 64: Formula II: R=ethyl; R'=H: n=1;
taken together with the carbon atoms to which they are attached, R$^{26}$, R$^{27}$, R$^{28}$ and R$^{29}$ form a 2'-phenyl-oxazole with C-9 and C-10 becoming positions 5' and 4' of the heterocyclic system;
R$^{60}$=OH (R configuration): R$^{65}$=H A solution of the product of Example 60 (0.83 , g), benzamide (0.25 g) and triethylamine (0.2 g) in acetonitrile (5 mL) is refluxed under nitrogen for 24 hours. Solvent is removed in vacuo and the solid residue is purified by silica gel chromatography eluting with 10% methanol in methylene chloride.

Example 65: Formula VII: R=ethyl; R'=H; n=1;
R$^1$=t-butyldimethylsilyloxy (R configuration); one of R$^{21}$ and R$^{22}$ is
[1-(2'2',5',5'-tetramethyl-2'5'-disila-1'-azolidinyl)]-2-ethyl and the other is OH; R$^{23}$=OH; R$^{24}$=H;
R$^{31}$=H; R$^{32}$=H; R$^{33}$=t-butyldimethylsilyloxyl;
R$^{34}$=H; R$^{35}$ and R$^{36}$ taken together form an oxo group To a solution of the product of Example 54 (1 g) in dry tetrahydrofuran (10 mL) is added with stirring at 0° C. 1-(2-ethyl)-2,2,5,5-tetramethyl-2,5-disila- 1-azacyclopentane magnesium bromide (1M in THF, 1.5 mL). The reaction mixture is allowed to reach room temperature and stir for 4 hours. The reaction mixture is worked up with saturated ammonium chloride (50 mL) and extracted with ethyl acetate (3×50 mL). The combined organic phase is washed with water, brine and dried over magnesium sulfate. The product is purified by silica gel chromatography eluting with 3% methanol in methylene chloride.

Example 66: Formula II: R=ethyl; R'=H: n=1; taken together with the carbon atoms to which they are attached, $R^{26}$, $R^{27}$, $R^{28}$ and $R^{29}$ form a pyrrole with C-9 and C-10 becoming positions 3' and 2' of the heterocyclic system; $R^{60}$=OH (R configuration); $R^{65}$=H 40% Aqueous hydrofluoric acid (1 mL) is added dropwise into a solution of the product of Example 65 (1.1 g) in acetonitrile (10 mL) at 0° C. The reaction mixture is stirred at room temperature for 2 hours. The reaction mixture is diluted with water (50 mL), extracted with ethyl acetate (3×50 mL), dried over magnesium sulfate and the solvent is removed in vacuo. The crude is purified by silica gel chromatography using 5% methanol in methylene chloride as eluent.

Example 67: Formula VII: R=ethyl; R'=H: n=1; $R^1$=t-butyldimethylsilyloxy (R configuration); taken together with the carbon atoms to which they are attached. $R^{26}$, $R^{27}$, $R^{28}$ and $R^{29}$ form a pyrazine with C-9 and C-10 becoming positions 2' and 3' of the heterocyclic system; $R^{33}$=t-butyldimethylsilyloxy; $R^{31}$=H; $R^{32}$=H; $R^{34}$=H; $R^{35}$ and $R^{36}$ taken together form an oxo group; $R^{60}$=OH (R configuration); $R^{65}$=H Activated manganese dioxide (1.1 g) is added into a solution of the product of Example 54 (1.1 g) and ethylenediamine (0.1 g) in dry benzene, and the suspension is stirred at 50° C. for 24 hours. The solid is filtered off, and solvent is removed in vacuo. The product is purified by silica gel chromatography eluting with 3% methanol in methylene chloride.

Example 68: Formula II: R=ethyl; R'=H: n=1; taken together with the carbon atoms to which they are attached, $R^{26}$, $R^{27}$, $R^{28}$ and $R^{29}$ form a pyrazine with C-9 and C-10 becoming positions 2' and 3' of the heterocyclic system; $R^{60}$=OH (R configuration); $R^{65}$=H The product of Example 67 is deprotected to give the title compound and purified according to the procedure of Example 60.

Example 69: Formula VII: R=ethyl; R'=H: n=1; $R^1$=t-butyldimethylsilyloxy (R configuration): one of $R^{21}$ and $R^{22}$ is [2,(1,3-dioxolanyl)]- 2-ethyl and the other is OH; $R^{23}$=OH; $R^{24}$=H; $R^{31}$=$R^{32}$=H; $R^{33}$=t-butyldimethylsilyloxy; $R^{34}$=H; $R^{35}$ and $R^{36}$ taken together form an oxo group To a solution of the product of Example 54 (t g) in dry tetrahydrofuran (10 mL) is added under stirring at 0° C. 2-(2-ethyl)-1,3-dioxolane magnesium bromide (1M in THF, 1.5 mL). The reaction mixture is allowed to reach room temperature and stir for 4 hours. The reaction mixture is worked up with saturated ammonium chloride (50 mL) and extracted with ethyl acetate (3×50 mL). The combined organic phases are washed with water, brine and dried over magnesium sulfate. The product is purified by silica gel chromatography eluting with 3% methanol in methylene chloride.

Example 70: Formula VII: R=ethyl; R'=H: n=1; $R^1$=t-butyldimethylsilyloxy (R configuration); taken together with the carbon atoms to which they are attached, $R^{26}$, $R^{27}$, $R^{28}$ and $R^{29}$ form a pyridine with C-9 and C-10 becoming positions 3' and 2' of the heterocyclic system; $R^{33}$=t-butyldimethylsilyloxy; $R^{31}$=H; $R^{32}$=H; $R^{34}$=H; $R^{35}$ and $R^{36}$ taken together form an oxo group; $R^{60}$=OH (R configuration); $R^{65}$=H A solution of the product of Example 69 (1 g), oxalic acid (0.2 g) and acetaldehyde (0.5 mL) in wet methylene chloride (5 mL) is stirred under nitrogen overnight. Solvent is removed in vacuo and the reaction crude is partitioned between ethyl acetate and aqueous sodium bicarbonate. The solution is dried over magnesium sulfate and the solvent is removed in vacuo. The residue is redissolved in isopropyl alcohol (5 mL) and ammonium hydroxide (0.5 mL) is added. The reaction mixture is allowed to stir at room temperature overnight. After removal of solvent in vacuo, the product is purified by silica gel chromatography eluting with 413% acetone in hexanes.

Example 71: Formula II: R=ethyl; R'=H: n=1; taken together with the carbon atoms to which they are attached, $R^{26}$, $R^{27}$, $R^{28}$ and $R^{29}$ form a pyridine with C-9 and C-10 becoming positions 3' and 2' of the heterocyclic system; $R^{60}$=OH (R configuration); $R^{60}$=H The product of Example 70 is deprotected and purified according to the procedure of Example 60 to give the title compound.

Example 72: Formula II: R=ethyl; R'=H: n=1; taken together with the carbon atoms to which they are attached, $R^{26}$, $R^{27}$, $R^{28}$ and $R^{29}$ form a pyridazine with C-9 and C-10 becoming positions 4' and 3' of the heterocyclic system; $R^{60}$=OH (R configuration); $R^{65}$=H A solution of the product of Example 69 (1 g), oxalic acid (0.2 g) and acetaldehyde (0.5 mL) in wet methylene chloride (5 mL) is stirred under nitrogen overnight. Solvent is removed and the reaction mixture is partitioned between ethyl acetate and aqueous sodium bicarbonate. After removal of the solvent the residue is redissolved in isopropyl alcohol (5 mL) and hydrazine (0.035 g) is added. The reaction mixture is allowed to stir at room temperature overnight. After removal of solvent, the bis-silylated product is purified by silica gel chromatography and is deprotected according to the procedure of Example 60.

Example 73: Formula II: R=ethyl; R'=H: n=1; taken together with the carbon atoms to which they are attached, $R^{26}$, $R^{27}$, $R^{28}$ and $R^{29}$ form a pyrazino[2,3-d]pyridazine with C-9 and C-10 becoming positions 2' and 3' of the heterocyclic system: $R^{60}$=OH (R configuration); $R^{65}$=H A solution of ascomycin (0.8 g), 4,5-diaminopyridazine (0.2 g) and N-methylmorpholine (0.2 g) in isopropyl alcohol (5 mL) is heated at 80° to 90° C. for 12 hours. Solvent is removed and product purified by silica gel chromatography eluting with 40% acetone in hexanes.

Examples 74a and 74b: Formula II: R=ethyl; R'=H: n=1; taken together with the carbon atoms to which they are attached, $R^{26}$, $R^{27}$, $R^{28}$ and $R^{29}$ form a pyrido[3,4-b]pyrazine with C-9 and C-10 becoming positions 2' and 3' of the heterocyclic system: $R^{60}$=OH (R configuration); $R^{65}$=H, and Formula II: R=ethyl; R'=H: n=1; taken together with the carbon atoms to which they are, attached, $R^{26}$, $R^{27}$, $R^{28}$, and $R^{29}$ form a pyrido[3,4-b]pyrazine with C-9 and C-10 becoming positions 3' and 2' of the heterocyclic system: $R^{60}$=OH (R configuration); $R^{65}$=H A solution of ascomycin (0.8 g), 4,5-diaminopyridine (0.2 g) and N-methylmorpholine (0.2 g) in isopropyl alcohol (5 mL) is heated at 80° to 90° C. for 12 hours. Solvent is removed, and the products purified by silica gel chromatography eluting with 10% acetone in hexanes.

Examples 75a and 75b: Formula II: R=ethyl; R'=H; n=1; taken together with the carbon atoms to which they are attached, $R^{26}$, $R^{27}$, $R^{28}$ and $R^{29}$ form a pyrido[2,3-b]pyrazine with C-9 and C-10 becoming positions 2' and 3' of the heterocyclic system; $R^{60}$=OH,(R configuration); $R^{65}$=H, and Formula II: R=ethyl; R'=H: n=1; taken together with the carbon atoms to which they are attached, $R^{26}$, $R^{27}$, $R^{28}$ and $R^{29}$ form a pyrido[2,3-b]pyrazine with C-9 and C-10 becoming positions 3' and 2' of the heterocyclic system; $R^{33}$=OH; $R^{31}$=H; $R^{60}$=OH (R configuration); $R^{65}$=H A solution of ascomycin (0.8 g), 2,3-diaminopyridine (0.2 g) and N-methylmorpholine (0.2 g) in isopropyl alcohol (5 mL) is heated at 80° to 90° C. for 12 hours. Solvent is removed, and the products are purified by silica gel chromatography eluting with 40% acetone in hexanes.

Examples 76a and 76b: Formula II: R=ethyl; R'=H; n=1; taken together with the carbon atoms to which they are attached, $R^{26}$, $R^{27}$, $R^{28}$ and $R^{29}$ form a pteridine with C-9 and C-10 becoming positions 7' and 6' of the heterocyclic system; $R^{60}$=OH (R configuration); $R^{65}$=H and Formula II: R=ethyl; R'=H: n=1; taken together with the carbon atoms to which they are attached, $R^{26}$, $R^{27}$, $R^{28}$ and $R^{29}$ form a pteridine with C-9 and C-10 becoming positions 6' and 7' of the heterocyclic system: $R^{60}$=OH (R configuration); $R^{65}$=H A solution of ascomycin (0.8 g), 4,5-diaminopyrimidine (0.2 g) and N-methylmorpholine (0.2 g) in isopropyl alcohol (5 mL) is heated at 80° to 90° C. for 12 hours. Solvent is removed and products purified by silica gel chromatography eluting with 20% methanol in methylene chloride.

Examples 96a and 96b: Formula III: R=ethyl; R'=H: n=1; $R^{31}$=$R^{34}$=H; taken together with the carbon atoms to which they are attached, $R^{32}$ and $R^{33}$ form a 3-phenyl-2-isoxazoline with C-23 and C-24 becoming positions 4' and 5' respectively of the heterocyclic system: $R^{35}$ and $R^{36}$ taken together form an oxo group; and Formula III; R=ethyl; R'=H; n=1; $R^{31}$=$R^{34}$=H; taken together with the carbon atoms to which they are attached, $R^{32}$ and $R^{33}$ form a 3-phenyl-2-isoxazoline with C-23 and C-24 becoming positions 5' and 4' respectively of the heterocyclic system: $R^{35}$ and $R^{36}$ taken together form an oxo group N-Chlorosuccinimide (2.67 g, 20 mmol) was suspended in chloroform (20 mL) with pyridine (0.1 mL). Benzaldehyde oxime (2.42 g, 20 mmol) was added to the suspension. Twenty minutes hence, the N-chlorosuccinimide had dissolved, and the resultant solution was stored under nitrogen. The product of Example 36 (1.006 g, 1.29 mmol) was dissolved in dry chloroform. The hydroxamic acid chloride solution (4 mL) prepared above was introduced, and the mixture was heated to 48° C. as triethylamine (0.4 mL) was slowly added. After 25 hours, the reaction mixture was cooled, and the volatiles were removed under reduced pressure. The crude material was purified by flash chromatography over silica gel (elution with hexanes:acetone 3:2) to supply the title compounds. Example 96a: IR (CDCl$_3$)cm$^{-1}$ 3420, 2950, 1780, 1750, 1720, 1340, 1160; $^1$H NMR (CDCl$_3$, 500 MHz) delta 7.70–7.35 (m, 5H), 5.38 (s, 1H) & 5.15 (d, J=7.7 Hz, 1H), 4.73 (dd, J=6, 10 Hz, 1H) & 4.64 (coupling obscured), 4.16 (d, J=7 Hz, 1H) & 4.13 (d, J=7 Hz, 1H); MS (FAB) m/z: M+K=931.

Example 96b: IR (CDCl$_3$) cm$^{-1}$ 2930, 1750, 1720, 1700, 1650, 1450, 1090; $^1$H NMR (CDCl$_3$, 500 MHz) delta 5.37 (d, J=7 Hz, 1H) & 5.23 (d, J=3 Hz, 1H), 5.18 (br s, 1H) & 4.89 (d, J=7.7 Hz, 1H), 4.30 (m, 1H) & 4.05 (m, 1H); MS (FAB) m/z: M+K=931.

Example 102: Formula III: R=ethyl: n=1; $R^1$=H; $R^{31}$=H; $R^{32}$=H; $R^{33}$=OH; $R^{34}$=H; $R^{35}$ and $R^{36}$ taken together is =N$R^{38}$; $R^{38}$-OCH$_2$COOH Ascomycin (300 mg, 0.4 mmol), carboxymethoxylamine hemi-hydrochloride (250 mg, 1.2 mmol) and pyridine (100 uL, 1.2 mmol) in ethanol 10 mL were refluxed for 4 hours. The solvent was evaporated, and the residue was taken up in EtOAc, washed sequentially with H$_2$O, dilute acid (0.2M H$_3$PO$_4$), and brine and dried over Na$_2$SO$_4$. Concentration under vacuum gave 430 mg of crude material which was purified by reverse phase-HPLC (21.4 mm ID×25 cm, C18, 8 μm silica, DYNAMAX preparative HPLC (Rainin)). Elution (15 mL/min) was performed with a linear gradient from 55:45 (H$_2$O—CH$_3$CN containing 0.1% TFA) to 10:90 over 30 min. Combination of selected fractions, evaporation of CH$_3$CN and lyophilization gave 124 mg of the title compound. MS (FAB) m/z: M+K=903.

Example 103a: Formula III: R=ethyl; n=1; R'=H; $R^{31}$=H; $R^{32}$=H; $R^{33}$=OH; $R^{34}$=H; $R^{35}$=OH (S-configuration); $R^{36}$=H To a solution of 48% aqueous HF (16 uL) in CH$_3$CN (1 mL) was added the product of Example 103c. below (S-isomer, 70 mg) in CH$_3$CN (1 mL). The mixture was stirred for 0.5 hours. The solvent was removed, and the crude material was purified by silica gel column chromatography using 2% MeOH/CH$_2$Cl2, yielding 48 mg of the title compound. MS (FAB) m/z: M+K 814.

Example 103b: Formula III: R=ethyl: n=1; R'=H; $R^{31}$=H; $R^{32}$=H; $R^{33}$=OH; $R^{34}$=H; $R^{35}$=H; $R^{36}$=OH (R-configuration)

The title compound was prepared using a procedure analogous to that of Example 103a, starting from the product of Example 103d. below.

Examples 103c and 103d: Formula V: R=ethyl; n=1; R'=H; R1=t-butyldimethylsilyloxy: $R^{31}$=H; $R^{32}$=H; $R^{33}$=OH; $R^{34}$=H; $R^{35}$=OH (S-configuration); $R^{36}$=H; and Formula V; R=ethyl: n=1; R'=H; R1=t-butyldimethylsilyloxy; $R^{31}$=H; $R^{32}$=H; $R^{33}$=OH; $R^{34}$=H; $R^{35}$=H; $R^{36}$=OH (R-configuration)

To a solution of the product of Example 8a (100 mg, 0.1 mmol) and sodium triacetoxyborohydride (25.7 mg, 0.11 mmol) in $CH_3CN$ (1 mL) at 0° C. was slowly added acetic acid (24 uL, 0.33 mmol). After stirring at 0° C. for 2 hours, the reaction mixture was quenched with water and stirred for an additional 0.5 hours. The solution was extracted with EtOAc, the organic phase was washed with $H_2O$, brine and dried over $Na_2SO_4$. Evaporation of the solvent gave 94 mg of the crude material which was chromatographed over silica gel using 20% EtOAc/CHCl$_3$ as an eluent. Unreacted starting material (10 mg), 18 mg of Example 103d, the silylated minor isomer (R), and 52 mg of Example 103c, the silylated major isomer (S), were collected.

Example 104a: Formula V: R=ethyl; n=1; R'=H; R1=t-butyldimethylsilyloxy; $R^{31}$=H; $R^{32}$=H; $R^{33}$=OH; $R^{34}$=H; $R^{35}$=OSi(Me2)-t-Bu (S-configuration); $R^{36}$=H To a solution of the product of Example 103c, below (1.0 g, 1.1 mmol) in $CH_2Cl_2$ (20 mL) was added t-butyldimethylsilyl chloride (730 mg, 4.84 mmol) and imidazole (660 mg, 9.68 mmol). This was stirred at room temperature for 5.5 hours. The reaction mixture was quenched with saturated $NH_4Cl$, and diluted with EtOAc. The organic phase was washed with saturated $NH_4Cl$, saturated $NaHCO_3$, brine and dried over $Na_2SO_4$. The solvent was evaporated and 1.32 g of the crude material was chromatographed over silica gel column to give 868 mg of disilylated product and 140 mg of the recovered starting material.

Example 104b: Formula V: R=ethyl; n=1; R'=H; R1=OSi(Me2)-t-Bu; $R^{31}$=H; $R^{32}$=H; $R^{33}$ and $R^{34}$ taken together form an oxo group: $R^{35}$=t-butyldimethylsilyloxy (S-configuration); $R^{36}$=H To a −78° C. solution of oxalyl chloride (40 uL, 0.44 mmol) in 1 mL of methylene chloride was added a solution of dimethylsulfoxide (60 ul, 0.88 mmol) in 1 mL of methylene chloride and the mixture was aged at −78° C. for 30 min. A solution of the disilylated product of Example 104a (170 mg, 0.2 mmol) in methylene chloride (1 mL) was added. The reaction was carried out at −78° C. for 3 hours with stirring and triethylamine (270 uL, 2.0 mmol) was added. After stirring at −78° C. for 20 min, it was then allowed to stand to room temperature for 30 min. The reaction mixture was partitioned between 40 mL of ethylacetate and 10 mL of 10%-NaHSO$_4$ solution. The organic layer was washed with 10%-NaHSO$_4$, water (×3), brine, and dried over anhydrous magnesium sulfate. Evaporation of the solvent gave 160 mg of the crude material.

Example 104c: Formula III: R=ethyl: n=1; R'=H; $R^{31}$=H; $R^{32}$=H; $R^{33}$ and $R^{34}$ taken together form an oxo group; $R^{35}$=OH (S-configuration); $R^{36}$=H Aqueous HF cleavage of the resultant product of Example 104b followed by silica gel column purification provided 85 mg of the title compound. MS (FAB) m/z.: M+K=830.

Example 105a: Formula II: R=allyl; R'=H: n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{60}$=OH (R configuration); $R^{65}$=H A solution of FK-506 (0.41 g), o-phenylenediamine (0.108 g) and N-methylmorpholine (0.072 g) in absolute ethanol (3 mL) is refluxed under nitrogen overnight Solvent is removed in vacuo and product is purified on silica gel (10 g) with methylene chloride/acetonitrile (5:2, v/v) elution, followed by 40% acetone in hexanes to give the desired compound.

Example 105b: Formula II: R=propyl; R'=H: n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system: $R^{60}$=OH (R configuration); $R^{65}$=H The product of Example 105a (150 mg) and 10% Pd/C (30 mg) in ethylacetate (6 ml) are hydrogenated at room temperature for 20 min at 1 atm. The catalyst is filtered, the solvent is concentrated, and the resulting crude material is purified by silica gel column chromatography (eluting solvent, chloroform/acetone 5:1) to give the title compound.

Example 150: Formula III: R=ethyl; R'=H: n=1; $R^{31}$=$R^{32}$=$R^{33}$=H; $R^{34}$=OH; $R^{35}$ and $R^{36}$ taken together form an oxo group To a solution of ascomycin (2 g, 2.53 mmol) in dichloromethane (13.3 mL) at −78° C. was added diethylamino sulfurtrifluoride (3.4 mL, 25.3 mmol) and the reaction was stirred for 20 min. The reaction mixture was added dropwise to ice water (~75 mL), extracted with ethyl acetate (2×100 mL), dried (Na$_2$SO$_4$), filtered, and concentrated in vacuo to give a yellow foam (2.21 g). The mixture was purified by silica gel chromatography to give the title compound (0.23 g). mp 100°–105° C.; IR (CDCl$_3$) 3590, 3470, 2930, 1745, 1720, 1690, 1645, 1450 cm$^{-1}$; $^{13}$C NMR (125 MHz) delta 9.3, 11.8, 14.3, 15.8, 16.3, 20.7, 21.0, 24.2, 24.4, 27.6, 27.6, 30.7, 31.2, 32.9, 32.9, 34.1, 34.7, 35.1, 39.1, 39.2, 41.8, 48.6, 55.7, 56.3, 56.3, 56.4, 56.9, 69.4, 73.6, 74.1, 74.3, 75.2, 75.3, 84.2, 96.9, 123.4, 128.0, 131.5, 140.4, 165.6, 169.4, 196.6, 213.3; MS (FAB) m/z: M+H=792, M+K=830. Anal. calc'd. for $C_{43}H_{69}NO_{12}$·0.6 hexane: C, 66.34; H, 9.25; N, 1.66. Found: C, 66.74; H, 8.88; N, 1.67.

Example 151: Formula III: R=ethyl; R'=H: n=1; $R^{31}$=$R^{32}$=$R^{34}$=H; $R^{33}$=OH; $R^{35}$ and $R^{36}$ taken together=NR$^{38}$; $R^{38}$=—NHC(O)OCH$_3$ Ascomycin (5.0 g), methylhydrazinocarboxylate (1.1 g), and p-toluenesulfonic acid monohydrate (1.2 g) in methanol (100 mL) were stirred at ambient temperature for 16 hours and concentrated to dryness. The mixture was purified by chromatography on silica gel eluting with hexane/acetone mixtures to give pure title compound (3.6 g). An analytical sample was recrystallized from methylene chloride and diethyl ether. mp 159°–164° C.; IR (CDCl$_3$) 3600, 3500, 3300, 2950, 1745, 1725, 1700, 1642, 1450cm$^{-1}$; $^{13}$C NMR (125 MHz) delta 10.2, 12.0, 14.7, 15.4, 15.7, 20.9, 21.2. 24.2, 26.9. 27.1, 28.0, 30.6, 31.1, 31.2, 32.1, 33.5, 34.6, 34.8, 34.9, 38.9, 41.1, 49.0, 49.1, 52.5, 56.2, 56.6. 56.8, 73.1, 73.5, 73.8, 73.9, 75.8, 76.0, 77.2, 84.1, 97.6, 126.3, 129.1, 132.6, 138.5, 155.7, 159.7, 165.0, 168.9, 196.5; MS (FAB) m/z: M+H=864, M+K=902. Anal. calc'd. for C$_{45}$H$_{73}$N$_3$O$_{13}$·2.0 H$_2$O: C, 60.05; H, 8.62; N, 4.67. Found: C, 60.17; H, 8.24; N, 4.55.

Example 152: Formula III: R=ethyl; R'=H: n=1; R$^{31}$=R$^{32}$=R$^{34}$=H; R$^{33}$=OH; R$^{35}$ and R$^{36}$ taken together=NR$^{38}$; R$^{38}$=—NHC(O)OCH$_2$CH$_3$ Example 151 is repeated using ascomycin and substituting ethylhydrazinocarboxylate for methylhydrazinocarboxylate to provide the title compound.

Example 153: Formula III: R=ethyl; R'=H: n=1; R$^{31}$=R$^{32}$=R$^{34}$H; R$^{33}$=OH; R$^{35}$ and R$^{36}$ taken together=NR$^{38}$; R$^{38}$=—NHC(O)OCH$_2$C$_6$H$_5$ Example 151 is repeated using ascomycin and substituting benzylhydrazinocarboxylate for methylhydrazinocarboxylate to provide the title compound.

Examples 157a and 157b: Formula III: R=ethyl; R'=R$^{31}$=H; n=1; taken together with the carbon atoms to which they are attached, R$^{32}$, R$^{33}$, R$^{34}$, R$^{35}$ and R$^{36}$ form an isoxazole ring with C-24 and C-22 becoming positions 5' and 3' of the isoxazole ring: and Formula III; R=ethyl; R'=H; n=1; R$^{31}$=H; taken together with the carbon atoms to which they are attached R$^{32}$, R$^{33}$, R$^{34}$, R$^{35}$ and R$^{36}$ form an isoxazole ring with C-24 and C-22 becoming positions 3' and 5' of the isoxazole ring A solution of the product of Example 12 (1 g), hydroxylamine hydrochloride (0.1 g) and N-methylmorpholine (0.14 g) in isopropanol was stirred at room temperature overnight, and then refluxed for 6 hours. The solvent was removed and the products were purified by silica gel chromatography eluting with 5% methanol in methylene chloride. Yield: 0.7 g; MS (FAB) m/z: M+K=825.

Example 158: Formula II: R=ethyl; R'=H; n=1; taken together with the carbon atoms to which they are attached, R$^{26}$, R$^{27}$, R$^{28}$ and R$^{29}$ form a 6',9'-diaza-benzo[g]quinoxaline with C-9 and C-10 becoming positions 2' and 3' of the heterocyclic system: R$^{60}$=OH (R configuration); R$^{65}$=H A solution of ascomycin (0.5 g). 1,2,4,5-tetraaminobenzene tetrahydrochloride (0.9 g) and N-methylmorpholine (1.4 mL) in absolute ethanol (11 mL) was refluxed overnight. The solvent was removed, and the intermediate product was purified by silica gel chromatogaphy. MS (FAB) m/z: M+K=932. The intermediate product (0.18 g) and glyoxal (40% in water, 0.06 g) in absolute ethanol (5 mL) was heated at 50° C. for 5 hours. After removal of solvent, the product was purified by silica gel chromatography eluting with 10% isopropanol in methylene chloride. Yield: 0.075 g; MS (FAB) m/z: M+NH$_4$=933.

Examples 159a, 159b and 159c: Formula V: R=allyl; R'=H; n=1; R$^2$=R$^{31}$=R$^{32}$=R$^{2'}$=H; R$^3$and R$^4$ taken together form an oxo group: R$^{33}$ and R$^{34}$ taken together form an oxo group: R$^{35}$ and R$^{36}$ taken together form an oxo group; Formula I: R=allyl; R'=H; n=1; R$^2$=R$^{2'}$=H; R$^3$ and R$^4$ taken together form an oxo group; and Formula III; R=allyl; R'=H: n=1; R$^{31}$=H; R$^{32}$=H; R$^{33}$ and R$^{34}$ taken together form an oxo group; R$^{35}$ and R$^{36}$ taken together form an oxo group FK-506 (2 g) was oxidized according to the procedure described in Example 48. The products were purified by silica gel chromatography eluting with 5% acetone in hexanes. Yield: Example 159a, 0.3 g; MS (FAB) m/z: M+K=838; Example 159b, 0.9 g; MS (FAB) m/z: M+K=840; Example 159c, 0.1 g; MS (FAB) m/z: M+H=840.

Example 160: Formula IV: R=ethyl; R'=H; n=1; R$^2$=R$^{24}$=R$^{2'}$=H; R$^3$ and R$^4$ taken together form an oxo group: one of R$^{21}$ and R$^{22}$ is H and the other is OH; R$^{23}$OH The title compound was prepared from the product of Example 48 according to the procedure described in Example 46. MS (FAB) m/z: M+H=792, M+K=830.

Example 161: Formula VII: R=ethyl; R'=H; n=1; R$^2$=; R$^3$ and R$^4$ taken together form an oxo group; one of R$^{21}$ and R$^{22}$ is H and the other is OH; R$^{23}$=OH; R$^{24}$=H; R$^{31}$=H; R$^{32}$=H; R$^{33}$and R$^{34}$ taken together form an oxo group: R$^{35}$ and R$^{36}$ taken together form an oxo group; R$^{2'}$=H The title compound was prepared from the product of Example 14 according to the procedure described in Example 46. MS (FAB) m/z: M+K=828.

Example 169: Formula III: R=ethyl; R'=H; n=1; R$^{31}$=benzyl; taken together with the carbon atoms to which they are attached, R$^{32}$, R$^{33}$, R$^{34}$, R$^{35}$ and R$^{36}$ form a pyrazole ring The title compound is prepared from the product of Example 16 and hydrazine according to the procedure of Example 52.

Example 170: Formula III: R=ethyl; R'=H; n=1; R$^{31}$=H; taken together with the carbon atoms to which they are attached, R$^{32}$, R$^{33}$, R$^{34}$, R$^{35}$ and R$^{36}$ form a N-methylpyrazole ring A solution of the product of Example 12 (0.5 g) and methylhydrazine (0.044 g) in absolute ethanol (10 mL) was refluxed under nitrogen for 4 hours. Solvent was removed in vacuo, and product (0.3 g) was purified by silica gel chromatography eluting with 2% methanol in dichloromethane. MS (FAB) m/z: M+H=800.

Example 171: Formula III: R=ethyl; R'=H; n=1; R$^{31}$=H; taken together with the carbon atoms to which they are attached, R$^{32}$, R$^{33}$, R$^{34}$, R$^{35}$ and R$^{36}$ form a N-ethylpyrazole ring A solution of Example 12, ethylhydrazine oxalate (0.144 g) and N-methylmorpholine (0.128 g) in absolute ethanol (10 mL) was refluxed under nitrogen. Solvent was removed in vacuo, and product (0.325 g) was purified by silica gel chromatography eluting with 2% methanol in dichloromethane. MS (FAB) m/z: M+H=814.

Example 172: Formula III: R=ethyl; R'=H; n=1; $R^{31}$=H; taken together with the carbon atoms to which they are attached, $R^{32}$, $R^{33}$, $R^{34}$, $R^{35}$ and $R^{36}$ form a N-(2'-hydroxyethy)pyrazole ring A solution of the product of Example 12 (0.5 g) and hydroxyethylhydrazine (0.0723 g) in absolute ethanol (10 mL) was refluxed under nitrogen. Solvent was removed in vacuo, and product (0.229 g) was purified by silica gel chromatography eluting with 3% methanol in dichloromethane. MS (FAB) m/z: M+H=830.

Example 173: Formula III: R=ethyl; R'=H; n=1; $R^{31}$=H; taken together with the carbon atoms to which they are attached. $R^{32}$, $R^{33}$, $R^{34}$, $R^{35}$ and $R^{36}$ form a N-phenylpyrazole ring A solution of the product of Example 12 (0.5 g) and phenylhydrazine (0.103 g) in absolute ethanol (10 mL) was refluxed under nitrogen. Solvent was removed in vacuo, and product (0.31 g) was purified by silica gel chromatography eluting with 3% methanol in dichloromethane. MS (FAB) m/z: M+H=862.

Example 174: Formula III: R=ethyl; R'=H; n=1; $R^1$=OH; $R^{23}$=OH; $R^{24}$=H; $R^{31}$=H; taken together with the carbon atoms to which they are attached, $R^{32}$, $R^{33}$, $R^{34}$, $R^{35}$ and $R^{36}$ form a N-benzylpyrazole ring A solution of the product of Example 12 (0.5 g). benzylhydrazine hydrochloride (0.23 g) and N-methylmorpholine (0.14 g) in absolute ethanol (10 mL ) was refluxed under nitrogen for 4 hours. Solvent was removed in vacuo, and product (0.28 g) was purified by silica gel chromatography eluting with 3% methanol in dichloromethane. MS (FAB) m/z: M+H=876.

Example 175: Formula III: R=ethyl; R'=H; n=1; $R^{31}$=H; taken together with the carbon atoms to which they are attached, $R^{32}$, $R^{33}$, $R^{34}$, $R^{35}$ and $R^{36}$ form a N-(2'-phenylethyl)pyrazole ring A solution of the product of Example 12 (0.5 g), 2-phenylethylhydrazine sulfate (0.234 g) and N-methylmorpholine (0.14 g) in absolute ethanol (10 mL) was refluxed under nitrogen for 4 hours. Solvent was removed in vacuo, and product was purified by silica gel chromatography eluting with 3% methanol in dichloromethane. Yield: 0.28 g, MS (FAB) m/z: M+H=890.

Example 176: Formula III: R=ethyl; R'=H; n=1; $R^{31}$H; taken together with the carbon atoms to which they are attached, $R^{32}$, $R^{33}$, $R^{34}$, $R^{35}$ and $R^{36}$ form a N-acetylpyrazole ring The title compound is prepared from the product of Example 12 and acetyl hydrazine according to the procedure of Example 52.

Example 178: Formula VII: R=ethyl; R'=H; n=1; $R^1$=triethylsilyloxy: taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{31}$=H; $R^{32}$=H; $R^{33}$=triethylsilyloxy; $R^{34}$=H; $R^{35}$ and $R^{36}$ taken together form an oxo group: $R^{60}$=OH (R configuration); $R^{65}$=H A solution of the bis-triethylsilylated compound derived in a fashion similar to that of Example 54 (1.0 g) and o-phenylenediamine (0.32 g) in absolute ethanol (7 mL) was refluxed for 4 hours. Solvent was removed in vacuo and product (1.0 g) was purified by silica gel chromatography eluting with 15% acetone in hexanes. MS (FAB) m/z: M+K=1130.

Example 179: Formula IV: R=ethyl; R'=H; n=1; $R^2$=H; $R^3$ and $R^4$ taken together form an oxo group; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{60}$ and $R^{65}$ taken together form an oxo group; $R^{2'}$=H To a solution of oxalyl chloride (0.0465 g) in dry methylene chloride (2 mL) at −70° C. was added dimethylsulfoxide (0.043 g). After stirring at −70° C. for 0.5 hours, a solution of the product of Example 178 (0.2 g) in methylene chloride (2 mL) was added, and the mixture was stirred for an additional 1.5 hours. Triethylamine (0.15 g) was added, and the cooling bath was removed. After stirring at room temperature for 0.5 hours, the reaction was partitioned between ether (30 mL) and water (10 mL), the organic phase was washed with 1N HCl (3×3 mL), dried over magnesium sulfate and solvent removed in vacuo. The crude intermediate was deprotected according to the procedure described in Example 167 to give the product: 0.15 g; MS (FAB) m/z: M+NH$_4$=877.

Example 180: Formula VII: R=ethyl; R'=H; n=1; $R^1$=t-butyldimethylsilyloxy (R configuration); taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system: $R^{31}$=H; $R^{32}$=H; $R^{33}$=t-butyldimethylsilyloxy: $R^{34}$=H; $R^{35}$ and $R^{36}$ taken together form an oxo group: $R^{60}$=OH (R configuration): $R^{65}$=H A solution of the product of Example 54 (2.0 g) and o-phenylenediamine (0.628 g) in absolute ethanol (15 mL) was refluxed for 6 hours, Solvent was removed in vacuo and product (1.8 g) was purified by silica gel chromatography eluting with 15% acetone in hexanes. MS (FAB) m/z: M+K=1130.

Example 181: Formula VII: R=ethyl; R'=H; n=1; $R^1$t-butyldimethylsilyloxy: taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{31}$=H; $R^{32}$=H; $R^{33}$t-butyldimethylsilyloxy: $R^{34}$=H; $R^{35}$ and $R^{36}$ taken together form an oxo group: $R^{60}$ and $R^{65}$ taken together form an oxo group The title compound was prepared from the product of Example 180 using the procedure described in Example 179. MS (FAB) m/z: M+H=1090; M+K=1128.

Example 182: Formula II: R=ethyl; R'=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system: $R^{60}$=OAc (R configuration); $R^{65}$=H To a stirred solution of the product of Example 180 (0.5 g) in dry pyridine (8 mL) containing catalytic amount of dimethylaminopyridine (15 mg) was added acetic anhydride (1.1 mL). After stirring at room temperature for 40 min., the reaction mixture was partitioned between ether and water. The organic phase was washed with 0.5N HCl and brine and dried over magnesium sulfate. Solvent was removed in vacuo to give the acetate as a white foam (0.51 g). 40% Aqueous HF (0.087 mL) in acetonitrile was added over 1 min to a stirred solution of this foam (0.51 g) in acetonitrile (8 mL). The reaction mixture was diluted with water after 0.5 hours at room temperature and extracted with ether. The organic phase was washed once with saturated sodium bicarbonate, dried over magnesium sulfate and solvent removed in vacuo. The product was purified by silica gel chromatography eluting with 20% acetone in methylene chloride. Yield: 0.33 g; MS (FAB) m/z M+H=906, M+K= 944.

Example 211: Formula VI: R=ethyl; R'=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{31}$=H; taken together with the carbon atoms to which they are attached, $R_{32}$, $R^{33}$, $R^{34}$, and $R^{35}$ form a pyrazole: $R^{60}$=OH (R configuration); $R^{65}$=H A solution of the product of Example 52 (0.785 g) and o-phenylenediamine (0.2 g) in absolute ethanol is refluxed under nitrogen overnight. After removal of solvent, the product is purified by silica gel chromatography.

Example 212: Formula VI: R=ethyl; R'=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{31}$=H; $R^{32}$=H; $R^{33}$and $R^{34}$ taken together is nitrogen. $R^{35}$ and $R^{36}$ taken together is nitrogen, the two nitrogens are bridged by a phenyl ring to form a benzodiazepine ring: $R^{60}$=OH (R configuration); $R^{65}$=H A solution of the product of Example 12 (0.8 g) and o-phenylendiamine (0.4 g) in absolute ethanol (10 mL) is refluxed under nitrogen overnight. After removal of solvent, the product is purified by silica gel chromatography.

Examples 213a and 213b: Formula III: R=ethyl; R'=H; n=1; $R^{31}$=H; $R^{36}$=O such that when taken together with $R^{32}$, $R^{33}$, $R^{34}$, $R^{35}$, and the carbon atoms to which they attached form a furan with a carboethoxy attached at the alpha position: and Formula III: R=ethyl: R'=H; n=1; $R^{31}$=H; $R^{33}$=O wuch that taken together with $R^{32}$, $R^{34}$, $R^{35}$, $R^{36}$ and the carbon atoms to which they attached form a furan with a carboethoxy attached at alpha position The title compounds are prepared from the product of Example 12, ethyl diazoacetate and rhodium acetate according to the methods described in the literature (Paulissen, R., et al, *Tetrahedron Lett.*, 1974, 607).

Examples 214a and 214b: Formula III: R=ethyl; R'=H; n=1; $R^{31}$, and $R^{33}$ taken together form a bond; taken together with the carbon atoms to which they are attached, $R^{34}$=O, and $R^{32}$ form a furan substituted with hydroxymethyl group at the alpha position: $R^{35}$ and $R^{36}$ taken together form an oxo group and Formula III: R=ethyl; R'=H; n=1; $R^{31}$ and $R^{35}$ taken together form a bond; taken together with the carbon atoms to which they are attached, $R^{36}$=O and whentaken together with $R^{32}$ forms a furan substituted with hydroxymethyl group at the alpha position: $R^{33}$ and $R^{34}$ taken together form an oxo group The title compounds are prepared from the product of Example 12 and epoxyacrolein according to the methods described in the literature (Williams, P. H., et al, *J. Am. Chem. Soc.* 1960, 82, 4883).

Example 215: Formula III: R=ethyl; R'=H; n=1; $R^{31}$=H; $R^{33}$=N; $R^{32}$ and $R^{34}$ taken together form a bond. $R^{35}$ and $R^{36}$ taken together=N, such that taken together with the carbon atoms to which they attached $R^{31}$, $R^{32}$, $R^{33}$, $R^{34}$, $R^{35}$, $R^{36}$ form a pyrimidine with a phenyl group attached at a position 2'

A solution of the product of Example 12 (0.8 g), benzamidine hydrochloride (0.4 g) and N-methylmorpholine (0.5 g) in isopropanol (10 mL) is refluxed for 2 hours. After removal of solvent, the product is partitioned between ethyl acetate and water. The organic phase is washed once with brine, dried over magnesium sulfate and the solvent is removed in vacuo. The product is purified by silica gel chromatography.

Example 216: Formula III: R=ethyl; R'=H; n=1; $R^{33}$and $R^{34}$ taken together form an oxo group; $R^{31}$=H; $R^{32}$=o-nitrophenyl; $R^{35}$ and $R^{36}$ taken together form an oxo group The title compound is prepared from the product of Example 12 and 1-fluoro-2-nitrobenzene according to the procedure described in Example 16.

Examples 217a and 217b: Formula III: R=ethyl; R'=H; n=1; $R^{31}$ and $R^{33}$ taken together form a bond: taken together with the carbon atoms to which they are attached, $R^{34}$=NH, and $R^{32}$ form an indole: $R^{35}$ and $R^{36}$ taken together form an oxo group: and Formula III: R=ethyl: R'=H; n=1; $R^{31}$ and $R^{35}$ taken together form a bond: taken together with the carbon atoms to which they are attached, $R^{36}$=NH, and $R^{32}$ form an indole; $R^{33}$ and $R^{34}$ taken together form an oxo group The product of Example 216 and a catalytic amount of 5% Pd/C in ethanol is stirred under 1 atm of hydrogen. The reaction is followed by TLC analysis. The catalyst is then filtered off, solvent removed and product purified by silica gel chromatography.

Examples 218a and 218b: Formula III: R=ethyl; R'=H; n=1; $R^{31}$=H; $R^{32}$ and $R^{35}$ form a bond; $R^{36}$=N, $R^{33}$ and $R^{34}$, taken together with the carbon atoms to which they attached form a pyridine with amino group at position 2' and cyano group at position 3'; and Formula III: R=ethyl; R'=H; n=1; $R^{31}$H; $R^{32}$ and $R^{34}$ form a bond: $R^{33}$=N, $R^{35}$, and $R^{36}$, taken together with the carbon atom to which they attached form a pyridine with amino group at position 2, and cyano group at position 3'

The title compounds are prepared from the product of Example 12 according to the methods described in the literature (Troschutz, R.; Troschutz, J.; Sollhuberkretzer, M. *Arch. Pharm.* 1985, 777–781).

Examples 224a and 224b: Formula III: R=ethyl; R'=H; n=1; $R^{31}$ and $R^{33}$ taken together form a bond; $R^{32}$=H; $R^{34}$=H; $R^{35}$=H and $R^{36}$=OH; and Formula III: R=ethyl; R'=H: n=1; $R^{31}$ and $R^{33}$ taken together form a bond; $R^{32}$=H; $R^{34}$=H; $R^{35}$=OH and $R^{36}$=H The product of example 36 (861 mg, 1.11 mmol) was dissolved in methanol (75 mL) to which was added $CeCl_3 \cdot 7 H_2O$ (456 mg, 1.22 mmol). The resultant mixture was chilled to 0° C., and sodium borohydride (46 mg, 1.22 mmol) was added portionwise. After 1 hour, the reaction was quenched by pouring the reaction mixture into 75 mL of water. This mixture was extracted with ether (2×50 mL). The combined organic extracts were dried over magnesium sulfate and freed of solvent. The isomeric allylic alcohols were purified and separated by silica gel chromatography using 25% acetone in hexane as eluent. Those fractions containing pure higher and lower Rf alcohols respectively were combined to furnish the less polar allylic alcohol (0.12 g) and the more polar allylic alcohol (0.23 g).

Example 224a: $^1$H NMR (CDCl$_3$, 500 MHz) delta (selected peaks) 5.65 (ddd, J=8.75, 16, 67.5 Hz, 1H), 3.43 (s, 3H), 3.38 (s, 3H), 3.32 (s, 3H), 1.67 (s, 3H), 1.63 (s, 3H), 106 (d, J=7.5 Hz, 3H), 0.84 (t, J=7.5 Hz, 3H).

Example 224b: IR (CDCl$_3$) cm$^{-1}$ 3440, 2930, 1740, 1650, 1450, 1090; $^1$H NMR (CDCl$_3$, 500 MHz) delta (selected peaks) 5.45 (ddd, J=6.5, 17.5, 42.5 Hz, 1H), 1.66 (s, 3H), 1.64 (s, 3 H), 1.04 (d, J=7.5 Hz, 3H), 0.99 (d, J=7.5 Hz, 3H), 0.87 (d, J=7.5 Hz, 3H), 0.83 (t, J=7.5 Hz, 3H); MS (FAB) m/e: M+K=814.

Example 225: Formula VII: R=ethyl; R'=H; n=1; $R^1$=t-butyldimethylsilyloxy (R configuration); $R^{21}$=H; $R^{22}$=$R^{23}$=OH; $R^{24}$=H; $R^{33}$t-butyldimethylsilyloxy: $R^{31}$=$R^{32}$=$R^{34}$=H; $R^{35}$ and $R^{36}$ taken together form an oxo group The title compound is prepared according to the procedures described in the published European patent application of Sandoz, No.040293 1 A1, Example 1.

Example 226: Formula VII: R=ethyl; R'=H; n=1; $R^1$=t-butyldimethylsilyloxy (R configuration); $R^{22}$=H; $R^{21}$=$R^{23}$=OH; $R^{24}$=H; $R^{33}$t-butyldimethylsilyloxy: $R^{31}$=$R^{32}$=$R^{34}$=H; $R^{35}$ and $R^{36}$ taken together form an oxo group The title compound is prepared according to the procedures described in the published European patent application of Sandoz, No.040293 1 A1, Example 2.

Example 227: Formula VII: R=ethyl; R'=H; n=1; $R^1$=t-butyldimethylsilyloxy (R configuration); $R^{22}$=H; $R^{21}$=N$_3$; $R^{23}$=OH; $R^{24}$=H; $R^{33}$=t-butyldimethylsilyloxy: $R^{31}$=$R^{32}$=$R^{34}$=H; $R^{35}$ and $R^{36}$ taken together form an oxo group A solution of triphenylphosphine (0.131 g) and diethyl azodicarboxylate (0.09 g) in dry tetrahydrofuran (THF, 2 mL) is added to a stirred solution of the product of Example 225 (0.45 g) in THF (10 mL) followed by a solution of diphenylphosphorylazide (0.14 g in 1 mL of THF). The reaction mixture is stirred at 45° C. and the progress is monitored by TLC analysis. The reaction is quenched with water and extracted with ethyl acetate. Solvent is removed and the product is purified by silica gel chromatography.

Example 228: Formula VII: R=ethyl; R'=H; n=1; $R^1$t-butyldimethylsilyloxy (R configuration); $R^{21}$=H; $R^{22}$=o-nitrobenzenesuffonate: $R^{23}$=OH; $R^{24}$=H; $R^{33}$=-t-butyldimethylsilyloxy; $R^{31}$=$R^{32}$=$R^{34}$=H; $R^{35}$ and $R^{36}$ taken together form an oxo group o-Nitrobenzenesulfonyl chloride (0.115 g) in dry methylene chloride (1 mL) is added into a stirred solution of the product of Example 225 (0.5 g) and triethylamine (0.1 g) in methylene chloride (5 mL) at room temperature. After stirring at room temperature overnight the solvent is removed and the product purified by silica gel chromatography.

Example 229: Formula VII: R=ethyl; R'=H; n=1; $R^1$=t-butyldimethylsilyloxy (R configuration); $R^{21}$N$_3$; $R^{22}$=H; $R^{23}$=OH; $R^{24}$=H; $R^{33}$=t-butyldimethylsilyloxy: $R^{31}$=$R^{32}$=$R^{34}$=H; $R^{35}$ and $R^{36}$ taken together form an oxo group Sodium azide (0.1 g) is added into a stirred solution of the product of Example 228 (0.12 g) in dry DMF (1 mL) at room temperature and heated at 60° C. for 5 hours. The reaction mixture is partitioned between ether and water. The organic phase is washed once with brine, dried over magnesium sulfate and the solvent is removed. The product is purified by silica gel chromatography.

Example 230: Formula VII: R=ethyl; R'=H; n=1; $R^1$=t-butyldimethylsilyloxy (R configuration); $R^{21}$=H; $R^{22}$=N$_3$; $R^{23}$=OH; $R^{24}$=H; $R^{33}$=t-butyldimethylsilyloxy: $R^{31}$=$R^{32}$=$R^{34}$=H; $R^{35}$ and $R^{36}$ taken together form an oxo group The title compound may be prepared according to the procedures described in Examples 227 or 229, but replacing the product of Example 225 with that of Example 226.

Example 231: Formula II: R=ethyl; R'=H; n=1; $R^{22}$=H; $R^{21}$=N$_3$; $R^{23}$=OH; $R^{24}$=H 40% Aqueous HF (0.1 mL) in acetonitrile (5 mL) is added into a stirred solution of the product of Example 227 (0.4 g) in acetonitrile (8 mL) at room temperature. The reaction mixture is diluted with water after stirring 2 hours at room temperature and extracted with ether. The organic phase is washed once with brine, dried over magnesium sulfate, and the solvent is removed. The product is purified by silica gel chromatography.

Example 232: Formula II: R=ethyl; R'=H; n=1; $R^{21}$=H; $R^{22}$=$N_3$; $R^{23}$=OH; $R^{24}$=H The title compound may be prepared according to the procedure described in Example 231, but replacing the product of Example 227 with that of Example 230.

Example 233: Formula II: R=ethyl; R'=H; n=1; $R^{22}$=H; $R^{21}$=$NH_2$; $R^{23}$=OH; $R^{24}$=H A solution of the product of Example 231 (0.25 g) and triphenylphosphine (0.09 g) in wet toluene (10 mL) is stirred at 70° C. for 8 hours. The solvent is removed and the product is purified by preparative TLC on silica.

Example 234: Formula II: R=ethyl; $R,$=H; n=1; $R^{22}$=$NH_2$; $R^{21}$=H; $R^{23}$=OH; $R^{24}$=H The title compound may be prepared according to the procedure described in Example 233, but replacing the product of Example 231 with that of Example 232.

Example 235: Formula II: R=ethyl; R'=H; n=1; $R^{22}$=H; $R^{21}$=NHAc; $R^{23}$=OH; $R^{24}$=H Acetic anhydride (0.15 g in 1 mL of dry methylene chloride) is added into a stirred solution of the product of Example 233 (0.4 g) containing methylamine (0.15 g) in methylene chloride, (5 mL) and the mixture is stirred at room temperature for I hour. The reaction mixture is partitioned between ether and 1 N HCl. The organic phase is washed once with brine, dried over magnesium sulfate and solvent removed. The product is purified by silica gel chromatography.

Example 236: Formula II: R=ethyl; R'=H; n=1; $R^{21}$=H; $R^{22}$=NHAc; $R^{23}$=OH; $R^{24}$=H The title compound may be prepared according to the procedure described in Example 235, but replacing the product of Example 233 with that of Example 234.

Example 237: Formula II: R=ethyl; R'=H; n=1; $R^{22}$=H; $R^{21}$=NH-adamantanecarbonyl; $R^{23}$=OH; $R^{24}$=H The title compound may be prepared according to the procedure described in Example 235 by replacing acetic anhydride with 1-adamantane carbonyl chloride.

Example 238: Formula II: R=ethyl; R'=H; n=1; $R^{21}$=H; $R^{22}$NH-adamantanecaxbonyl; $R^{23}$=OH; $R^{24}$=H The title compound may be prepared according to the procedure described in Example 236 by replacing acetic anhydride with 1-adamantane carbonyl chloride.

Example 239: Formula II: R=ethyl; R'=H; n=1; $R^{22}$=H; $R^{21}$=benzoylamido: $R^{23}$=OH; $R^{24}$=H The title compound may be prepared according to the procedure described in Example 235 by replacing acetic anhydride with benzoyl chloride.

Example 240: Formula II: R=ethyl; R'=H; n=1; $R^{21}$=H; $R^{22}$=benzoylamido; $R^{23}$=OH; $R^{24}$=H The title compound may be prepared according to the procedure described in Example 236 by replacing acetic anhydride with benzoyl chloride.

Example 241: Formula II: R=ethyl; R'=H; n=1; $R^{22}$=H; $R^{21}$=N-benzylamino; $R^{23}$=OH; $R_{24}$=H Benzyl bromide (0.1 g) is added into a stirred solution of the product of Example 233 (0.4 g) in acetonitrile (5 mL) at 0° C. After being stored at 0° C. overnight, the reaction mixture is refluxed for an additional hour. The product is purified by silica gel chromatography.

Example 242: Formula II: R=ethyl; R'=H; n=1; $R^{21}$=H; $R^{22}$=N-benzylamino; $R^{23}$=OH $R^{24}$=H The title compound may be prepared from benzyl bromide according to the procedure described in Example 241, but replacing the product of Example 233 with that of Example 234.

Example 243: Formula II: R=ethyl; R'=H; n=1; $R^{21}$=N-[(4',5'-biscarboethoxy)-triazole]; $R^{22}$=H; $R^{23}$=OH; $R^{24}$=H A mixture of the product of Example 231 (0.4 g) and diethylacetylene dicarboxylate (1 mL) is stirred at room temperature overnight. The triazole is purified by silica gel chromatography.

Example 244: Formula II: R=ethyl; R'=H; n=1; $R^{21}$=H; $R^{22}$=N-[(4',5'-dicarboethoxy)-triazole]; $R^{23}$=OH; $R^{24}$=H The title compound may be prepared according to the procedure described in Example 243, but replacing the product of Example 231 with the that of Example 232.

Example 245: Formula II: R=ethyl; R'=H; n=1; $R^{21}$=N-[(2',5'-dimethyl-pyrrole]; $R^{22}$=H; $R^{23}$=OH; $R^{24}$=H A solution of acetonylacetone (0.5 g) and the product of Example 233 (0.5 g) in absolute ethanol (5 mL) is refluxed for 6 hours. After removal of solvent, the product is purified by silica gel chromatography.

Example 246: Formula H: R=ethyl; R'=H; n=1; $R^{21}$=H; $R^{22}$=N-[(2',5'-dimethyl)-pyrrole]; $R^{23}$=OH; $R^{24}$=H The title compound may be prepared from acetonylacetone according to the procedure described in Example 245, but replacing the product of Example 233 with that of Example 234.

Example 247: Formula VII: R=ethyl; R'=H; n=1; $R^1$=t-butyldimethylsilyloxy (R configuration); $R^{22}$=H; $R^{21}$=iodo: $R^{23}$=OH; $R^{24}$=H; $R^{33}$=t-butyldimethylsilyloxy; $R^{31}$=$R^{32}$=$R^{34}$=H; $R^{35}$ and $R^{36}$ taken together form an oxo group Potassium iodide (0.1 g) is added into a stirred solution of the product of Example 228 (0.13 g) in dry DMF (1 mL) at room temperature and heated at 70° C. for 4 hours. The reaction mixture is partitioned between ether and water. The organic phase is washed once with brine, dried over magnesium sulfate and solvent removed. The product is purified by silica gel chromatography.

Example 248: Formula II; R=ethyl; R'=H; n=1; $R^{21}$=iodo; $R^{22}$=H; $R^{23}$=OH; $R^{24}$=H The product of Example 247 may be deprotected according to the procedure of Example 231 to give the title compound.

Example 249: Formula II: R=ethyl; R'=H; n=1; $R^{21}$=H; $R^{22}$=iodo: $R^{23}$=OH; $R^{24}$=H The title compound may be prepared according to the procedure of Examples 228, 247 and 248, but replacing the product of Example 225 with that of Example 226.

Example 250: Formula II: R=ethyl; R'=H; n=1; $R^{21}$=bromo; $R^{22}$=H; $R^{23}$=OH; $R^{24}$=H The title compound may be prepared according to the procedure of Examples 247 and 248, but replacing potassium iodide with potassium bromide.

Example 251: Formula II: R=ethyl; R'=H; n=1; $R^{21}$=H; $R^{22}$=bromo; $R^{23}$=OH; $R^{24}$=H The title compound may be prepared according to the procedure of Example 249, but replacing potassium iodide with potassium bromide.

Example 252: Formula VII: R=ethyl; R'=H; n=1; $R^1$=t-butyldimethylsilyloxy (R configuration); $R^{22}$=H; $R^{21}$=thiomethoxy; $R^{23}$=OH; $R^{24}$=H; $R^{33}$=t-butyldimethylsilyloxy; $R^{31}$=$R^{32}$=$R^{34}$=H; $R^{35}$ and $R^{36}$ taken together form an oxo group Sodium thiomethoxide (0.1 g) is added into a stirred solution of the product of Example 228 (0.12 g) in dry DMF (1 mL) at room temperature for 5 hours. The reaction mixture is partitioned between ether and water. The organic phase is washed once with brine, dried over magnesium sulfate and solvent removed. The product is purified by silica gel chromatography.

Example 253: Formula II: R=ethyl; R'=H; n=1; $R^{22}$=H; $R^{21}$=thiomethoxy; $R^{23}$=OH; $R^{24}$=H The product of Example 252 is deprotected according to the procedure of Example 231 to give the title compound.

Example 254: Formula II; R=ethyl; R'=H; n=1; $R^{21}$=H; $R^{22}$=thiomethoxy: $R^{23}$=OH; $R^{24}$=H The title compound may be prepared according to the procedure of Examples 228, 252 and 253, but replacing the product of Example 225 with that of Example 226.

Example 255: Formula VII: R=ethyl; R'=H; n=1; $R^1$=tert-butyldimethylsilyloxy (R Configuration); $R^{21}$ and $R^{22}$ taken together form an oxo group: $R^{23}$ and $R^{24}$ taken together form a bond: $R_{31}$=H; $R^{32}$=H; $R^{33}$=tert-butyldimethylsilyloxy; $R^{34}$=H; $R^{35}$ and $R^{36}$ taken together form an oxo group The product of Example 54 (407.8 mg, 0.4 mmol) was dissolved in 4 mL of pyridine at 0° C., and thionyl chloride (46.8 uL, 0.6 mmol) was added. It was then stirred at 0° C. for 15 min and at room temperature for 72 hours. Ethyl acetate (40 mL) was added to the reaction mixture, and the organic layer was washed with brine, 10%-$KHSO_4$, brine and then dried over anhydrous magnesium sulfate. Evaporation of the solvent gave 364 mg of crude product which was purified by silica gel (50 g) column chromatography, eluting 2.5%-ethyl acetate in chloroform. Yield: 168.7 mg of pure title compound was isolated. MS (FAB) m/z: M+K= 1040.

Example 256: Formula II: R=ethyl; R'=H; n=1; $R^{21}$ and $R^{22}$ taken together form an oxo group; $R^{23}$ and $R^{24}$ taken together form a bond The product of Example 255 (120 mg, 0.12 mmol) was dissolved in 2.5 mL of acetonitrile and 48% hydrofluoric acid (100 uL) was added. It was then stirred at room temperature for 1 hour. Ethyl acetate (30 mL) was added to the reaction mixture, and the organic layer was washed with brine, 10%-$NaHCO_3$, brine and then dried over anhydrous magnesium sulfate. Evaporation of the solvent gave 98.2 mg of crude product which was purified by silica gel (25 g) column chromatography, eluting with 1.5%-methanol in chloroform. 63.4 mg of pure title compound was isolated. MS (FAB) m/z: M+K=812.

Example 264: Formula I: R=ethanalyl; R'=H; n=1; $R^1$=H

A solution of osmium tetroxide (1 mL of a 4 % solution in water) is added into a stirred solution of the title compound of Example 263 (1.4 g) and 4-methylmorpholine N-oxide (1.4 g) in THF (25 mL) and water (15 mL) at room temperature. The reaction mixture is stirred at room temperature for an additional 4 hours. After addition of sodium metabisulfite, the reaction mixture is partitioned between water and ethyl acetate. The organic phase is washed with brine, dried over magnesium sulfate and solvent is removed. The residue is redissolved in benzene (40 mL) and lead tetraacetate (1.4 g) is added. After stirring at room temperature for 4 min., the reaction mixture is diluted with ether and the precipitate is filtered off. The solution is filtered through silica gel (5 g) with ether elution. After removal of solvent, the product is purified by silica gel chromatography.

Example 265: Formula I: R=carboxymethyl; R'=H; n=1; $R^1$=H

A solution of the product of Example 264 (0.8 g) in ethanol (5 mL) is added into a suspension of 10% Pd/C (0.1 g) in ethanol (10 mL). Air is bubbled through the stirred reaction mixture for 96 hours, and the solid is removed by filtration. After removal of solvent, the product is purified by silica gel chromatography.

Example 266: Formula I: R=methyl carboxymethyl; R'=H; n=1; $R^1$=H

A solution of diazomethane in ether is added into a stirred solution of the product of Example 265 (0.5 g) in methylene chloride (5 mL) until no starting material is present. A few drops of glacial acetic acid are added and the reaction mixture is stirred for 0.5 hours. Solvent is removed and the product is purified by silica gel chromatography.

Example 267: Formula I: R=N-morpholine-amidomethyl; R'=H; n=1; $R^1$=H

A solution of the product of Example 265 (0.2 g), morpholine (0.06 g), 1-ethyl-3-(3 -dimethylaminopropyl)carbhydrogen chloride (0.06 g) and 4-dimethylaminopyridine (0.06 g) in dry methylene chloride (4 mL) is stirred at room temperature overnight. The reaction mixture is partitioned between water and methylene chloride. After removal of solvent, the product is purified by silica gel chromatography.

Example 268: Formula I: R=N-beta-hydroxyethylamidomethyl; R'=H; n=1; $R^1$=H The title compound may be prepared from the product of Example 265 and ethanolamine according to the procedure described in Example 267.

Example 269: Formula I: R=carboxymethyl, amide with glycine methyl ester; R'=H; n=1; $R^1$=H The title compound may be prepared from the product of Example 265 and glycine methyl ester according to the procedure described in Example 267.

Example 270: Formula I: R=N-piperidine-amidomethyl; R'=H; n=1; $R^1$=H

The title compound may be prepared from the product of Example 265 and piperidine according to the procedure described in Example 267.

Example 271: Formula I: R=N-benzylamidomethyl; R'=H; n=1; $R^1$=H

The title compound may be prepared from the product of Example 265 and benzylamine according to the procedure described in Example 267.

Example 272: Formula I: R=N-n-butylamidomethyl; R'=H; n=1; $R^1$=H

The title compound may be prepared from the product of Example 265 and n-butylamine according to the procedure described in Example 267.

Example 273: Formula I: R=phenylcarboxymethyl; R'=H; n=1; $R^1$=H

The title compound may be prepared from the product of Example 265 and excess phenol according to the procedure described in Example 267.

Example 274: Formula I: R=2-oxopropyl; R'=H; n=1; $R^1$=H

A mixture of palladium (H) chloride (0.05 g) and copper (D chloride (0.1 g) in DMF (10 mL) and water (2 mL) is oxygenated by bubbling air through the mixture for 0.5 hours. A solution of the product of Example 263 (0.2 g) in DMF (2 mL) is added and the resulting reaction mixture is bubbled with air for 3 hours at room temperature. The reaction mixture is partitioned between ether and water. The organic phase is washed with dilute hydrochloric acid, brine and dried over magnesium sulfate. After removal of solvent, the product is purified by silica gel chromatography.

Example 275: Formula I: R=cyclopropylmethyl; R'=H; n=1; $R^1$=H

Diazomethane (20 ml, 1M in ether) is added dropwise into a solution of the product of Example 263 (0.2 g) and palladium (II) acetate (0.02 g) in ether (5 mL) at −5° C. After stirring at −5° C. for 1 hour, the precipitate is filtered off and solvent removed in vacuo. The product is purified by silica gel chromatography.

Example 276: Formular V; n=1; $R^1$=H; $R^{31}$=H; $R^{32}$=H; $R^{33}$=OH; $R^{34}$=H; $R^{35}$, $R^{36}$, R and R' taken together with the carbon atoms to which they are attached form a pyyrole with C- 22 and C-21 becoming positions 2' and 3' of the heterocyclic system A solution of the product of Example 264 (0.5 g) in methylene chloride (10 mL) is treated with ammonia (0.88M, aq., 0.4 mL). After stirring at room temperature for 0.25 hours, the reaction mixture is partitioned between ethyl acetate and water. The organic phase is washed once with brine, dried over magnesium sulfate and solvent removed. The product is purified by silica gel chromatography.

Example 277: Formular V: n=1; $R^1$=H; $R^{31}$=H; $R^{32}$=H; $R^{33}$=OH; $R^{34}$=H; $R^{35}$, $R^{36}$, R and R' taken together with the carbon atoms to which they are attached form a N-(beta-hydroxyethyl)-pyrrole with C-22 and C-21 becoming positions 2' and 3' of the heterocyclic system The title compound may be prepared from the product of Example 264 and 2-aminoethanol according to the procedure described in Example 276.

Example 278: Formular V; n=1; $R^1$=H; $R^{31}$=H; $R^{32}$=H; $R^{33}$=OH; $R^{34}$=H; $R^{35}$, $R^{36}$, R and R' taken together with the carbon atoms to which they are attached form a N-benzylpyrrole with C-22 and C-21 becoming positions 2' and 3' of the heterocyclic system The title compound may be prepared from the product of Example 264 and benzylamine according to the procedure described in Example 276.

Example 279: Formular V; n=1; $R^1$=H; $R^{31}$=H; $R^{32}$=H; $R^{33}$=OH; $R^{34}$=H; $R^{35}$, $R^{36}$, R and R' taken together with the carbon atoms to which they are attached form a N-phenylpyrrole with C-22 and C-21 becoming positions 2' and 3' of the heterocyclic system The title compound may be prepared from the product of Example 264 and aniline according to the procedure described in Example 276.

Example 280: Formular V: n=1; $R^1$=H; $R^{31}$=H; $R^{32}$=H; $R^{33}$=OH; $R^{34}$=H; $R^{35}$, $R^{36}$, R and R' taken together with the carbon atoms to which they are attached form a N-methylpyrrole with C-22 and C-21 becoming positions 2' and 3' of the heterocyclic system The title compound may be prepared from the product of Example 264 and methylamine according to the procedure described in Example 276.

Example 281: Formular V: n=1; $R^1$=H; $R^{31}$=H; $R^{32}$=H; $R^{33}$=OH; $R^{34}$=H; $R^{35}$, $R^{36}$, R and R' taken together with the carbon atoms to which they are attached form at furan with C-22 and C-21 becoming positions 2' and 3' of the heterocyclic system The product of Example 264 (0.2 g) and p-toluenesulphonic acid (0.005 g) in dry methylene chloride is refluxed under nitrogen for 1 hour. After removal of solvent, the product is purified by silica gel chromatography.

Example 282: Formula III: R=ethyl; R'=H; n=1; $R^{31}$=H; $R^{32}$=H; $R^{33}$=t-butyldimethylsilyloxy: $R^{34}$=H; $R^{35}$ and $R^{36}$ taken together form an oxo group A solution of the product of Example 54 (1.0 g) in acetonitrile (10 mL) was added into a stirred solution of HF (0.1 mL, 40% aqueous) in acetonitrile (10 mL) and stirred at room temperature for 10 min. Saturated sodium bicarbonate (0.5 mL, aqueous) was added and stirred for 20 min. Solvent was removed in vacuo. Ether (50 mL) was added to the residue and the mixture dried over magnesium sulfate. Solid was removed by filtration and solvent removed in vacuo. The product was purified by silica gel (20 g) eluting with 20% (v/v) acetone in hexanes. Yield: 0.67 g; MS (FAB) m/z: M+K=944.

Example 283: Formula V; R=ethyl; R'=H; n=1; $R^2$=H; $R^{2'}$=H; $R^3$ and $R^4$ taken together form an oxo group; $R^{31}$=H; $R^{32}$=H; $R^{33}$=t-butyldimethylsilyloxy: $R^{34}$=H; $R^{35}$ and $R^{36}$ taken together form an oxo group The title compound was prepared from the product of Example 282 according to the procedure described in Example 48. MS (FAB) m/z: M+K=942.

Example 284: Formula V; R=ethyl; R'=H; n=1; $R^2$=H; $R^{2'}$=H; $R^3$ and $R^4$ taken together form an oxime; $R^{31}$=H; $R^{32}$=H; $R^{33}$t-butyldimethylsilyloxy; $R^{34}$=H; $R^{35}$ and $R^{36}$ taken together form an oxo group N-methylmorpholine (0.1 mL) was added into a stirred solution of hydroxylamine hydrochloride (0.05 g) and the product of Example 283 (0.52 g) in absolute ethanol (3 mL) and stirred at room temperature for 1 hour. The reaction mixture was refluxed for 1 hour and solvent removed. The product was purified by silica gel (20 g) eluting with 20% acetone in hexanes. Yield: 0.5 g; MS (FAB) m/z: M+K=957.

Example 321: Formula II: R=H; R'=allyl: n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system: $R^{60}$=OH (R configuration); $R^{65}$=H A solution of "17-epi-FK-506" (as described in published European Patent Application No. 356399) (0.41 g), o-phenylenediamine (0.108 g) and N-methylmorpholine (0.072 g) in absolute ethanol (3 mL) is refluxed under nitrogen overnight. Solvent is removed in vacuo and product is purified on silica gel (10 g) with methylene chloride/acetonitrile (5:2, v/v) elution, followed by 40% acetone in hexanes to give the desired compound.

Example 322: Formula II: R=ethyl; R'=H; n=1; taken together with the carbon atoms to which they are attached, $R^{26}$, $R^{27}$, $R^{28}$ and $R^{29}$ form a fused naphthalene group wherein the atoms adjacent to C-9 and C-10 are substituted by cyano groups; $R^{60}$=OH (R configuration); $R^{65}$=H Ascomycin (1 mmol) is reacted with 1,2-phenylenediacetonitrile and piperidine according to published methods of ring formation (Bull. Soc. Chim. Fr. 1946, 106; J. Am. Chem. Soc. 1951, 73, 436). Solvent is removed in vacuo and product is purified on silica gel to give the desired compound.

Example 323: Formula II: R=ethyl; R'=H; n=1; taken together with the carbon atoms to which they are attached, $R^{26}$ and $R^{28}$ are each OH; $R^{27}$ and $R^{29}$ taken together form —$CH_2$—C($CH_2$)—$CH_2$— group; $R^{60}$=OH (R configuration); $R^{65}$=H Ascomycin (1 mmol) is reacted with 1-trimethylsilyl-2-iodomethyl-prop-2-ene and $SnF_2$ according to published methods of ring formation (J. Am. Chem. Soc. 1986, 108, 4683). Solvent is removed in vacuo and product is purified on silica gel to give the desired compound.

Example 324: Formula V: R=ethyl; R'=H; n=1; X=subformula Ia: $R^1$=TBSO-(R-configuration): Y=subformula IIIa; $R^{31}$ and $R^{32}$ taken together form a diazo; $R^{33}$ and $R^{34}$ taken together form an oxo: $R^{35}$ and $R^{36}$ taken together form an oxo The product of Example 8b (16.9 g, 18.7 mmol) in $CH_3CN$ containing water (0.34 mL, 18.7 mmol) and triethylamine (3.9 mL, 28.1 mmol, 1.5 eq) was treated with a portion of methanesulfonylazide (4.5 mL, 56.2 mmol) at ambient temperature (7 hours). The mixture was concentrated in vacuo and filtered through a plug of silica gel (300 mL, 70–230 mesh) eluting with hexane:EtOAc (1 L, 2:1). Fractions containing product were pooled and concentrated. This was purified further by HPLC on silica gel (50mm×500 mm, 230–400 mesh) eluting with hexane:EtOAc (6 L, 5:1). The appropriate fractions were combined and concentrated to provide product as a yellow foam (13.8 g, 14.8 mmol) in 79% yield. IR ($CDCl_3$) 2130, 1743, 1645 cm$^{-1}$; MS (FAB) m/z 968 (M+K), 940 (M+K–$N_2$).

Example 325: Formula V: R=ethyl; R'=$R^{35}$=$R^{36}$=H; n=1; X=subformula Ia; $R^1$=TBSO-(R configuration): Y=subformula IIIa'; $R^{33}$ and $R^{34}$ taken together form an oxo The product of Example 324 (13.8 g, 14.8 mmol) in N-methylpyrollidone (600 mL) containing water (96 mL) was heated at 110° C. for 80 min after gas evolution commenced. The mixture was cooled and partitioned between EtOAc (1 L) and water (1 L). The aqueous layer was extracted with additional EtOAc (1 L). The organic layers were each washed sequentially with water (1 L) and brine (500 mL), and were then combined and dried ($NaSO_4$). The solvent was removed invacuo and the residue was passed through a silica gel column (300 mL, 70–230 mesh) eluting with a mixture of hexane:EtOAc (2:1, 2 L). The fractions containing product were combined and concentrated to a yellow oil (10 g) which was further purified by HPLC on silica gel (1 L, 230–400 mesh) eluting with hexane:EtOAc (5:1). This provided pure product (5.3 g, 6.1 mmol) in 41% yield. IR ($CDCl_3$) 1750, 1722, 1705 (sh), 1645 cm$^{-1}$; MS (FAB) m/z 914 (M+K).

Anal. Calcd. for $C_{48}H_{81}NO_{11}Si$: C, 65.79; H, 9.32; N, 1.60. Found: C, 65.57; H, 9.08; N, 1.56.

Example 326: Formula V: R=ethyl; R'=$R^2$=$R^{2'}$=H; n=1; X=subformula Ib; $R^3$ and $R^4$ taken together form an oxo; Y=subformula IIIa; $R^{31}$ and $R^{32}$ taken together form a diazo; $R^{33}$ and $R^{34}$ taken together form an oxo; $R^{35}$ and $R^{36}$ taken together form an oxo The product of Example 14a (3.56 g, 4.5 mmol) in acetonitrile (89 mL) containing water (82 micro-L, 4.5 mmol) and triethylamine (0.95 mL, 6.8 mmol, 1.5 eq.) was treated with methanesulfonylazide (1.09 mL, 13.6 mmol, 3 eq.) for 6 h. Volatiles were immediately removed invacuo and the residue purified by MPLC on 230–400 mesh $SiO_2$ (2.54 cm×45 cm column) eluting with hexane:acetone (4:1) collecting 100 mL fractions throughout, which provided pure product (2.73g, 3.35 mmol)in 75% yield. IR (film) 2930, 2115, 1725, 1645, 1455, 1200 $cm^{-1}$; MS (FAB) m/z (M+K+thioglycerol)=932, (M+K)=852, (M+K–$N_2$)=824.

Example 327: Formula V: R=ethyl; R'=$R^2$=$R^2$=H; n=1; X=subformula Ib: Y=subformula IIIa'; $R^{33}$ and $R^{34}$ taken together form an oxo The product of Example 326 (1.0 g, 1.23 mmol) in N-methylpyrollidone (50 mL) and water (8 mL) was heated at 110° C. (45 min). The reaction mixture was cooled and partitioned between water (500 mL) and EtOAc (300 mL). The aqueous layer was extracted with additional EtOAc (300 mL). The organic layers were washed with additional water (500 mL) and brine (500 mL), combined, and dried ($Na_2SO_4$). The extract was decanted from the drying agent and concentrated to a colorless foam (1.04 g), which was purified by silica gel chromatography (70–230 mesh, 300 mL) eluting with hexane:acetone (4:1, 2.5 L). The appropriate fractions were pooled and concentrated to provide pure product (0.55 g, 0.72 mmol) in 59% yield. IR ($CDCl_3$) 1743, 1721, 1643 $cm^{-1}$; MS (FAB) m/z 798 (M+K).

Anal. Calcd. for $C_{42}H_{65}NO_{11}$: C, 66.38; H, 8.62; N, 1.84. Found: C, 66.74; H, 8.29; N, 2.25.

Example 328: Formula V: R=ethyl; R'=$R^{34}$=$R^{35}$=$R^{36}$=H; n=1; X=subformula Ia: $R^1$=TBSO-(R configuration): Y=subformula IIIa'; $R^{33}$=OH A 1.0M solution of LiAlH(Ot—Bu)$_3$ in THF (8.2 mL, 8.2 mmol) was added dropwise to the product of Example 325 (1.8 g, 2.05 mmol) in THF (8.0 mL) at –78° C. and allowed to stir for 1 h, whereupon it was warmed to –40° C. and stirred at this temperature for 24 h. The reaction was quenched by the addition of acetone (1.1 mL) and then stirred vigorously at room temperature for 15 minutes with a saturated aqueous solution of sodium potassium tartrate (30 mL). The mixture was partitioned between water (60 mL) and EtOAc (100 mL). The organic layer was washed with 1N HCl (40 mL) and brine (2×50 mL). All aqueous layers were extracted with additional EtOAc (100 mL ). The organics were combined, dried ($Na_2SO_4$) and concentrated in vacuo. Purification by chromatography on 70–230 mesh silica gel (20 g) eluting with toluene:EtOAc (5:1) provided pure product (0.9 g, 1.03 mmol) as a colorless foam in 50% yield. IR ($CDCl_3$) 1735, 1720 (sh), 1670, 1645 $cm^{-1}$; MS (FAB) m/z 918 (M+K).

Example 329: Formula III: R=ethyl; R'=$R^{34}$=$R^{35}$=$R^{36}$=H; n=1; Y=subformula IIIa'; $R^{33}$=OH A 1M solution of HF (0.35 mL, 0.35 mmol (0.42 mL 48% aqueous HF in 9.58 mL $CH_3CN$ provides a 1M solution)) was added dropwise to a solution of the product of Example 328 (290 mg, 0.33 mmol) in acetonitrile (3.2 mL) at 0° C. The mixture was warmed to room temperature and stirred for 45 minutes, whereupon it was cooled to 0° C. and solid pulverized $NaHCO_3$ (244 mg, 2.9 mmol) was added. After 30 minutes anhydrous $MgSO_4$ (250 mg) was added and the mixture stirred for 15 minutes, when it was diluted with methylene chloride (15 mL), centrifuged and passed thru a plug of silica gel. The silica was eluted with hexane:acetone (1:1), and the fractions containing product were pooled, concentrated and purified by HPLC on silica gel eluting with hexane:acetone (2:1) providing desired product (163 mg, 0.21 mmol) in 64% yield. IR ($CDCl_3$) 1735, 1645 $cm^{-1}$; MS (FAB) m/z 802 (M+K).

Anal. Calcd. for $C_{42}H_{69}NO_{11}$: C, 66.03; H, 9.10; N, 1.83. Found: C, 65.92; H, 8.93; N, 1.76.

Example 354: Formula III: R=ethyl; R'=H; n=1: $R^{31}$=$R^{32}$=H; one of $R^{33}$ and $R^{34}$=H and the other=N-benzylpiperazinlyl; $R^{35}$ and $R^{36}$ taken together form oxo The product of Example 36 (500 mg, 0.65 mmol) was dissolved in 5 mL of methylene chloride containing 1-benzyl-piperazine (337 μL, 1.95 mmol) and triethylamine (270 μL, 1.95 mmol). The mixture was stirred at room temperature for one over night Ethyl acetate (50 mL) and brine solution were added and partitioned. The ethyl acetate layer was washed with brine (×3), dried over anhydrous magnesium sulfate. Purification was carried out by silica gel column, followed by HPLC to obtain the title compound. Yield 159 mg (26%), MS (FAB) m/z: M+H=950, M+K=988.

Example 355: Formula III; R=ethyl; R'=H; n=1; $R^{31}$=$R^{32}$=H: one of $R^{33}$ and $R^{34}$=H and the other=N-methylpiprazinyl; $R^{35}$ and $R^{36}$ taken together form oxo The title compound was prepared from the product of Example 36 (700 mg, 0.91 mmol) and 1-methylpiperazine (507 μL, 4.55 mmol), according to the procedure described in Example 354. Yield 208 mg (26%), MS (FAB) m/z: M+H=874, M+K=912.

Example 356: Formula III; R=ethyl; R'=H; n=1; $R^{31}$=$R^{32}$=H: one of $R^{33}$ and $R^{34}$=H and the other=N-phenylpiperazinyl; $R^{35}$ and $R^{36}$ taken together form oxo The title compound was prepared from the product of Example 36 (500 mg, 0.65 mmol) and 1-phenylpiperazine (493 gL, 3.25 mmol), according to the procedure described in Example 354. Yield 248 mg (41%), MS (FAB) m/z: M+H=936, M+K=974.

Example 363: Formula V: R=ethyl: n=1; R'=H; $R^1$t-butyldimethylsilyloxy; $R^{31}$=H; $R^{32}$=H; $R^{33}$=OH; $R^{34}$=H; $R^{35}$—O-benzoyl (S-configuration); $R^{36}$=H To a stirred solution of 32-TBDMS, 22-S-dihydro ascomycin (prepared according to the procedure of Example 103c, 0.14g, 0.15 mmol) and triethylamine (0.10 mL, 0.7 5 mmol) in $CH_2Cl_2$ (3 mL) was added benzoyl chloride (0.052 mL, 0.45 mmol) followed by DMAP (0.002 g, 0.015 mmol). The reaction was stirred at room temperature overnight, and then diluted with ethyl acetate. The ethyl acetate layer was washed with 0.1M $H_3PO_4$, $NaHCO_3$, brine and dried over $Na_2SO_4$. Evaporation provided the title compound (0.13 g).

Example 365: Formula III: R=ethyl: n=1; R'=H; $R^{31}$=H; $R^{32}$=H; $R^{33}$=OH; $R_{34}$=H; $R^{35}$=—O-benzoyl (S-configuration); $R^{36}$=H The crude product derived from the procedure of Example 363 (0.13 g) was treated with HF according to the procedure of Example 60 and then purified by RP-HPLC (41.4 mm ID, Dynamax-60A 8 μm phenyl, 83-D4 1—C) to give 0.085 g of the title compound in 64% yield. FAB-MS (m/z) 936 (M+K).

Examples 365a and 365b: Formula V:
R=2-hydroxyethyl: n=1; R'=H;
$R^1$=tt-butyldimethylsilyloxy: $R^{31}$=H; $R^{32}$=H;
$R^{33}$=t-butyldimethylsilyloxy: $R^{34}$=H; $R^{35}$ and $R^{36}$ taken together form an oxo group, and Formula VII: R=2-hydroxyethyl: n=1; R'=H;
R1=t-butyldimethyl-silyloxy: one of $R^{21}$ and $R^{22}$ is H and the other is OH; $R^{23}$=OH; $R^{24}$=$R^{31}$H;
$R^{32}$=H; $R^{33}$=t-butyldimethylsilyloxy; $R^{34}$=H; $R^{35}$ and $R^{36}$ taken together form an oxo group To a stirred solution of 32,24 -bisTBDMS, 21-ethanal ascomycin (0.50 g, 0.50 mmol, prepared according to the methods described in published PCT applications Nos. WO 89/05304 and WO 91/04025) and sodium triacetoxyborohydride (0.31 g, 1.45 mmol) in $CH_3CN$ (15 mL) at 0° C. was added acetic acid (0.25 mL, 4.36 mmol). The reaction mixture was stirred at 0° for 2 hours, quenched with water, and stirred for another 0.5 hour while warming to room temperature. The reaction mixture was then partitioned between ethyl acetate and brine. The ethyl acetate layer was washed sequentially with aqueous $NaHCO_3$ and brine, dried over $Na_2SO_4$ and concentrated to give 0.56 g of crude product. Purification was done by silica gel column chromatography, eluting with 7.5% to 15% acetone in hexane. The desired product 32,24-bisTBDMS, 21-ethanol ascomycin (Example 365a, 0.11 g) was collected along with the starting material (0.13 g) and the direduction product (Example 365b, 0.06 g) which was also reduced at position C-9.

Example 366: Formula V: R=2-benzoyloxyethyl:
n=1; R'=H; R1=t-butyldimethylsilyloxy; $R^{31}$=H;
$R^{32}$=H; $R^{33}$=t-butyldimethylsilyloxy: $R^{34}$=H; $R^{35}$ and $R^{36}$ taken together form an oxo group The product of Example 365a (32,24-bisTBDMS, 21-ethanol ascomycin, 110 mg) was reacted with benzoyl chloride using the same conditions used in Example 363. Purification of the titled bis-TBDMS protected benzoate was achieved using a silica gel column. Yield: 90 mg.

Example 367: Formula III: R=2-benzoyloxyethyl;
n=1; R'=H; $R^{31}$=H; $R^{32}$=H; $R^{33}$=OH; $R^{34}$=H; $R^{35}$ and $R^{36}$ taken together form an oxo group The product of Example 366 (32,24-bisTBDMS, 21-ethyl benzoate ascomycin, 90 mg) was treated with HF according to the procedure of Example 60 and purified by RP-HPLC to give 0.04 g of the title compound.

FAB-MS (m/z) 950 (M+K). Anal. Calcd. for $C_{50}H_{73}N_1O_{14} \cdot H_2O$: C, 64.57; H, 8.13; N, 1.51. Found: C, 64.66; H, 8.02; N, 1.71.

Examples 368a and 368b: Formula III: R=ethyl:
n=1; R'=H; $R^{31}$=H; $R^{32}$=H; $R^{34}$=H; $R^{33}$ and $R^{35}$ (S-configuration) taken together form
—O—C(CH_2!)_2—O—; $R^{36}$=H, and Formula III: R=ethyl: n=1; R'=H; $R^{31}$=H; $R^{32}$=H;
$R^{34}$=H; $R^{33}$ and $R^{35}$ (R-configuration) taken together form —O—$C(CH_3)_2$—O—; $R^{36}$=H To a stirred solution of ascomycin (0.5 g, 0.6 mmol) in $CH_3CN$ (8 mL) at 0° C. was added acetic acid (0.12 mL, 2.1 mmol) followed by sodium triacetoxyborohydride (0.15 g, 0.7 mmol). The reaction was stirred at 0° C. for 2 hours and quenched with water. The ice bath was removed and the reaction mixture was stirred for another 0.5 hour while warming to room temperature. The reaction mixture was partitioned between ethyl acetate and brine. The organic layer was washed sequentially with aqueous $NaHCO_3$ and brine, and dried over $Na_2SO_4$. The solvent was concentrated to give 0.51 g of crude material containing both S and R isomers of $C_{22}$-dihydro ascomycin along with the unreacted starting material. The above crude material was dissolved in DMF (5 mL) containing dimethoxypropane (5 mL). Pyridinium p-toluenesulfonate (0.05 g) was added, and the mixture was stirred at the room temperature overnight. The reaction mixture was diluted with ether and washed with brine. The ether was dried over $Na_2SO_4$ and evaporated to give 0.56 g of the crude $C_{22,24}$-acetonides. Purification was done by RP-HPLC (41.4 mm ID, Dynamax-60A 8 um phenyl, 83-D41-C) to isolate 0.15 g of $C_{22}$-S,24-acetonide and 0.025 g of $C_{22}$-R,24-acetonide isomer along with 0.096 g of ascomycin and 0.03 g of C22-R-dihydro ascomycin. 1H-NMR d 1.3 (s, 6H) for 22,24-S-acetonide, d 1.42 (s, 6H) for 22,24-R-acetonide; FAB-MS (m/z) 872 (M+K)

Example 369: Formula V: R=ethyl: n=1; R'=H;
R1=t-butyldimethylsilyloxy: $R^{31}$=H; $R^{32}$=H;
$R^{33}$=OH; $R_{34}$=H; $R_{35}$=—O—$CO_2Bn$ (S-configuration); $R^{36}$=H 32-TBDMS, 22-S-dihydro ascomycin (0.5 g,0.63 mmol), prepared according to the procedure of Example 103c, N-(benzyloxycarbonyloxy)succinimide (0.27 g, 1.1 mmol) and DMAP (0.07 g, 0.63 mmol) in $CH_2Cl_2$ (10 mL) were stirred at room temperature for 7 days. Purification was done by silica gel column chromatography, eluting with 5/95 acetone/hexane to give 0.31 g of 32-TBDMS, 22-S-benzyl carbonate ascomycin in 54% yield.

Example 370: Formula III: R=ethyl: n=1; R'=H;
$R^{31}$H; $R^{32}$=H; $R^{33}$=OH; $R^{34}$=H; $R^{35}$=—O—$CO_2Bn$ (S-configuration); $R^{36}$=H The product of Example 369 is treated with HF according to the procedure of Example 60 and purified by RP-HPLC to give the title compound.

Example 371: Formula VI: R=ethyl; R'=H: n=1;
$R^{26}$, $R^{27}$ and the carbon to which they are attached are absent: one of $R^{28}$ and $R^{29}$ is hydroxy and the other is —$COOCH_3$; C-8 is directly attached to C-10: $R^{31}$=H; $R^{32}$=H; $R^{33}$=H; $R^{34}$=H; $R^{35}$ and $R^{36}$ taken together form an oxo group; $R^{60}$=hydroxy (R configuration); $R^{65}$=H To a stirred solution of 24-desoxy ascomycin, the product of Example 380 (0.155 g, 0.2 mmol) in 1 mL of methanolic $ErCl_3 \cdot 6H_2O$ (0.2M) was added trimethylorthoformate (0.15 mL, 1.4 mmol). After stirring at room temperature for 5 hours, the reaction mixture was poured into aqueous $NaHCO_3$ and extracted with ether. The ether layer was washed with brine, dried over $Na_2SO_4$, and evaporated to give the crude product. After purification by RP-HPLC, the title compound (0.11 g) was isolated in 69% yield. FAB-MS (m/z) 846 (M+K)

Examples 372a and 372b: Formula II: R=ethyl; R'=H; n=1; $R^{26}$, $R^{27}$ and the carbon to which they are attached are absent: one of $R^{28}$ and $R^{29}$ is hydroxy and the other is —COOCH$_3$; C-8 is directly attached to C-10; $R^{60}$=hydroxy (R configuration); $R^{65}$=H, and Formula VI: R=ethyl; R'=H; n=1; $R^{26}$, $R^{27}$ and the carbon to which they are attached are absent: one of $R^{28}$ and $R^{29}$ is hydroxy and the other is —COOCH$_3$; C-8 is directly attached to C-10; $R^{31}$ and $R^{33}$ taken together form a bond; $R^{32}$=H; $R^{34}$=H; $R^{35}$=OCH$_3$; $R^{36}$OCH$_3$; $R^{60}$=hydroxy (R configuration); $R^{65}$=H The procedure of Example 371, in which 24-desoxy ascomycin was replaced with ascomycin, produced the title compounds of Examples 372a and 372b as major and minor products. FAB-MS (m/z) 890 (M+K).

Example 373: Formula III: R=ethyl; R'=H; n=1: $R^{31}$=$R^{32}$=$R^{34}$=H; $R^{33}$=hydroxy; $R^{35}$ or $R^{36}$=H and the other —NR$^{38}$ where $R^{38}$=—NHS(O)$_2$R$^{40}$ and $R^{40}$=4-methyphenyl The hydrazone obtained in Example 221 (1.00 g, 1.04 mmol), sodium cyanoborohydride (261 mg, 4.16 mmol) and p-toluenesulfonic acid monohydrate were combined in a mixture of N,N-dimethylformamide and sulfolane (1:1, 46 mL). This mixture was heated at 110° C. for 5.5 hours under a nitrogen atmosphere. The reaction mixture was diluted with water (200 mL) and extracted with ether (200 mL). Several washings of the organic phase were required to remove N,N-dimethylformamide and sulfolane. The ether layer was dried over sodium sulfate, and the solvent was removed under reduced pressure. The crude material was purified by flash chromatography on silica gel eluting with 40% acetone in hexane. The title compound was obtained as a solid (176 mg): mp 84°–87° C.; IR (CDCl$_3$) cm$^{-1}$ 3430, 2940, 1735, 1630, 1455, 1170, 1090; MS (FAB) m/e: M+K=1000.

Example 374: Formula III: R=ethyl; R'=H; n=1; $R^{31}$=H; $R^{32}$=H; $R^{33}$=OH; $R^{34}$=H; one of $R^{35}$ or $R^{36}$=—NH$_2$ and the other is H The oximes obtained from Example 7 (50 mg, 0.062 mmol) were combined with 10% palladium on charcoal in ethanol (10 mL, 100%). The mixture was placed under a hydrogen atmosphere (1 atm) and stirred at ambient temperature overnight. The catalyst was removed by passing the mixture through a filter agent, and the filtrate was evaporated to dryness to provide the title compound in quanititative yield: MS (FAB) m/e: M+K=831.

Example 375: Formula V: R=ethyl; R'=H; n=1; $R^{1=H;}$$^{R}$$^{31}$=$R^{32}$=$R^{33}$=$R^{34}$=H; $R^{35}$ and $R^{36}$ taken together form an oxo group The product of Example 259 is dehydrated as described in Example 36. This material is subsequently hydrogenated as described in Example 380 below to furnish the title compound after purification by flash chromatography on silica gel eluting with acetone and hexane.

Example 376: Formula V: R=ethyl; R'=H; n=1; $R^2$=$R^3$=H; R4 and $R^{2'}$ taken together form a bond: $R^{31}$=$R^{32}$=$R^{33}$=$R^{34}$=H; $R^{35}$ and $R^{36}$ taken together form an oxo group The product of Example 380 is dehydrated according to the procedure described in Example 362.

Example 377: Formula V: R=ethyl; R'=H; n=1: $R^2$=$R^3$=$R^{2'}$=H; $R^4$=OH, $R^{31}$=$R^{32}$=$R^{33}$=$R^{34}$=H; $R^{35}$ and $R^{36}$ taken together forman oxo group The product of Example 51 is dehydrated as described in Example 36. This material is subsequently hydrogenated as described in Example 380 below to furnish the title compound after purification by flash chromatography on silica gel eluting with acetone and hexane.

Example 378: Formula VI; R=ethyl; R'=H; n=1; taken together with the carbon atoms to which they are attached, $R^{26}$, $R^{27}$, $R^{28}$ and $R^{29}$ form a quinoxaline with C-9 and C-10 becoming positions 2' and 3' of the heterocyclic system; $R^{31}$=$R^{32}$=$R^{33}$$R^{34}$=H; $R^{35}$ and $R^{36}$ taken together form an oxo group: $R^{60}$=OH (R configuration); $R^{65}$=H The product of Example 38 is hydrogenated as described in Example 380 to supply the title compound after purification by flash chromatography on silica gel eluting with acetone and hexane.

Example 380: Formula III: R=ethyl; R'=H; n=1; $R^{31}$=$R^{32}$=$R^{33}$=$R^{34}$=H; $R^{35}$ and $R^{36}$ taken together form an oxo group The enone obtained in Example 36 (1.00 g, 1.29 mmol) was combined with 10% palladium on carbon (100 mg) in methanol and reduced under a hydrogen (1 atm) environment for 4 hours. The catalyst is removed by passing the mixture through a filter agent and the filtrate is concentrated under reduced pressure. The crude material was purified by flash chromatography on silica gel eluting with 25% acetone in hexane to supply the title compound (348 mg) as a colorless foam: MS (FAB) m/e: M+K=814.

Examples 381a and 381b: Formula III: R=ethyl; R'=H; n=1; $R^{33}$=H; $R^{34}$—O—; $R^{31}$=$R^{32}$=H; $R^{35}$ and $R^{36}$ taken together form =N— which is attached to the —O— at $R^{34}$ to form an isoxazoline, and Formula III: R=ethyl; R'=H; n=1: $R^{33}$—O—; $R^{34}$=H; $R_{31}$=$R^{32}$=H; $R^{35}$ and $R^{36}$ taken together form =N— which is attached to the —O— at $R^{33}$ to form an isoxazoline The oxime mixture obtained in Example 7 (250 mg, 0.310 mmol) was dissolved in methylene chloride (25 mL), and the solution was chilled to 0° C. Martin sulfurane dehydrating reagent (208 mg, 0.310 mmol) was added. Two more equivalents of dehydrating reagent were added after one and two hours of reaction respectively. The reaction was quenched with isopropanol (3 mL), and the mixture washed with saturated aqueous bicarbonate solution (80 mL). The organic phase was dried and freed of solvent. The products were separated and purified by flash chromatography on silica gel eluting with 30% acetone in hexane. Example 381a: MS (FAB) m/e: M+K=827. Example 381b: MS/FAB) m/e: M+K=827.

Example 382: Formula III: R=ethyl; R'=H; n=1;
$R^{31}=R^{32}=R^{34}=H$; $R^{33}=OH$; $R^{35}$ and $R^{36}$ taken
together are $=NR^{48}$ where $R^{48}$ is
—OCH$_2$CH=CH$_2$ Ascomycin (2.02 g, 2.54 mmol) was dissolved in 90% ethanol (40mL) To this solution was added O-allyl hydroxylamine hydrochloride (0.6275 g, 5.72 mmol) followed by pyridine (0.2 mL, 2.54 mmol). The reaction was stirred at room temperature for 23 hours. It was then poured into water (75 mL) and extracted with ethyl acetate (2×75 mL). The extracts were combined and washed with brine (50 mL) and dried over magnesium sulfate. Removal of the solvent gave crude material which was flash chromatographed on silica gel eluting with 30% acetone in hexane. Yield 1.97 g: MS (FAB) m/e: M+K=885; $^{13}$C NMR (75 MHz) delta (selected signals) 196.7, 161.6, 133.6, 118.5, 74.9; IR (KBr)cm$^{-1}$ 3450, 2930, 1745, 1720, 1650, 1450, 1100.

Example 383: Formula VIII: R=ethyl; R'=H; n=1;
$R_{31}$ and $R^{33}$ taken together form a bond;
$R^{32}=R^{34}=H$; $R^{35}$ and $R^{36}$ taken together form an oxo group The product of Example 36 (502 mg, 0.646 mmol) was dissolved in anhydrous tetrahydrofuran (40 mL). Potassium hydride (193 mg, 1.61 mmol as a 35% suspension in mineral oil) was added and the reaction stirred at room temperature. After 19 hours, an additional aliquot of potassium hydride (76 mg, 0.646 mmol) was added followed by quenching 7 hours hence. The tetrahydrofuran was removed, and the material partitioned between 25 mL of 1N hydrochloric acid and 25 mL of ethyl acetate. The aqueous phase was washed with an additional 15 mL of ethyl acetate. The organic phases were combined, washed with 20 mL of brine, dried over magnesium sulfate and freed of solvent. This material was flash chromatographed on silica gel eluting with 30% acetone in hexane. Yield 59 mg: MS (FAB) m/e: M+K=812; $^{13}$C NMR (125 MHz) delta (selected signals) 96.4, 80.1, 75.2; IR (KBr) cm$^{-1}$ 3430, 2920, 1755, 1735, 1690, 1625, 1455, 1090.

Example 384: Formula VIII: R=ethyl; R'=H; n=1;
$R^{3.1}$ and $R^{33}$ taken together form a bond;
$R^{32}=R^{34}=H$; one of $R^{35}$ or $R^{36}=H$ and the other=—OH The product of Example 224 (102 mg, 0.128 mmol) was dissolved in tetrahydrofuran (10 mL). Potassium hydride (20 mg, 0.462 mmol) as a 35% suspension was added, and the reaction mixture was stirred at room temperature for 20 hours. The mixture was quenched with water (0.5 mL) and concentrated under reduced pressure. The residue was partitioned between 0.5N hydrochloric acid and ethyl acetate (50 mL). The aqueous phase was washed again with ethyl acetate (25 mL), and the combined organic washes were dried over magnesium sulfate and freed of solvent. The crude material was purified by flash chromatography silica gel eluting with 30% acetone in hexanes. Yield 50 mg: MS (FAB) m/e: M+K=814; 13 C NMR (125 MHz) (delta, selected signal) 202.8, 76.4, 75.8, 74.5, 71.8.

Example 385: Formula V: R=ethyl; R'=H; n=1;
$R^1$=tert-butyldimethylsiloxy: $R^{31}$ and $R^{33}$ taken together form a bond; $R^{32}=R^{34}=H$; one of $R^{35}$ and $R^{36}$=H and the other is —OC(O)CH$_2$CH$_3$ The product of Example 36 was dehydrated and the pendant cyclohexanol hydroxyl group protected as its t-butyldimethylsilyl ether as described in Example 8a. Propionic acid (50 microliters, 0.673 mmol) was dissolved in hexane (10 mL) and N,N-dimethylformamide (50 microliters). To this, oxalyl chloride (0.29mL, 3.37 mmol) was added, and the reaction mixture stirred at room temperature for 1 hour. The salts were then removed by filtration, and the solvent removed in vacuo. The freshly made acid chloride was taken into anhydrous methylene chloride (10 mL). The hydrated, protected ascomycin derivative described above (202 mg, 0.225 mmol) was added along with diisopropylethylamine (0.2 mL, 1.13 mmol). After 48 hours, the dichloromethane was removed and the material partitioned between 1N hydrochloric acid (30 mL) and ethyl acetate (30 mL). The aqueous layer was washed with an additional ethyl acetate (15 mL). The organics were combined, washed with brine and dried over magnesium sulfate. The solvent was then removed and the material flash chromatographed on silica gel eluting with 25% acetone in hexane. Yield 101 mg: MS (FAB) m/e: M+K=946.

Example 386: Formula III: R=ethyl; R'=H; n=1;
$R^{31}=R^{32}=R^{34}=H$; $R^{33}$=—CH(—)CO$_2$Et; $R^{35}$ and $R^{36}$ taken together are =N— which is attached to C22 and the unoccupied valence of the methine on $R^{33}$ to form a cyclic imine The 4-chlorobenzylimine of glycine ethyl ester (1.46 g, 6.46 mmol) was dissolved in 80 mL of anhydrous tetrahydrofuran. To this, 0.39 g (9.70 mmol) of sodium hydride as a 60% suspension in mineral oil was added. These were allowed to stir at room temperature for 15 min, before adding 2.00 g (2.58 mmol) of the product of Example 36. After 24 hours at room temperature, the reaction was quenched by the addition of 10 mL of water. The tetrahydrofuran was removed, and the residue loaded onto silica gel and eluted with 25% acetone in hexane. Yield 0.60 g: MS (FAB) m/e: M+K=897, M+H=859.

Example 387: Formula III: R=ethyl; R'=H; n=1;
$R^{31}$=—CH(NH(—))p-chlorophenyl in which the unoccupied valence of the amine and the unoccupied valence on $R^{33}$ forming a pyrrolidine;
$R^{32}=R^{34}=H$; $R^{33}$=—CH(—)CO$_2$Et; $R^{35}$ and $R^{36}$ taken together form an oxo group The product of Example 36 (501 mg, 0.464 mmol) and the 4-chlorobenzylimine of glycine ethyl ester (218 mg, 0.97 mmol) were dissolved in 20mL anhydrous tetrahydrofuran. To this, 1.40 mL (9.69 mmol) of triethylamine and 265 mg (3.04 mmol) of lithium bromide were added. The reaction was stirred at room temperature under nitrogen. After 3 hours, the reaction was poured into 20 mL of 1N hydrochloric acid and 20 mL of ethyl acetate. The aqueous phase was washed with an additional 20 mL of ethyl acetate. The organic washes were combined and washed with 15 mL of brine. The organic layer was dried over magnesium sulfate and freed of solvent to give 0.70 g crude material. This material was recrystallized from 2:1 ethyl acetate/hexane to give 0.23 g of the title compound: MS (FAB) m/e: M+K= 1037, 1039, M+H=999, 1001; 13 C NMR (75 MHz) delta (selected signals) 167.6, 141.7, 135.8, 129.4, 128.9, 63.1, 62.9, 51.8, 50.4; IR (KBr) Cm$^{-1}$ 3430, 2930, 1745, 1650, 1450, 1090.

Examples 388a and 388b: Formula III: R=ethyl;
R'=H; n=1; $R^{31}=R^{32}=R^{34}=H$; $R^{35}$ and $R^{36}$ taken together form =NMe(O)(E- and Z-Configurations)

Ascomycin (15 g), triethylamine (9.1 g) and N-methylhydroxylamine hydrogen chloride (7.5 g) in ethanol (60 mL)

were stirred at 45° C. for 60 hours. Solvent was removed in vacuo and the product purified on silica gel eluting with t 0% ethanol/dichloromethane.

Title compound of Example 388a: Yield: 10.2 g; MS(FAB) m/z: M+K=859.

Title compound of Example 388b: Yield: 3.5 g; MSCFAB) m/z: M+K=859.

Example 405: Formula I: R=ethyl; R'=H; n=1; $R^2=R^{2'}=H$; $R^3$ and $R^4$ taken together form =NOH A solution of the product of Example 48 (0.25 g), hydroxylamine hydrochloride (0.03 g) and 4-methylmorpholine (0.035 g) in absolute ethanol (1 mL) was stirred at room temperature for 2 hours. Solvent was removed in vacuo and the product was purified on silica gel with ether elution. Yield: 0.2 g; MS(FAB) m/z: M+H=805.

Example 406: Formula V: R=ethyl; R'=H; n=1; $R^2=R^{2'}=H$; $R^3$ and $R^4$ taken together form =NOH; $R^{33}$=tert-butyldimethylsilyloxy: $R^{34}=R^{35}$ and $R^{36}$ taken together form an oxo group A solution of the product of Example 283 (0.52 g), hydroxylamine hydrochloride (0.05 g) and 4-methylmorpholine (0.1 mL) in absolute ethanol (3 mL) was stirred at room temperature for 1 hour. Solvent was removed in vacuo and the product was purified on silica gel with 20% acetone/hexanes elution. Yield: 0.5 g; MS(FAB) m/z: M+K=957.

Example 407: Formula V: R=ethyl; R'=H; n=1; $R^2=R^{2'}=H$; $R^3$ and $R^4$ taken together form =$NOSO_2Me$; $R^{33}$=tert-butyldimethylsilyloxy; $R^{34}$=H; $R^{35}$ and $R^{36}$ taken together form an oxo group The product of Example 406 (2.01 g) and triethylamine (0.3 mL) was dissolved in dry dichloromethane (15 mL) and cooled to 0° C. with ice-water bath. Methanesulfonyl chloride (0.52 g) was added and the reaction stirred for 0.5 hour. At the end of the reaction, the whole mixture was poured onto a column of silica gel (50 g) in 37.5% acetone/hexanes and eluted with 37.5% acetone/hexanes. Yield: 1.9 g.

Example 408: Formula V; R=ethyl; R'=H; n=1; $R^5$=formyl; $R^{31}=R^{32}$=H; $R^{33}$=t-butyldimethylsilyloxy: $R^{34}$=H; $R^{35}$ and $R^{36}$ taken together form an oxo group The product of Example 406 (1.0 g) and methylamine (0.3 mL) was dissolved in dry dichloromethane (4 mL) and cooled to 0° C. with ice-water bath. Methanesulfonyl chloride (0.17 mL) was added and reaction stirred for 0.5 hour. A solution of acetonitrile (5 mL) containing 38% aq HCl (0.5 mL) was added and the reaction mixture was heated at 50° C. for 0.5 hour. The reaction was partitioned between ether and water, the aqueous phase was further extracted with ether. The combined organic phase was washed once with brine, dried over magnesium sulfate and solvent removed in vacuo. Yield of the title compound: 0.06 g; MS(FAB) m/z: M+K=925. Yield: 0.11 g; MS(FAB) m/z: M+K =811.

Example 409: Formula III: R=ethyl; R'=H; n=1; $R^5$=formyl; $R^{31}$ and $R^{33}$ taken together form a bond: $R^{32}=R^{34}$=H; $R^{35}$ and $R^{36}$ taken together form an oxo group The title compound was isolated from the mixture of products of Example 408. Yield: 0.15 g; MS(FAB) m/z: M+K=793.

Example 410: Formula I: R=ethyl; R'=H; n=1: $R^5$=formyl

The title compound was prepared from the product of Example 408 (0.67 g) and hydrofluoric acid according to the procedure described in Example 412. Yield: 0.54 g; MS(FAB) m/z: M+K =811.

Example 411: Formula V: R=ethyl; R'=H; n=1; $R^5$=ethenyl; $R^{31}=R^{32}$=H; $R^{33}$=tert-butyldimethylsilyloxy; $R^{34}$=H; $R^{35}$ and $R^{36}$ taken together form an oxo group, 3'-propenyl; 2-cyanoethyl, 24-TBS Lithium bis(trimethylsilyl)amide (2.3 mL, 1.0M in tetrahydrofuran) was added into a suspension of methyltriphenylphosphonium bromide (0.97 g) in dry toluene (7 mL) at 0° C. and stirred for 40 minutes. A pre-cooled (−70°) solution of the product of Example 408 (0.73 g, in 14 mL of dry toluene) was added into the ylide over 7 minutes. After being stirred at 0° C. for 15 minutes, the reaction mixture was applied on a column of silica gel (50 g) in 20% acetone/hexanes and eluted with 20% acetone/hexane. Yield: 0.32 g; MS(FAB) m/z: M+K=923.

Example 412: Formula I: R=ethyl; R'=H; n=1: $R^5$=ethnyl

Hydrofluoric acid (48%, 0.24 mL) was added into a stirred solution of the product of Example 411 (0.191 g) in acetonitrile (6 mL) at 0° C. Cooling bath was removed after the addition. After being stirred at room temperature for 3 hours, the reaction was cooled in ice-water bath. Sodium bicarbonate (0.5 g) and powdered magnesium sulfate (1 g) were added and stirred at 0° C. for 45 minutes. Solids were filtered off and solvent removed in vacuo. The crude residue was purified by silica gel chromatography (20 g) eluting with 20% acetone/hexanes. Yield: 0.14 g; MS(FAB) m/z: M+K=809.

Example 413: Formula V: R=ethyl; R'=H; n=1; $R^5$methyl 2-carboxylethenyl; $R^{31}=R^{32}$=H; $R^{33}$=tert-butyldimethylsilyloxy: $R^{34}$=H; $R^{35}$ and $R^{36}$ taken together form an oxo group A solution of the product of Example 408 (1 g) and methyl (triphenylphosphoranylidene)acetate (1.13 g) in dry toluene (40 mL) was heated at 70° C. for 1 hour. Solids were filtered off and solvent removed in vacuo. The crude product was purified by silica gel chromatography (40 g) eluting with 20% acetone/hexanes. Yield: 1.0 g; MS(FAB) m/z: M+K= 981.

Example 414: Formula I: R=ethyl; R'=H; n=1; $R^5$=methyl 2-carboxylethenyl

The title compound was prepared from the product of Example 413 (0.57 g) according to the procedures described in Example 412. Yield: 0.32 g; MS(FAB) m/z: M+K=867.

Example 415: Formula I: R=ethyl; R'=H; n=1; $R^5$=2-phenylethenyl

The title compound is prepared from the product of Example 408 and benzyltriphenylphosphonium bromide and de-protected with hydrofluoric acid according to the procedures described in Examples 411 and 412.

Example 416: Formula V: R=ethyl; R'=H; n=1;
$R^5$N,N-dimethylhydrazone of formyl; $R^{31}=R^{32}$=H;
$R^{33}$=tert-butyldimethylsilyloxy: $R^{34}$=H; $R^{35}$ and
$R^{36}$ taken together form an oxo group 1,1-Dimethylhydrazine (0.055 mL, in 3 mL of dry tetrahydrofuran) was added into a stirred mixture of the title compound of Example 408 (0.56 g) and powdered magnesium sulfate (1 g) in dry tetrahydrofuran (4 mL) at 0° C. After being stirred at 0° C. for 2 hours, solvent was removed in vacuo and crude solid purified by silica gel chromatography (40 g) eluting with 2% isopropanol/dichloromethane. Yield: 0.40 g: MS(FAB) m/z: M+K=967.

Example 417: Formula I: R=ethyl; R'=H; n=1;
$R^5$=N,N-dimethylhydrazone of formyl Hydrofluoric acid (48%, 0.24 mL) was added into a stirred solution of the product of Example 416 (0.25 g) in acetonitrile (6 mL) at 0° C. Cooling bath was removed after the addition. After being stirred at room temperature for 3 hours, the reaction was cooled in an ice-water bath. Sodium bicarbonate (0.5 g) and powdered magnesium sulfate (1 g) were added and stirred at 0° C. for 45 minutes. Solids were filtered off and solvent removed in vacuo. The crude residue was purified by silica gel chromatography (20 g) eluting with 2% isopropanol/dichloro-methane. Yield: 0.17 g; MS(FAB) m/z: M+K=853.

Example 418: Formula V: R=ethyl; R'=H; n=1;
$R^5$=oxime of formyl; $R^{31}=R^{32}$=H;
$R^{33}$=tert-butyldimethylsilyloxy; $R^{34}$=H; $R^{35}$ and
$R^{36}$ taken together form an oxo group 4-Methylmorpholine (0.134 mL) was added into a suspension of hydroxylamine hydrochloride (0.078 g) in absolute ethanol (5 mL) at room temperature. After the mixture turned homogeneous, the solution was cooled to 0° C. with ice-water bath. A solution containing the product of Example 408 (0.9 g) in absolute ethanol (5 mL) was added into the hydroxylamine solution at 0° C. At the end of the reaction, solvent was removed in vacuo and the product purified by silica gel chromatography (20 g) eluting with 20% acetone/hexanes. Yield: 0.79 g; MS(FAB) m/z: M+K= 940.

Example 419: Formula I: R=ethyl; R'=H; n=1;
$R^5$=oxime of formyl

The title compound (0.6 g) was prepared from the product of Example 418 and hydrofluoric acid according to the procedures described in Example 417. Yield: 0.36 g; MS(FAB) m/z: M+K=826.

Example 420: Formula V: R=ethyl; R'=H; n=1;
$R^5$=O-carboxymethyl oxime of formyl; $R^{31}=R^{32}$=H;
$R^{33}$=tert-butyldimethylsilyloxy: $R^{34}$=H; $R^{35}$ and
$R^{36}$ taken together form an oxo group 4-Methylmorpholine (0.16 mL) was added into a suspension of O-carboxymethylhydroxyl amine hydrogen chloride (0.103 g) in absolute ethanol (4 mL). The reaction mixture was heated to 80° C. until all the solids were dissolved. The resulting solution was cooled to 0° C. The product of Example 408 (0.65 g) in absolute ethanol (3 mL) was added into the hydroxylamine solution and stirred for 1 hour. Solvent was removed in vacuo and product purified by silica gel chromatography (75 g) eluting with 40% acetone-hexanes containing 0.1% acetic acid. Yield: 0.51 g; MS(FAB) m/z: M+K=998.

Example 421: Formula I: R=ethyl; R'=H; n=1;
$R^5$=O-carboxymethyl oxime of formyl The title compound was prepared from the product of Example 420 (0,53 g) according to the procedures described in Example 13, Yield: 0.5 g; MS(FAB) m/z: M+K=884.

Example 422: Formula V: R=ethyl; R'=H; n=1;
$R^2=R^{2'}$=H; $R^3$ and $R^4$ taken together form an oxo group: $R^{33}=R^{34}$=H; $R^{35}$ and $R^{36}$ taken together form an oxo group The title compound is prepared from the product of Example 380 by the Swern oxidation procedure described in Example 283.

Example 423: Formula V: R=ethyl; R'=H; n=1;
$R^2=R^{2'}$=H; $R^3$ *and* $R^4$ taken together form an oxime; $R^{33}=R^{34}$=H; $R^{35}$ and $R^{36}$ taken together form an oxo group The title compound is prepared from the product of Example 422 and hydroxylamine hydrochloride according to the procedures described in Example 406.

Example 424: Formula V: R=ethyl; R'=H; n=1;
$R^5$=hydroxymethyl; $R^{31}=R^{32}$=H;
$R^{33}$=tert-butyldimethylsilyloxy: $R^{34}$=H; $R^{35}$ and
$R^{36}$ taken together form an oxo group Lithium tributoxyaluminum hydride (5 mL, 1M in tetrahydrofuran) was added into a solution of the product of Example 407 (1.9 g) in tetrahydrofuran (20 mL) cooled in dry ice-isopropanol bath. After being stirred for 2 hours at −70° C., excess hydride was destroyed by addition of ethanol (1 mL). The reaction was then partitioned between ether and 1N hydrochloride acid. The organic phase was washed once with brine, dried over magnesium sulfate and solvent removed in vacuo. The product was purified by silica gel chromatography (50 g) eluting with 20% acetone/hexanes. Yield: 1.1 g; MS(FAB) m/z: M+K=927.

Example 425: Formula I: R=ethyl; R'=H; n=1;
$R^5$hydroxymethyl

A solution of 48% hydrofluoric acid (0.08 mL) in acetonitrile (5 mL) was added into a stirred solution of the product of Example 424 (0.5 g) in acetonitrile (3 mL) at 0° (2. The reaction was stirred at room temperature for 2 hours after the addition. It was then cooled in ice-water bath and powdered sodium bicarbonate (0.5 g) was added to the reaction. After being stirred at 0 ° C. for 0.5 hour, the reaction mixture was poured on to a column containing silica gel (10 g) in 37% acetone-hexanes and eluted with the same solvent. The solid was further purified by silica gel chromatography (25 g) eluting with 37% acetone/hexanes. Yield: 0.345 g; MS(FAB) m/z: M+K=813.

Example 426: Formula V: R=ethyl; R'=H; n=1;
$R^5$methoxymethyl; $R^{31}=R^{32}$=H;
$R^{33}$=tert-butyldimethylsilyloxy; $R^{34}$=H; $R_{35}$ and
$R^{36}$ taken together form an oxo group Diazomethane (10 mL, 1M in ether) was added dropwise into a solution of the product of Example 424 (0.9 g) in ether (10 mL) containing catalytic amount of boron trifluoride etherate and silica gel. Solvent was removed by a slow stream of nitrogen and product purified by silica gel chromatography (20 g) eluting with ether. Yield: 0.45 g; MS(FAB) m/z: M+K=941.

Example 427: Formula V: R=ethyl; R'=H; n=1;
R$^5$allyloxymethyl; R$^{31}$=R$^{32}$=H;
R$^{33}$=tert-butyldimethylsilyloxy: R$^{34}$=H; R$^{35}$ and
R$^{36}$ taken together form an oxo group Silver (I) oxide (3.92 g) was added into a solution of the product of Example 424 (2.5 g) and allyl iodide (2 mL) in acetonitrile (25 mL) at 0° C. After being stirred at room temperature for 63 hours, the reaction mixture was poured on to a column containing silica gel (10 g) in 50% acetone/hexanes and eluted with the same solvent. The crude product was further purified by silica gel chromatography (250 g) eluting with 20% acetone/hexane. Yield: 1.52 g.

Example 428: Formula I: R=ethyl; R'=H; n=1;
R$^5$=2,3-dihydroxypropyloxymethyl

4-Methylmorpholine N-oxide (0.73 g) and osmium tetraoxide (1 mL, 4 wt % in water) were added into a stirred solution of the product of Example 436 (0.73 g) in tetrahydrofuran (52 mL) and stirred at room temperature for 5 hours. Excess oxidizing agent was quenched with sodium bisulfite (0.86 g) and florisil. The reaction was diluted with ethyl acetate and solid filtered off through celite. The filtrate was washed with 1N sodium bicarbonate, brine, dried over magnesium sulfate and solvent removed in vacuo. The product was purified by silica gel chromatography (100 g) eluting with 40% acetone/hexanes. Yield: 0.46 g; MS(FAB) m/z: M+K=887.

Example 429: Formula I: R=ethyl; R'=H; n=1;
R$^5$=ethyloxymethyl

The title compound is prepared from the product of Example 424 and ethyl iodide according to the procedures de,scribed in Example 427 and deprotected according to the procedures described in Example 436.

Example 430: Formula I: R=ethyl; R'=H; n=1;
R$^5$=ethyl carboxymethoxymethyl

The title compound is prepared from the product of Example 424 and ethyl diazoacetate according to the procedures described in Example 427 and deprotected according to the procedures described in Example 436.

Example 431: Formula V; R=ethyl; R'=H; n=1;
R$^5$=phenoxymethyl; R$^{31}$=R$^{32}$=H;
R$^{33}$=tert-butyldimethylsilyloxy; R$^{34}$=H; R$^{35}$ and
R$^{36}$ taken together form an oxo group Triphenylphosphine (0.3 g) and phenol (0.11 g) were added into a solution of the product of Example 424 (1.0 g) in dry tetrahydrofuran (6 mL) at 0° C. Diethyl acetylenedicarboxylate (0.177 mL) was added dropwise and the reaction stirred at 0° C. for 0.5 hour then at room temperature for 1 hour. Solvent was removed in vacuo and the solid residue was triturated with 50% ether/hexanes. The filtrate was partitioned between ether and 1N sodium hdyroxide. The organic phase was washed with brine, dried over magnesium sulfate and solvent removed. The product was purified by silica gel chromatography (100 g)eluting with 20% acetone/hexanes. Yield: 0.88 g; MS(FAB) m/z: M+K=1003.

Example 432: Formula V; R=ethyl; R'=H; n=1;
R$^5$=benzyloxymethyl; R$^{31}$=R$^{32}$=H;
R$^{33}$=tert-butyldimethylsilyloxy; R$^{34}$=H; R$^{35}$ and
R$^{36}$ taken together form an oxo group Silver (I) oxide (1.5 g) was added into a solution of the product of Example 424 (1.0 g) benzyl bromide (0.8 mL) and potassium iodide (0.05 g) in dimethylformamide (10 mL) at 0° C. After being stirred at room temperature for 6 hours, the reaction mixture was partitioned between ether and water. The organic phase was washed with brine, dried over magnesium sulfate and solvent removed in vacuo. The crude product was further purified by silica gel chromatography (100 g) eluting with 20% acetone/hexanes. Yield: 0.4 g; MS(FAB) m/z: M+K=1017.

Example 433: Formula I: R=ethyl; R'=H; n=1;
R$^5$=4-pyridyloxymethyl

The title compound is prepared from the product of Example 424 and 4-hydroxypyridine according to the procedures described in Examples 431 and 437.

Example 434: Formula I: R=ethyl; R'=H; n=1;
R$^5$=4-pyridylmethyloxymethyl

The title compound is prepared from the product of Example 424 and 4-bromomethylpyridine according to the procedures described in Examples 432 and 438.

Example 435: Formula I: R=ethyl; R'=H; n=1;
R$^5$=methoxymethyl

The title compound was prepared from the product of Example 426 (0.4 g) and hydrofluoric acid according to the procedures described in Example 425. Yield: 0.3 g; MS(FAB) m/z: M+K=827.

Example 436: Formula I: R=ethyl; R'=H; n=1;
R$^5$=3-allyloxymethyl

The title compound was prepared from the product of Example 427 (0.4 g) and hydrofluoric acid according to the procedures described in Example 425. Yield: 0.35 g; MS(FAB) m/z: M+K=853.

Example 437: Formula I: R=ethyl; R'=H; n=1;
R$^5$=phenoxymethyl

The title compound was prepared from the product of Example 431 (0.85 g) and hydrofluoric acid according to the procedures described in Example 436. Yield: 0.74 g; MS(FAB) m/z: M+K=889.

Example 438: Formula I: R=ethyl; R'=H; n=1;
R$^5$=benzyloxymethyl

The title compound was prepared from the product of Example 432 (0.4 g) and hydrofluoric acid according to the procedures described in Example 436. Yield: 0.35 g; MS(FAB) m/z: M+K=903.

Example 439: Formula V: R=ethyl; R'=H; n=1;
R$^2$=R$^{2'}$=H; R$^3$ and R$^4$taken together form
=N—OSO$_2$Me: R$^{33}$=R$^{34}$=H; R$^{35}$ and R$^{36}$ taken
together form an oxo group The title compound is prepared from the product of Example 423 and methanesulfonyl chloride according to the procedures described in Example 407.

Example 440: Formula V; R'=ethyl; R'=H; n=1;
R$^5$formyl; R$^{31}$=R$^{32}$=H; R$^{33}$=R$^{34}$ =H; R$^{35}$ and R$^{36}$
taken together form an oxo group The title compound is prepared from the product of Example 439 according to the procedures described in Example 408.

Example 441: Formula V: R=ethyl; R'=H; n=1; R$^5$=ethenyl; R$^{31}$=R$^{32}$=H; R$^{33}$=R$^{34}$=H; R$^{35}$ and R$^{36}$ taken together form an oxo group The title compound is prepared from the product of Example 440 and methyltriphenylphosphonium bromide according to the procedures described in Example 411.

Example 442: Formula V: R=ethyl; R'=H; n=1; R$^5$methyl2-carboxyethenyl; R$^{31}$=R$^{32}$=H; R$^{33}$=R$^{34}$=H; R$^{35}$ and R$^{36}$ taken together form an oxo group The title compound is prepared from the product of Example 440 and methyl (triphenylphosphoranylidene)acetate according to the procedures described in Example 411.

Example 443: Formula V: R=ethyl; R'=H; n=1; R$^5$=2-phenyl-ethenyl; R$^{31}$=R$^{32}$=H; R$^{33}$=R$^{34}$=H; R$^{35}$ and R$^{36}$ taken together form an oxo group The title compound is prepared from the product of Example 440 and benzyltriphenylphosphonium bromide according to the procedures described in Example 411.

Example 444: Formula V: R=ethyl; R'=H; n=1; R$^5$=N,N-dimethylhydrazone of formyl; R$^{31}$=R$^{32}$=H; R$^{33}$=R$^{34}$=H; R$^{35}$ and R$^{36}$ taken together form an oxo group The title compound is prepared from the product of Example 440 and N,N-dimethythydrazine according to the procedures described in Example 417.

Example 445: Formula V: R=ethyl; R'=H; n=1; R$^5$=N-tetrazoylmethyl; R$^{31}$=R$^{32}$=H; R$^{33}$=tert-butyldimethylsilyloxy: R$^{34}$=H; R$^{35}$ and R$^{36}$ taken together form an oxo group Triphenylphosphine (0.7 g) and tetrazole (0.19 g) were added into a solution of the product of Example 424 (0.8 g) in dry tetrahydrofuran (6 mL) at 0° C. Diethyl acetylenedicarboxylate (0.425 mL) was added dropwise and the reaction stirred at 0° C. for 0.5 hour then at room temperature for 1 hour. Solvent was removed in vacuo and the solid residue was triturated with 50% ether/hexanes. The filtrate was partitioned between ether and 1N sodium hdyroxide. The organic phase was washed with brine, dried over magnesium sulfate and solvent removed. The product was purified by silica gel chromatography (100 g) eluting with 20% acetone/hexanes. Yield: beta-tetrazole, 0.5 g; MS(FAB) m/z: M+K= 979; alpha-tetrazole, 0.07 g; MS(FAB) m/z: M+NH$_4$=958.

Example 446: Formula I: R=ethyl; R'=H; n=1; R$^5$=N-tetrazoylmethyl

The title compound was prepared from the product (beta-tetrazole) of Example 445 (0.47 g) and hydrofluoric acid according to the procedures described in Example 436. Yield: 0.38 g; MS(FAB) m/z: M+K=865.

Example 447: Formula V: R=ethyl; R'=H; n=1; R$^5$=methanesulfonyloxymethyl; R$^{31}$=R$^{32}$=H; R$^{33}$=tert-butyldimethylsilyloxy: R$^{34}$=H; R$^{35}$ and R$^{36}$ taken together form an oxo group Methanesulfonyl chloride (0.125 mL) was added dropwise into a stirred solution of the product of Example 424 (0.72 g) and triethylamine (0.225 mL) in dry dichloromethane (3 mL) at 0° C. After being stirred at 0° C. for 15 minutes, the reaction mixture was poured on to a column containing silica gel (20 g) eluting with 50% acetone/hexanes. Yield: 0.64 g; MS(FAB) m/z: M+K=1005.

Example 448: Formula V: R=ethyl; R'=H; n=1; R$^5$=N-(2-nitroimidazolyl)methyl; R$^{31}$=R$^{32}$=H; R$^{33}$=tert-butyldimethylsilyloxy; R$^{34}$=H; R$^{35}$ and R$^{36}$ taken together form an oxo group 2-Nitro-imidazole (1 mmol) is added into a solution of the product of Example 447 (1 mmol) and triethylamine (1 mmol) in dimethylformamide (1 mL) and stirred at room temperature for 24 hours. The reaction mixture is partitioned between ether and water. The organic phase is washed with brine, dried over magnesium sulfate and solvent removed in vacuo. The product is purified by silica gel chromatography.

Example 449: Formula I: R=ethyl; R'=H; n=1; R$^5$N-(2-nitroimidazolyl)methyl

The title compound is prepared from the product of Example 448 and hydrofluoric acid according to the procedures described in Example 436.

Example 450: Formula V: R=ethyl; R'=H; n=1; R$^5$=4-morpholinomethyl; R$^{31}$=R$^{32}$=H; R$^{33}$=tert-butyldimethylsilyloxy; R$^{34}$=H; R$^{35}$ and R$^{36}$ taken together form an oxo group The title compound is prepared from the product of Example 447 and morpholine according to the procedures described in Example 448.

Example 451: Formula I: R=ethyl; R'=H; n=1; R$^5$=4-morpholinomethyl

The title compound is prepared from the product of Example 450 and hydrofluoric acid according to the procedures described in Example 436.

Example 452: Formula V: R=ethyl; R'=H; n=1; R$^5$=4-methylpiperazinemethyl; R$^{31}$=R$^{32}$=H; R$^{33}$=tert-butyldimethylsilyloxy; R$^{34}$=H; R$^{35}$ and R$^{36}$ taken together form an oxo group The title compound is prepared from the product of Example 447 and 4-methylpiperazine according to the procedures described in Example 448.

Example 453: Formula I: R=ethyl; R'=H; n=1; R$^5$=4-methylpiperazinemethyl

The title compound is prepared from the product of Example 452 and hydrofluoric acid according to the procedures described in Example 436.

Example 454: Formula V: R=ethyl; R'=H; n=1; R$^5$=azidomethyl; R$^{31}$=R$^{32}$=H; R$^{33}$=tert-butyldimethylsilyloxy; R$^{34}$=H; R$^{35}$ and R$^{36}$ taken together form an oxo group A solution of diphenylphosphoryl azide (1 mmol) and the product of Example 424 (1 mmol) in tetrahydrofuran (10 mL) is heated to 50° C. for 24 hours. The product is purified by silica gel chromatography.

Example 455: Formula I: R=ethyl; R'=H; n=1;
R$^5$=azidomethyl

The title compound is prepared from the product of Example 454 and hydrofluoric acid according to the procedures described in Example 436.

Example 456: Formula I: R=ethyl; R'=H; n=1;
R$^5$=aminomethyl

A solution of triphenylphosphine and the product of Example 455 in wet toluene is heated at 80° C. for 6 hours. The product is purified by silica gel chromatography.

Example 457: Formula V: R=ethyl; R'=H: n=1;
R$^5$=carboxymethyl; R$^{31}$=R$^{32}$=H;
R$^{33}$=tert-butyldimethylsilyloxy; R$^{34}$=H; R$^{35}$ and R$^{36}$ taken together form an oxo group The title compound is prepared by the Mitsunobu reaction of the product of Example 424 and Meldrum's acid according to the procedure described in Examples 431 and 437 followed by decarboxylation.

Example 458: Formula I: R=ethyl; R'=H; n=1;
R$^5$=carboxymethyl

The title compound is prepared from the product of Example 457 and hydrofluoric acid according to the procedures described in Example 436.

Example 459: Formula V: R=ethyl; R'=H; n=1;
R$^5$=cyanomethyl; R$^{31}$=R$^{32}$=H;
R$^{33}$=tert-butyldimethylsilyloxy; R$^{34}$=H; R$^{35}$ and R$^{36}$ taken together form an oxo group The title compound is prepared from the product of Example 447 and potassium cyanide according to the procedures described in Example 448.

Example 460: Formula I: R=ethyl; R'=H; n=1;
R$^5$=cyanomethyl

The title compound is prepared from the product of Example 459 and hydrofluoric acid according to the procedures described in Example 436.

Example 461: Formula I: R=ethyl; R'=H; n=1;
taken together R$^6$ and R$^7$ form an acetal of formula
—S—(CH$_2$)$_3$—S—

Hydrofluoric acid (48% 0.16 mL in 2 mL of acetonitrile) was added into a solution of the product of Example 407 (0.5 g) and 1,3-propanedithiol (0.06 mL) in dichloromethane (3 mL) containing silica gel (0.5 g) at 0° C. After being stirred at room temperature overnight, the reaction mixture was cooled to 0° C. Powdered sodium bicarbonate (1 g), charcoal, and magnesium sulfate (1.0 g) were added and stirred for 0.5 hour. Solids were faltered through celite and solvent was removed in vacuo. The product was purified by silica gel chromatography (30 g) eluting with 30% acetone/hexanes. Yield: 0.18 g; MS(FAB) m/z: M+K=901.

Example 462: Formula I: R=ethyl; R'=H; n=1:
taken together R$^6$ and R$^7$ form an acetal of formula
—S—(CH$_2$)$_2$—S—

The title compound is prepared from the product of Example 407 and 1,2-ethanedithiol according to the procedures described in Example 461.

Example 463: Formula I: R=ethyl; R'=H; n=1;
taken together R$^6$ and R$^7$ form an acetal of formula
—S—(1,2-phenyl)—S—

The title compound is prepared from the product of Example 407 and 1,2-benzenedithiol according to the procedures described in Example 461.

Example 464: Formula V: R=ethyl; R'=H; n=1;
R$^6$=R$^7$=ethoxy: R$^{31}$=R$^{32}$=H;
R$^{33}$=tert-butyldimethylsilyloxy; R$^{34}$=H; R$^{35}$ and R$^{36}$ taken together form an oxo group A solution of the product of Example 407 (0.1 g) in absolute ethanol (2 mL) was heated at 50° C. for 1 hour. Solvent was removed in vacuo and product purified by silica gel chromatography (30 g) eluting with 20% acetone/hexanes. Yield: 0.06 g; MS(FAB) m/z: M+K=999.

Example 465: Formula I: R=ethyl; R'=H; n=1;
R$^6$=R$^7$ethoxy

Hydrofluoric acid (48% 0.1 mL in 2 mL of acetonitrile) was added into a stirred solution of the product of Example 464 (0.1 g) in absolute ethanol (2 mL) at 0° C. After being stirred at room temperature for 2 hours, the reaction was partitioned between ether and 1N sodium bicarbonate. The organic phase was washed once with brine, dried over magnesium sulfate and solvent removed in vacuo. The product was purified by preparative TLC eluting with 30% acetone/hexanes. Yield: 0.04 g; MS(FAB) m/z.: M+K=885.

Example 466: Formula I: R=ethyl; R'=H; n=1;
taken together R$^6$ and R$^7$ form an acetal of formula
—O—(CH$_2$)$_2$—O—

The title compound is prepared from the product of Example 407 and ethylene glycol according to the procedures described in Example 461.

Example 467: Formula I: R=ethyl; R'=H; n=1:
taken together R$^6$ and R$^7$ form an acetal of formula
—O—(CH$_2$)$_3$—O—

The title compound is prepared from the product of Example 407 and 1,3-propanediol according to the procedures described in Example 461.

Example 468: Formula I: R=ethyl; R'=H; n=1;
taken together R$^6$ and R$^7$ form an acetal of formula
—O—(1,2-phenyl)—O—

The title compound is prepared from the product of Example 407 and catechol according to the procedures described in Example 461.

Example 469: Formula V; R=ethyl; R'= H; n=1;
R$^6$=methoxy: R$^7$=ethyl; R$^{31}$=R$^{32}$=H;
R$^{33}$=tert-butyldimethylsilyloxy; R$^{34}$=H; R$^{35}$ and R$^{36}$ taken together form an oxo group Methanesulfonyl chloride (1.48 g) was added dropwise into a solution of the product of Example 406 (1.4 g) and methylamine (0.7 mL) in dry dichloromethane (15 mL) at 0° C. The reaction mixture was cooled to −48° C. with dry ice-acetonitrile bath. Triethylaluminum (9.2 mL, 1M in hexanes) was added and stirred at this temperature for 6 hours. The reaction was partitioned between ether and 1N hydrochloric acid. The organic phase was washed with brine, dried over magnesium sulfate and solvent removed in vacuo. The product was purified by silica gel chromatography (22 g) eluting with 10% acetone/hexanes. Yield: 0.78 g; MS(FAB) m/z: M+K=969.

Example 470: Formula I: R=ethyl; R'=H; n=1; $R^6$=methoxy; $R^7$=ethyl

The title compound was prepared from the product of Example 469 (0.54 g) and hydrofluoric acid according to the procedure described in Example 436. Yield: 0.3 g; MS(FAB) m/z: M+K=855.

Example 471: Formula V: R=ethyl; R'=H; n=1; $R^6$=methoxy; $R^7$=methyl; $R^{31}$=$R^{32}$=H; $R^{33}$=tert-butyldimethylsilyloxy; $R^{34}$=H; $R^{35}$ and $R^{36}$ taken together form an oxo group The title compound is prepared from the product of Example 406 and trimethylaluminum according to the procedure described in Example 469.

Example 472: Formula I: R=ethyl; R'=H: n=1; $R^6$=methoxy; $R^7$=methyl

The title compound is prepared from the product of Example 471 and hydrofluoric acid according to the procedure described in Example 436.

Example 473: Formula V: R=ethyl; R'=H; n=1; $R^6$=methoxy; $R^7$=n-propyl; $R^{31}$=$R^{32}$=H; $R^{33}$=tert-butyldimethylsilyloxy; $R^{34}$=H; $R^{35}$ and $R^{36}$ taken together form an oxo group The title compound is prepared from the product of Example 406 and tri-n-propylaluminum according to the procedure described in Example 469.

Example 474: Formula I; R=ethyl; R'=H; n=1; $R^6$=methoxy; $R^7$=n-propyl

The title compound is prepared from the product of Example 473 and hydrofluoric acid according to the procedure described in Example 436.

Example 475: Formula I; R=ethyl: R'=H; n=1; $R^2$=$R^{2'}$=H; $R^3$ and $R^4$ taken together form =N(O)Me A solution of the product of Example 283 (1.08 g), N-methylhydroxyl amine hydrochloride (0.18 g) and triethylamine (0.59 mL) in absolute ethanol (5 mL) was stirred at room temperature for 6 hours. Solvent was removed in vacuo. The product was purified by silica gel chromatography (100 g) eluting with 10% ethanol/dichloromethane. Yield: 1.19 g; MS(FAB) m/z: M+K=857.

Example 476: Formula I: R=ethyl; R'=H; n=1; $R^2$=$R^{2'}$=H; $R^3$ and $R^4$ taken together form =N(O)Benzyl The title compound is prepared from the N-benzylhydroxylamine hydrochloride and the product of Example 283 according to the procedures described in Example 475.

Example 477: Formula I: R=ethyl; R'=H; n=1; $R^2$=$R^{2'}$=H; $R^3$ and $R^4$ taken together form =N(O)Me The title compound is prepared from the O-methylhydroxylamine hydrochloride and the product of Example 283 according to the procedures described in Example 475.

Example 478: Formula I: R=ethyl; R'=H; n=1; $R^2$=$R^{2'}$=H; $R^3$ and $R^4$ taken together form =N(O)Benzyl The title compound is prepared from the O-benzylhydroxylamine hydrochloride and the product of Example 283 according to the procedures described in Example 71.

Example 479: Formula I: R=ethyl; R'=H; n=1; $R^2$=$R^{2'}$=H; $R^3$ and $R^4$ taken together form =N(O)Et The title compound is prepared from the N-ethylhydroxylamine hydrochloride and the product of Example 283 according to the procedures described in Example 475.

Example 480: Formula V: R=ethyl; R'=H; n=1; $R^5$=hydroxymethyl; $R^{31}$=$R^{32}$=H; $R^{33}$=$R^{34}$=H; $R^{35}$ and $R^{36}$ taken together form an oxo group The title compound is prepared from the product of Example 439 and lithium tri-tert-butyoxy aluminum hydride according to the procedures described in Example 424.

Example 481: Formula V; R=ethyl; R'=H; n=1; $R^5$=methoxymethyl; $R^{31}$=$R^{32}$=H; $R^{33}$=$R^{34}$=H; $R^{35}$ and $R^{36}$ taken together form an oxo group The title compound is prepared from the product of Example 480 and diazomethane according to the procedures described in Example 426.

Example 482: Formula V: R=ethyl; R'=H; n=1; $R^5$=allyloxymethyl; $R^{31}$=$R^{32}$=H; $R^{33}$=$R^{34}$=H; $R^{35}$ and $R^{36}$ taken together form an oxo group The title compound is prepared from the product of Example 480 and allyl iodide according to the procedures described in Example 427.

Example 483: Formula V: R=ethyl; R'=H; n=1; $R^5$=benzyloxymethyl; $R^{31}$=$R^{32}$=H; $R^{33}$=$R^{34}$=H; $R^{35}$ and $R^{36}$ taken together form an oxo group The title compound is prepared from the product of Example 480 and benzyl bromide according to the procedures described in Example 432.

Example 484: Formula V: R=ethyl; R'=H; n=1; $R^5$=2,3-dihydroxypropyloxymethyl; $R^{31}$=$R^{32}$=H; $R^{33}$=$R^{34}$=H; $R^{35}$ and $R^{36}$ taken together form an oxo group The title compound is prepared from the product of Example 482 and osmium tetraoxide according to the procedures described in Example 428.

Example 485: Formula V: R=ethyl; R'=H; n=1; $R^5$=phenoxymethyl; $R^{31}$=$R^{32}$=H; $R^{33}$=$R^{34}$=H; $R^{35}$ and $R^{36}$ taken together form an oxo group The title compound is prepared from the product of Example 480 and phenol by a Mitsunobu reaction according to the procedures described in Example 431.

Example 486: Formula V: R=ethyl; R'=H; n=1; R⁵=N-tetrazoylmethyl; R³¹=R³²=H; R³³=R³⁴=H; R³⁵ and R³⁶ taken together form an oxo group The title compound is prepared from the product of Example 480 and tetrazole by a Mitsunobu reaction according to the procedures described in Example 431.

Example 487: Formula V: R=ethyl; R'=H; n=1; R⁵=methanesulfonyloxymethyl; R³¹=R³²=H; R³³=R³⁴=H; R³⁵ and R³⁶ taken together form an oxo group The title compound is prepared from the product of Example 480 and methanesulfonyl chloride according to the procedures described in Example 447.

Example 488: Formula V: R=ethyl; R'=H; n=1; R⁵=N-(2-nitroimidazoly)methyl; R³¹=R³²=H; R³³=R³⁴=H; R³⁵ and R³⁶ taken together form an oxo group The title compound is prepared from the product of Example 487 and 2-nitroimidazole according to the procedures described in Example 448.

Example 489: Formula V: R=ethyl; R'=H; n=1; R⁵=azidomethyl; R³¹=R³²=H; R³³=R³⁴=H; R³⁵ and R³⁶ taken together form an oxo group The title compound is prepared from the product of Example 487 and diphenylphosphoryl azide according to the procedures described in Example 454.

Example 490: Formula V: R=ethyl; R'=H; n=1; R⁵=N-morpholinomethyl: R³¹=R³²=H; R³³=R³⁴=H; R³⁵ and R³⁶ taken together form an oxo group The title compound is prepared from the product of Example 83 and morpholine according to the procedures described in Example 44.

Example 491: Formula V: R=ethyl; R'=H; n=1; R²=R²'=H; R³ and R⁴ taken together form an oxime, R³³=R³⁴=H; R³⁵ and R³⁶ taken together form an oxo group The title compound is prepared from the product of Example 18 and N-methylhydroxylamine hydrochloride according to the procedure described in Example 2.

Example 492: In vivo Assay of Biolological Activity

The immunosuppressant activity of the compounds of the present invention was determined using the human mixed lymphocyte reaction (MLR) assay described by Kino, T. et al. in *Transplantation Proceedings,* XIX(5):36–39, Suppl. 6 (1987). The results of the assay, shown below in Table 1, demonstrate that the compounds tested are effective immunomodulators at sub-micromolar concentrations.

TABLE 1

| Ex. # | IC₅₀(M) |
|---|---|
| 417 | <1 × 10⁻⁶ |
| 419 | <1 × 10⁻⁶ |
| 421 | <1 × 10⁻⁶ |
| 425 | <1 × 10⁻⁶ |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

We claim:

1. A compound having the formula

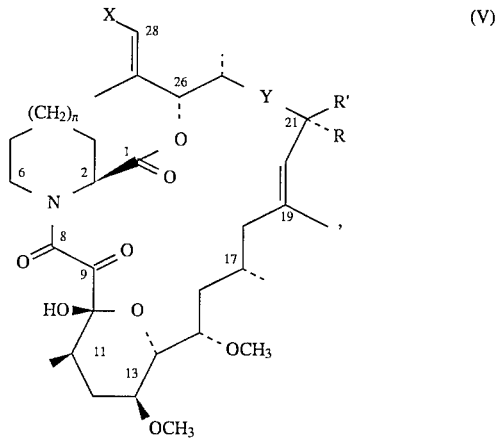

(V)

wherein n is zero or one;

R and R' are chosen such that (a) one of R and R' is hydrogen and the other is selected from the group consisting of methyl, ethyl, 2-hydroxyethyl, propyl, cyclopropylmethyl, 2-oxopropyl, 2-ethanal, allyl, —CH₂CH₂OC(O)R¹⁰ where R¹⁰ is aryl, —CH₂C(O)R¹², —CH₂C(O)N(R¹⁴')(CH₂)ₘCH(R¹⁶)—C(O)R¹², —CH₂C(O)N(R¹⁴')(CH₂)ₘCH(R¹⁶)C(O)—N(R¹⁴")(CH₂)ₘ'CH(R¹⁶')C(O)R¹², and —CH²C(O)N(R¹⁴')(CH₂)ₘCH(R¹⁶)C(O)N(R¹⁴")(CH₂)ₘ'CH(R¹⁶')C(O)—N(R¹⁴''')(CH₂)ₘ''CH(R¹⁶'')C(O)R¹², wherein m, m' and m" are independently zero to six; R¹⁶, R¹⁶' and R¹⁶" are independently selected from hydrogen, C₁-to-C₈-loweralkyl, hydroxy-C₁-to-C₈-loweralkyl, carboxy-C₁-to-C₈-alkyl, thio-C₁-to-C₈-loweralkyl, thio-C₁-to-C₈-alkoxy-C₁-to-C₁₂-alkyl, guanidino-C₁-to-C₈-alkyl, amino-C₁-to-C₈-alkyl, aryl-C₁-to-C₁₂-alkyl and, if m, m' and m" are other than zero, amino or amido-C₁-to-C₈-alkyl; and R¹² is selected from (i) hydroxy, (ii) —OR¹³ where R¹³ is C₁-to-C₈-loweralkyl, C₃-to-C₈-cycloalkyl, C₃-to-C₈-cycloalkyl-C₁-to-C₁₂-alkyl or aryl-C₁-to-C₁₂-alkyl, and (iii) —NR¹⁴R¹⁵ wherein R¹⁴, R¹⁴', R¹⁴" and R¹⁴''' are independently selected from hydrogen, C₁-to-C₈-loweralkyl, aryl-C₁-to-C₁₂-alkyl, C₃-to-C₈-cycloalkyl and C₃-to-C₈-cycloalkyl-C₁-to-C₁₂-alkyl and R¹⁵ is selected from hydrogen, C₁-to-C₈-loweralkyl, aryl-C₁-to-C₁₂-alkyl, C₃-to-C₈-cycloalkyl, C₃-to-C₈-cycloalkyl-C₁-to-C₁₂-alkyl, amino-C₁-to-C₈-alkyl, hydroxy-C₁-to-C₈-alkyl, carboxy-C₁-to-C₈-alkyl, and thio-C₁-to-C₈-loweralkyl; or, taken together, R¹⁴ and R¹⁵ are —(CH₂)_q— where q is two to five; or, taken together with the nitrogen to which they are attached, R¹⁴ and R¹⁵ form a group selected from morpholino and piperidino; or, taken together, one or more of R¹⁴' and R¹⁶, R¹⁴" and R¹⁶', and R¹⁴''' and R¹⁶'' are —(CH₂)_p— where p is two to five, or (b) one of R and R', taken together with one of $R^{35}$ and $R^{36}$, forms a C-21/C-22 bond and the other of R and R', taken together with the other of $R^{35}$ and $R^{36}$, is a heterocycle-forming group having a formula selected from $-N(R^{63})CH=CH-$ and $-OC(R^{64})=CH-$ where the heteroatom in each instance is connected to C-22, $R^{63}$ is selected from hydrogen, $C_1$-to-$C_8$-loweralkyl, aryl-$C_1$-to-$C_{12}$-alkyl and aryl, and $R^{64}$ is hydrogen or $C_1$-to-$C_8$-loweralkyl;

X is a group having the formula

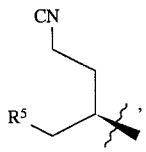
(Ic)

wherein $R^5$ is selected from the group consisting of hydrogen, methyl, formyl, amino, aminomethyl, $-CH=CH_2$, $-CH_2OH$, $-CHR^6 R^7$, $-C(O)NHR^{63}$, $-C(O)N(CH_3)R^{63}$, $-CH_2NHC(O)R^{63}$, $-CH_2N(CH_3)C(O)R^{63}$, $-CH_2OR^{201}$, $-CH=NOH$, $-CH=NNR^{201}R^{202}$, $-CH=NNHC(NH)NH_2$, $-CH=NOR^{201}$, $-CH=NOCH_2C(O)OH$, $-C(O)OR^{203}$, $-C(O)NR^{203}R^{204}$, $-CH_2F$, $-CH_2Cl$, $-CH_2Br$, $-CH_2N_3$, $-CH=CR^{205}R^{206}$, $-CH_2SR^{201}$, $-CH_2OR^{208}$, $-CH_2OCH_2CHCH_2$, $-CH_2OCH_2CH(OH)CH_2OH$, $-CH_2OC(O)R^{201}$, $-CH_2OC(O)NHR^{201}$, $-CH_2O$-(tert-butyldimethylsilyl), $-CH_2OCH_2OR^{201}$, $-CH(R^{204})OH$, $-CH(R^{204})OR^{201}$, $-NHR^{201}$, $-NR^{201}R^{205}$, $-NH-C(O)R^{203}$, $-N(CH_3)C(O)R^{203}$, and a radical selected from the group consisting of

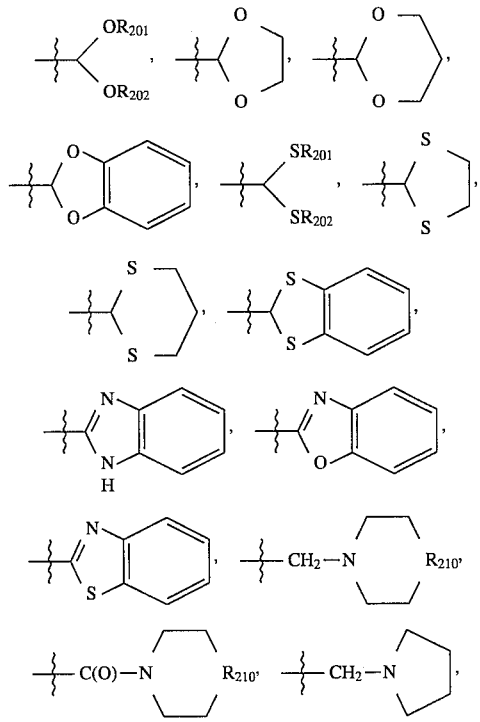

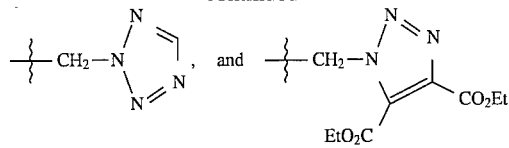

where $R^6$ and $R^7$ are (a) independently selected from the group consisting of thio-$C_1$-to-$C_8$-loweralkoxy, thioaryl-$C_1$-to-$C_{12}$-alkoxy, $C_1$-to-$C_8$-loweralkoxy and aryl-$C_1$-to-$C_{12}$-alkoxy, or (b) taken together, $R^6$ and $R^7$ form an acetal-forming moiety having the formula $-S-(CH_2)_g-S-$, $-O-(CH_2)_g-O-$, $-O-(1,2$-phenyl)-O$-$ or $-S-(1,2$-phenyl)-S$-$, where g is two, three or four; $R^{63}$ is selected from the group consisting of hydrogen, $C_1$-to-$C_8$-loweralkyl, aryl-$C_1$-to-$C_{12}$-alkyl and aryl; $R^{201}$ and $R^{202}$ are independently selected from the group consisting of hydrogen, $C_1$-to-$C_6$ loweralkyl and phenyl-substituted $C_1$-to-$C_6$ loweralkyl; $R^{203}$ is selected from the group consisting of hydrogen, $C_1$-to-$C_6$ loweralkyl, phenyl-substituted $C_1$-to-$C_6$ loweralkyl, hydroxy-substituted $C_2$-to-$C_6$ loweralkyl, piperid-1-yl-substituted $C_2$-to-$C_6$ loweralkyl and morphol-4-yl-substituted $C_2$-to-$C_6$ loweralkyl; $R^{204}$ is selected from the group consisting of hydrogen and $C_1$-to-$C_6$ loweralkyl; $R^{205}$ and $R^{206}$ are independently selected from the group consisting of hydrogen, $C_1$-to-$C_8$-loweralkyl and $-C(O)OR^{207}$ where $R^{207}$ is $C_1$-to-$C_6$ loweralkyl; $R^{208}$ is selected from the group consisting of phenyl and phenyl substituted with a radical selected from halogen, hydroxy, amino, nitro and $R^{203}$; and $R^{210}$ is selected from the group consisting of $-CH_2-$, $-O-$ and $-N(R^{203})-$; and Y is a group having a structural formula selected from

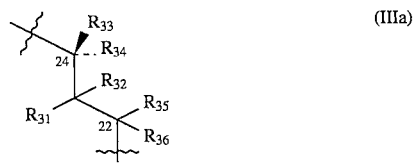
(IIIa)

and

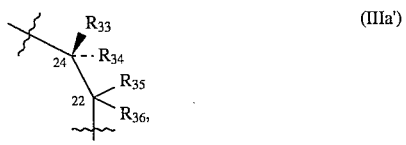
(IIIa')

wherein (a) $R^{31}$ and $R^{32}$ are chosen such that one of $R^{31}$ and $R^{32}$ is hydrogen and the other is independently selected from the group consisting of (i) hydrogen, and (ii) hydroxy;

or, taken together, $R^{31}$ and $R^{32}$ form a diazo group;

or, taken together with one of $R^{33}$ and $R^{34}$, one of $R^{31}$ and $R^{32}$ forms a C-23/C-24 bond and the other is selected from the group consisting of hydrogen, $C_1$-to-$C_{12}$-alkyl, $-C(O)NHR^{61}$, $-S(O)_2R^{61}$ and $-C(O)OR^{61}$, where $R^{61}$ is hydrogen, aryl or $C_1$-to-$C_8$-loweralkyl;

or, taken together with one of $R^{35}$ and $R^{36}$, one of $R^{31}$ and $R^{32}$ forms a C-22/C-23 bond;

or $R^{31}$ and $R^{32}$, together with carbon atom C-23 to which they are attached, may be absent and replaced by a C-22/C-24 bond;

or, taken together with one or both of $R^{33}$ and $R^{34}$ and the carbon atoms to which they are attached, one or both of $R^{31}$ and $R^{32}$ form (i) a fused norbornene group, (ii) a fused indole group wherein the nitrogen atom is adjacent to C-24, or (iii) a fused pyrrole;

or, taken together with $R^{35}$ and $R^{36}$ and the carbon atoms to which they are attached, $R^{31}$ and $R^{32}$ form (i) a fused indole group wherein the nitrogen atom is adjacent to C-22 or (ii) a fused furan ring wherein the oxygen atom is adjacent to C-22;

(b) $R^{35}$ and $R^{36}$ are chosen such that both are $C_1$-to-$C_8$-loweralkoxy, or that one of $R^{35}$ and $R^{36}$ is hydrogen and the other is selected from hydroxy, amino, —OC(O)O-(benzyl) and —NHNH-(tosyl) or, taken together with one of $R^{31}$ and $R^{32}$, forms a C-22/C-23 bond;

or, taken together with one of $R^{33}$ and $R^{34}$ when C-23 is absent, one of $R^{35}$ and $R^{36}$ forms a C-22/C-24 bond and the other is hydrogen or hydroxy;

or, taken together with one of $R^{33}$ and $R^{34}$, one of $R^{35}$ and $R^{36}$ forms a group having the formula —OC(CH$_3$)$_2$O—;

or, taken together, $R^{35}$ and $R^{36}$ form an oxo group or =NR$^{38}$ where $R^{38}$ is selected from (i) aryl-$C_1$-to-$C_{12}$-alkoxy, (ii) hydroxy, (iii) —OCH$_2$COOH, (iv) —OCH$_2$CHCH$_2$;

or, taken together with R and R', $R^{35}$ and $R^{36}$ form a C-21/C-22 bond and a heterocycle-forming group as described above;

or, taken together with $R^{31}$ and $R^{32}$, $R^{35}$ and $R^{36}$ form an indol or furan group as described above;

or, taken together with either or both of $R^{33}$ and $R^{34}$ and intervening carbon atoms C-22, C-23 and C-24, $R^{35}$ and $R^{36}$ form a fused, heterocyclic group selected from (i) a five- or six-membered, unsaturated group comprising a heteroatom selected from N, O and S, optionally comprising a second heteroatom selected from N, O and S with the proviso that when two heteroatoms are present, at least one is N, and optionally substituted with $C_1$-to-$C_8$-loweralkyl, aryl, aryl-$C_1$-to-$C_{12}$-alkyl, amido, formyl, —C(O)OR$^{11}$ or —C(O)R$^{41}$ where $R^{41}$ is $C_1$-to-$C_8$-loweralkyl, and (ii) a seven-membered, optionally unsaturated group having fused thereto a phenyl group optionally substituted with $C_1$-to-$C_8$-loweralkyl, $C_1$-to-$C_8$-alkoxy or halogen, wherein the ring member adjacent to C-22 is =N— and the ring member adjacent to C-24 is O or S; and (c) $R^{33}$ and $R^{34}$ are chosen such that (i) one of $R^{33}$ and $R^{34}$ is hydrogen and the other is selected from hydrogen, hydroxy, amino, —ONO$_2$, and -O-(hydroxyl protecting group); (ii) one of $R^{33}$ and $R^{34}$ is hydrogen and the other forms, with one of $R^{35}$ and $R^{36}$, a group having the formula —OC(CH$_3$)$_2$O—; or (iii) one of $R^{33}$ and $R^{34}$ forms a C-23/C-24 or, when C-23 is absent, a C-22/C-24 bond and the other is selected from hydrogen, hydroxy and $C_1$-to-$C_8$-loweralkoxy;

or, taken together, $R^{33}$ and $R^{34}$ form an oxo group;

or, taken together with one or more of $R^{31}$, $R^{32}$, $R^{35}$ and $R^{36}$ and the intervening carbon atoms, one or both of $R^{33}$ and $R^{34}$ form a group selected from (i) indole, where the nitrogen atom is adjacent to C-24, (ii) furan, with the oxygen atom attached to C-24, or (iii) a heterocyclic group as described above wherein at each occurrence the term heterocycle is independently selected from the group consisting of pyrrolyl, pyrazolyl, cytosinyl, thiocytosinyl, imidazolyl, pyridyl, pyrazinyl, pyrimidinyl, pyrldazinyl, xanthenyl, xanthonyl, xanthopterinyl, oxazoyl, thiouracilyl, isoxazolyl, indolyl, guinollnyl, uracilyl, urazolyl, uricyl, triazolyl, tetrazolyl, thiazolyl, isothiazolyl, isoquinolinyl, thyminyl, benzimidazolyl, benzothiazolyl, benzoxazolyl, furyl, thienyl and benzothienyl wherein any carbon or heteroatom with suitable valence may bear a substituent independently selected at each occurrence from the group consisting of halogen, hydroxy, —COOH, —CN, —CHO, —NO$_2$, —N$_3$, —(C$_1$-to-C$_6$-alkyl), —(C$_2$-to-C$_6$-alkenyl), —(C$_2$-to-C$_6$-alkynyl), mono-, di-, tri-, or perhalogenated-C$_1$-to-C$_6$-alkyl, —(CH$_2$)$_m$N(C$_1$-to-C$_6$-alkyl)$_2$ where m is zero to six, —S(O)$_s$(C$_1$-to-C$_6$-alkyl) where s is zero to two, —C(O)NH(C$_1$-to-C$_6$-alkyl), —(CH$_2$)$_m$O(-C$_1$-to-C$_6$-alkyl) wherein m is zero to six, —(CH$_2$)$_m$OC(O)(C$_1$-to-C$_6$-alkyl) wherein m is zero to six, —(CH$_2$)$_m$C(O)O(C$_1$-to-C$_6$-alkyl) wherein m is zero to six, —S(O)$_2$N(C$_1$-to-C$_6$-alkyl)$_2$, —C∫C—Si(CH$_3$)$_3$, —C$_1$-to-C$_6$-alkoxy, —OC(O)(Cl-to-C$_6$-alkyl), guanidino, unsubstituted aryl, and unsubstituted Het, and at each occurrence the term aryl is independently selected from the group consisting of phenyl, 1-naphthyl, 2-naphthyl, fluorenyl, (1,2)-dihydronaphthyl, (1,2,3,4,)-tetrahydronaphthyl and indenyl wherein the aryl group is unsubstituted or substituted with one, two or three substituents independently selected from halo, nitro, cyano, $C_1$-to-$C_{12}$-alkyl, $C_1$-to-$C_8$-alkoxy, and halosubstituted-$C_1$-to-$C_{12}$-alkyl.

2. A compound according to claim 1 having the formula

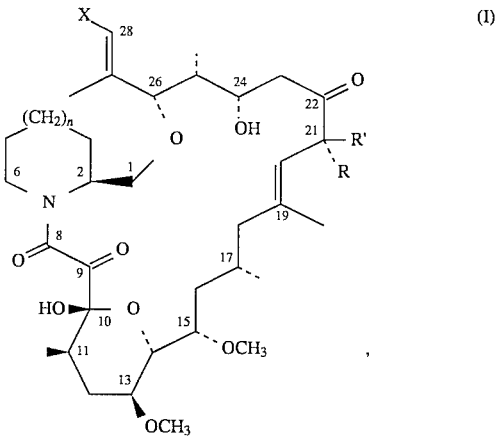

(I)

wherein X is as defined therein, n is one, R' is hydrogen, and R is selected from the group consisting of methyl, ethyl, propyl and allyl.

3. A compound according to claim 1 wherein Y is selected from the group consisting of

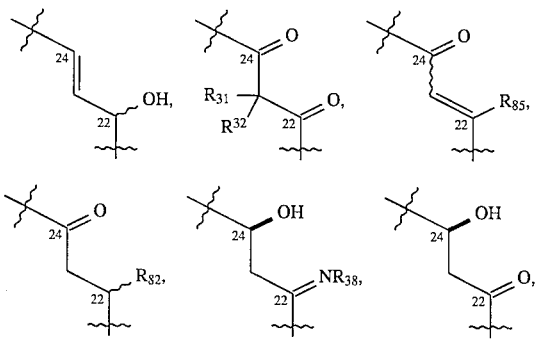

101
-continued

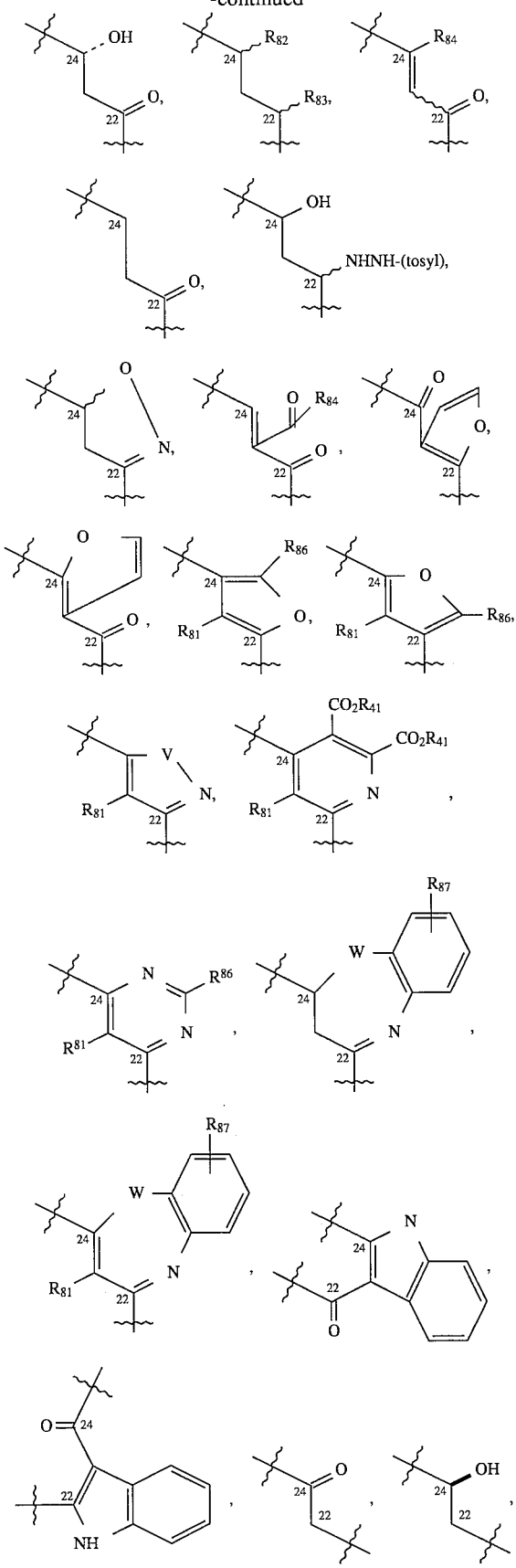

102
-continued

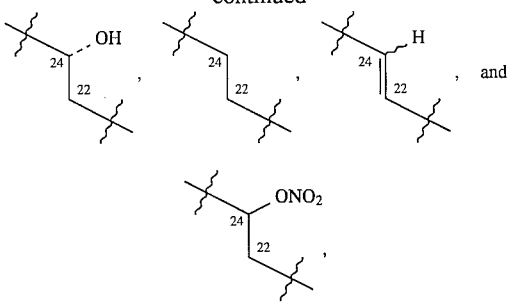

wherein $R^{31}$, $R^{32}$, $R^{38}$ and $R^{41}$ are as defined therein; $R^{81}$ is selected from the group consisting of hydrogen, $C_1$-to-$C_{12}$-alkyl, —C(O)NHR$^{61}$, —S(O)$_2$R$^{61}$ and —C(O)OR$^{61}$ wherein $R^{61}$ is as defined therein; $R^{82}$ and $R^{83}$ are independently selected from the group consisting of hydroxy and amino; $R^{84}$ is hydrogen, hydroxy or $C_1$-to-$C_8$-loweralkoxy; $R^{85}$ is hydrogen or hydroxy; $R^{86}$ is selected from the group consisting of hydrogen, $C_1$-to-$C_8$-loweralkyl, aryl, aryl-$C_1$-to-$C_{12}$-alkyl, amido, formyl, —C(O)R$^{41}$ and —C(O)OR$^{41}$; $R^{87}$ is selected from the group consisting of hydrogen, halogen, $C_1$-to-$C_8$-alkoxy and $C_1$-to-$C_8$-loweralkyl; V is selected from the group consisting of oxygen, —N(R$^{86}$)— and —NC(O)R$^{86}$—; and W is oxygen or sulfur.

4. A compound according to claim 3 wherein n is one, R' is hydrogen, and R is selected from the group consisting of methyl, ethyl, propyl and allyl.

5. A compound according to claim 6 wherein Y is selected from the group consisting of

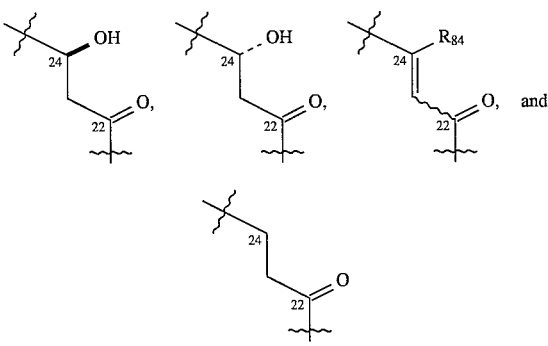

wherein $R^{84}$ is as defined therein.

6. A compound of the formula

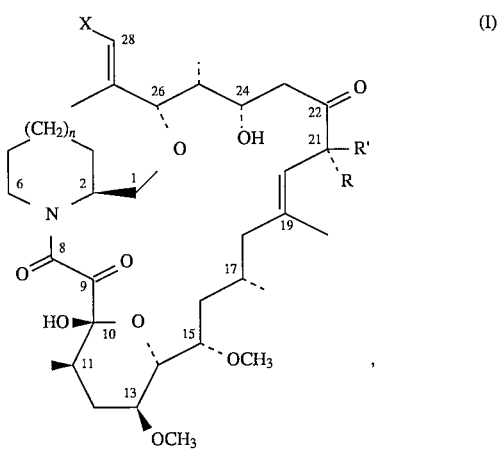

(I)

wherein X is

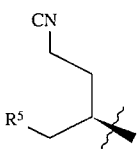

and (a) R=ethyl; R'=H; n=1; and $R^5$=formyl,
(b) R=ethyl; R'=H; n=1; and $R^5$ =ethenyl,
(c) R=ethyl; R'=H; n=1; and $R^5$=methyl 2-carboxylethenyl,
(d) R=ethyl; R'=H; n=1; and $R^5$=2-phenylethenyl,
(e) R=ethyl; R'=H; n=1; and $R^5$=N,N-dimethylhydrazone of formyl,
(f) R=ethyl; R'=H; n=1; and $R^5$=oxime of formyl,
(g) R=ethyl; R'=H; n=1; and $R^5$=O-carboxymethyl oxime of formyl,
(h) R=ethyl; R'=H; n: 1; and $R^5$=hydroxymethyl,
(i) R=ethyl; R'=H; n=1; and $R^5$=2,3-dihydroxypropyloxymethyl,
(j) R=ethyl; R'=H; n=1; and $R^5$=ethyloxymethyl,
(k) R=ethyl; R'=H; n=1; and $R^5$=ethyl carboxymethoxymethyl,
(l) R=ethyl; R'=H; n=1; and $R^5$=4-pyridyloxymethyl,
(m) R=ethyl; R'=H; n=1; and $R^5$=4-pyridylmethyloxymethyl,
(n) R=ethyl; R'=H; n=1; and $R^5$=methoxymethyl,
(o) R=ethyl; R'=H; n=1; and $R^5$=3-allyloxymethyl
(p) R=ethyl; R'=H; n=1; and $R^5$=phenoxymethyl,
(q) R=ethyl; R'=H; n=1; and $R^5$=benzyloxymethyl,
(r) R=ethyl; R'=H; n=1; $R^5$=N-tetrazoylmethyl,
(s) R=ethyl; R'=H; n=1; and $R^5$=N-(2-nitroimidazolyl)methyl,
(t) R=ethyl; R'=H; n=1 ; and $R^5$=4-morpholinomethyl,
(u) R=ethyl; R'=H; n=1; and $R^5$=4-methylpiperazinemethyl,
(v) R=ethyl; R'=H; n=1; $R^5$=azidomethyl,
(w) R=ethyl; R'=H; n=1; and $R^5$=aminomethyl,
(x) R=ethyl; R'=H; n=1; and $R^5$=carboxymethyl,
(y) R=ethyl; R'=H; n=1; and $R^5$=cyanomethyl,
(z) R=ethyl; R'=H; n=1; and $R^5$=—$CHR^6R^7$ wherein taken together $R^6$ and $R^7$ form an acetal of formula —S—$(CH_2)_3$—S—,
(aa) R=ethyl; R'=H; n=1; and $R^5$=—$CHR^6R^7$ wherein taken together $R^6$ and $R^7$ form an acetal of formula —S—$(CH_2)_2$—S—,
(bb) R=ethyl; R'=H; n=1; and $R^5$=—$CHR^6R^7$ wherein taken together $R^6$ and $R^7$ form an acetal of formula —S—(1,2-phenyl)—S—,
(cc) R=ethyl; R'=H; n=1; and $R^5$=—$CHR^6R^7$ wherein $R^6$=$R^7$=ethoxy,
(dd) R=ethyl; R'=H; n=1; and $R^5$=—$CHR^6R^7$ wherein taken together $R^6$ and $R^7$ form an acetal of formula —O—$(CH_2)_2$—O—,
(ee) R=ethyl; R'=H; n=1; and $R^5$=—$CHR^6R^7$ wherein taken together $R^6$ and $R^7$ form an acetal of formula —O—$(CH_2)_3$—O—,
(ff) R=ethyl; R'=H; n=1; and $R^5$=—$CHR^6R^7$ wherein taken together $R^6$ and $R^7$ form an acetal of formula —O—(1,2-phenyl)—O—,
(gg) R=ethyl; R'=H; n=1; and $R^5$=—$CHR^6R^7$ wherein $R^6$=methoxy; and $R^7$=ethyl,
(hh) R=ethyl; R'=H; n=1; and $R^5$=—$CHR^6R^7$ wherein $R^6$=methoxy; and $R^7$=methyl, or
(ii) R=ethyl; R'=H; n=1; and $R^5$=—$CHR^6R^7$ wherein $R^6$=methoxy; and $R^7$=n-propyl; or a pharmaceutically acceptable salt, ester, amide or prodrug thereof.

\* \* \* \* \*

UNITED STATES PATENT AND TRADEMARK OFFICE
CERTIFICATE OF CORRECTION

PATENT NO. : 5,561,228
DATED : October 1, 1996
INVENTOR(S) : Y. S. Or, et. Al.

It is certified that error appears in the above-indentified patent and that said Letters Patent is hereby corrected as shown below:

Column 96, line 40, change "CH2" to --$CH_2$--.

Column 96, lines 40-41, change "R14'" to --$R^{14}$"--.

Column 97, line 23, change "$CHR^6$   $R^{7}$" to --$CHR^6R^7$--.

Column 97, line 32, change "$CH_2OC(O)$   $R^{201}$" to --$CH_2OC(O)R^{201}$--.

Column 99, line 63, change "pyrldazinyl" to --pyridazinyl--.

Column 99, line 65, change "guinollnyl" to --quinolinyl--.

Column 100, line 12, change "$O(-C_1-to-C_6-$" to --$O(C_1-to-C_6-$ --.

Column 100, line 17, change "$Cl-to-C_6$" to --$C_1-to-C_6$--.

Column 101, lines 30-35, please correct the structural formula therein to look like this:

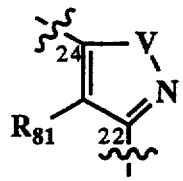

UNITED STATES PATENT AND TRADEMARK OFFICE
CERTIFICATE OF CORRECTION

PATENT NO. : 5,561,228
DATED : October 1, 1996
INVENTOR(S) : Y. S. Or, et. Al.

Page 2 of 3

It is certified that error appears in the above-indentified patent and that said Letters Patent is hereby corrected as shown below:

Column 102, line 30, change "claim 6" to --claim 3--.

Column 102, lines 50-65, please correct the structural formula therein to look like this:

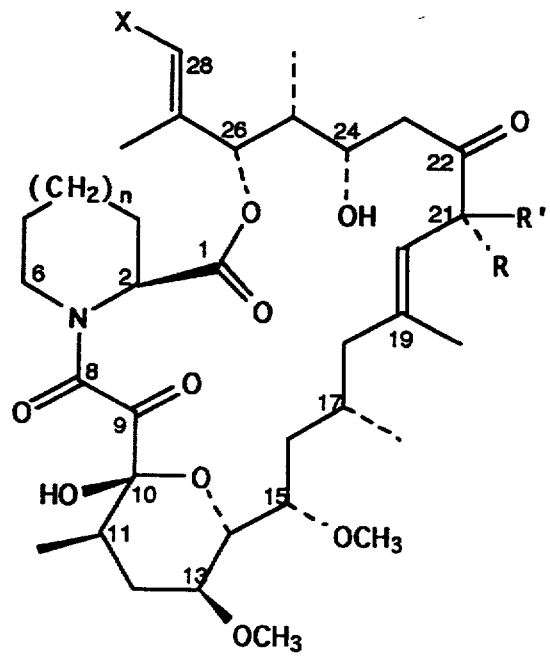

UNITED STATES PATENT AND TRADEMARK OFFICE
CERTIFICATE OF CORRECTION

PATENT NO. : 5,561,228
DATED : October 1, 1996
INVENTOR(S) : Y. S. Or, et. Al.

It is certified that error appears in the above-indentified patent and that said Letters Patent is hereby corrected as shown below:

Column 103, line 21, change "n: 1" to --n=1--.

Signed and Sealed this

Seventh Day of January, 1997

Attest:

BRUCE LEHMAN

Attesting Officer

Commissioner of Patents and Trademarks